US009000141B2

(12) United States Patent
Chang et al.

(10) Patent No.: US 9,000,141 B2
(45) Date of Patent: Apr. 7, 2015

(54) LOCALIZATION AND CHARACTERIZATION OF FLAVIVIRUS ENVELOPE GLYCOPROTEIN CROSS-REACTIVE EPITOPES AND METHODS FOR THEIR USE

(75) Inventors: Gwong-Jen J. Chang, Fort Collins, CO (US); Wayne D. Crill, Fort Collins, CO (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 1227 days.

(21) Appl. No.: 12/892,714

(22) Filed: Sep. 28, 2010

(65) Prior Publication Data

US 2011/0059131 A1 Mar. 10, 2011

Related U.S. Application Data

(62) Division of application No. 11/572,805, filed as application No. PCT/US2005/026672 on Jul. 27, 2005, now Pat. No. 7,906,292.

(60) Provisional application No. 60/591,898, filed on Jul. 27, 2004.

(51) Int. Cl.
C07H 21/00 (2006.01)
A61K 39/12 (2006.01)
C07K 14/005 (2006.01)
A61K 39/00 (2006.01)

(52) U.S. Cl.
CPC .............. *C07K 14/005* (2013.01); *A61K 39/00* (2013.01); *A61K 2039/53* (2013.01); *C12N 2770/24122* (2013.01)

(58) Field of Classification Search
CPC ..... A61K 35/76; A61K 39/162; G01N 33/53; G01N 33/56983; C07K 14/18; C07K 14/1825; C12N 2770/24111; C12N 2770/24121; C12N 2770/24122; C12N 2770/24131
See application file for complete search history.

(56) References Cited

U.S. PATENT DOCUMENTS

| | | | |
|---|---|---|---|
| 6,171,854 | B1 | 1/2001 | Galler et al. |
| 6,383,488 | B1 | 5/2002 | Ramudo et al. |
| 6,514,501 | B1 | 2/2003 | Kelly et al. |
| 6,869,793 | B2 | 3/2005 | Cardosa et al. |

FOREIGN PATENT DOCUMENTS

| | | |
|---|---|---|
| EP | 0 341 444 | 11/1989 |
| WO | WO 99/63095 | 12/1999 |
| WO | WO 02/081754 | 10/2002 |

OTHER PUBLICATIONS

Allison et al. "Mutational Evidence for an Internal Fusion Peptide in Flavivirus Envelope Protein E," *Journal of Virology* 75(9): 4268-4275 (2001).
Bhardwaj et al. "Biophysical Characterization and Vector-Specific Antagonist Activity of Domain III of the Tick-Borne Flavivirus Envelope Protein," *Journal of Virology* 75(4): 4002-4007 (2001).
Cardosa et al. "Antibodies against prM protein distinguish between previous infection with dengue and Japanese encephalitis viruses," *BMC Microbiology* 2(1): 9 (2002).
Chang et al. "A Single Intramuscular Injection of Recombinant Plasmid DNA Induces Protective Immunity and Prevents Japanese Encephalitis in Mice," *Journal of Virology* 74(9): 4244-4252 (2000).
Chang et al. "Enhancing biosynthesis and secretion of premembrane and envelope proteins by the chimeric plasmid of dengue virus type 2 and Japanese encephalitis virus," *Virology* 306: 170-180 (2003).
Chiou et al., "Enzyme-Linked Immunosorbent Assays Using Novel Japanese Encephalitis Virus Antigen Improve the Accuracy of Clinical Diagnosis of Flavivirus Infection," *Clin. Vaccine Immunol.* 15(5):825-835 (2008).
Crill et al., "Humoral Immune Responses of Dengue Fever Patients Using Epitope-Specific Serotype-2 Virus-Like Particle Antigens," *PLoS One* 4(4):34991 (2009), 18 pages.
Crill et al. "A Detailed Mutagenesis Study of Flavivirus Cross-Reactive Epitopes using West Nile Virus-like Particles," *Journal of General Virology* 88(4): 1169-1174 (2007).
Crill and Chang, "Localization and characterization of flavivrius envelope glycoprotein cross-reactive epitopes," *J. Virology* 78(34):13975-73986 (2004).
Greenspan et al. "Defining epitopes: It's not as easy as it seems," *Nature Biotechnology* 17: 936-937 (1999).
Guerois et al., "Predicting Changes in the Stability of Proteins and Protein Complexes: A Study of More Than 1000 Mutations," *J. Mol. Biol.* 320:369-387 (2002).
Halstead et al. "The future of dengue vaccines," *The Lancet* 360: 1243-1245 (2002).
Hoshino et al., "Mapping of antigenic sites involved in serotype-cross-reactive neutralization on group A rotovirus outercapsid glycoprotein VP7," *Virol.* 199:233-237 (1994).
Lescar et al. "The Fusion Glycoprotein Shell of Semliki Forest Virus: An Icosahedral Assembly Primed for Fusogenic Activation at Endosomal pH," *Cell* 105: 137-148 (2001).
Modis et al., "A ligand-binding pocket in the dengue virus envelope protein," *PNAS* 100(12):6986-6991 (2003).
Op De Beeck et al. "Role of the Transmembrane Domains of prM and E Proteins in the Formation of Yellow Fever Virus Envelope," *Journal of Virology* 77(2): 813-820 (2003).
Pappu et al., "Molecular characterization of a structural epitope that is largely conserved among severe isolates of a plant virus," *Proc. Natl. Acad. Sci. USA*, 90:3641-3644, (Apr. 1993).
Rey et al., "The envelope glycoprotein from the tick-borne encephalitis virus at 2 Å resolution," *Nature* 375:291-298 (1995).
Rey, "Dengue virus envelope glycoprotein structure: New insight into its interactions during viral entry," *PNAS* 100:6899 (2003).
Roberson et al., "Differentiation of West Nile and St. Louis Encephalitis Virus Infections by Use of Noninfectious Virus-Like Particles with Reduced Cross-Reactivity," *J. Clin. Microbiol.*, 45:3167-3174, (Oct. 2007).

(Continued)

*Primary Examiner* — Stacy B Chen
(74) *Attorney, Agent, or Firm* — Klarquist Sparkman, LLP

(57) ABSTRACT

Disclosed herein is a method for identifying flavivirus cross-reactive epitopes. Also provided are flavivirus E-glycoprotein cross-reactive epitopes and flavivirus E-glycoprotein cross-reactive epitopes having reduced or ablated cross-reactivity (and polypeptides comprising such epitopes), as well as methods of using these molecules to elicit an immune response against a flavivirus and to detect a flaviviral infection.

21 Claims, 3 Drawing Sheets

(56) References Cited

OTHER PUBLICATIONS

Roehrig et al., "Monoclonal Antibody Mapping of the Envelope Glycoprotein of the Dengue 2 Virus, Jamaica," *Virology* 246(2):317-328 (1998).

Taniguchi et al., "Cross-reactive and serotype-specific neutralization epitopes on VP7 of human rotavirus: nucleotide sequence analysis of antigenic mutants selected with monoclonal antibodies," *J. Virol.* 62(6):1870-1874 (1988).

Trainor et al. "Mutation Analysis of the Fusion Domain Region of St. Louis Encephalitis Virus Envelope," *Virology* 360(2): 398-406 (2006).

Twiddy et al. "Phylogenetic evidence for adaptive evolution of dengue viruses in nature," *Journal of General Virology* 83: 1679-1689 (2002).

NCBI Protein Sequence: "Envelope glycoprotein [Dengue virus type 2]," Accession No. AAO26457 (Jun. 24, 2003) (2 pages).

NCBI Protein Sequence: "Genome polyprotein," Accession No. P09866 (Apr. 3, 2007) (10 pages).

NCBI Protein Sequence: "Polyprotein [Dengue virus type 2 (strain 16681)]," Accession No. AAB58782 (Jun. 4, 19997) (4 pages).

NCBI Protein Sequence: "Genome polyprotein," Accession No. P27915 (Apr. 3, 2007) (9 pages).

NCBI Protein Sequence: "Genome polyprotein," Accession No. P09732 (Apr. 3, 2007) (6 pages).

NCBI Protein Sequence: "Genome polyprotein," Accession No. P14335 (Mar. 20, 2007) (8 pages).

NCBI Protein Sequence: "Genome polyprotein," Accession No. P05769 (Mar. 20, 2007) (10 pages).

NCBI Protein Sequence: "Genome polyprotein," Accession No. P03314 (Apr. 3, 2007) (28 pages).

NCBI Protein Sequence: "Genome polyprotein," Accession No. Q04538 (Apr. 3, 2007) (9 pages).

FIG. 2C

MAbs: 4G2 ■  6B6C-1 ▨  1B7-5 ▨

G104†, G106, L107, E126, E126/T226, W231†

FIG. 3  Percent of Substitutions Altering MAb Reactivities

☐ SLEV
▨ WNV

Total Mabs (14, 10): n=11, n=14
Group/Subgrp- (8,6): n=9, n=9
Complex/Subcomp- (3,2): n=4, n=1
Type-Specific (3,2): n=1, n=1

SEQUENCE LISTING

<160> NUMBER OF SEQ ID NOS: 87

<210> SEQ ID NO 1
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 1
tgttgttgtg ttggttaggt ttgcctctat acag                                34

<210> SEQ ID NO 2
<211> LENGTH: 39
<212> TYPE: DNA
<213> ORGANISM: Artificial Sequence
<220> FEATURE:
<223> OTHER INFORMATION: Mutagenic oligonucleotide primer.

<400> SEQUENCE: 2
tgggttcccc ttgcattggg cagcgagatt ctgttgttg                              39

<210> SEQ ID NO 3
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 3
ttcatttagg ctgggttccc ctcgtgttgg gcag                                   34

<210> SEQ ID NO 4
<211> LENGTH: 45
<212> TYPE: DNA
<213> ORGANISM: Artificial Sequence
<220> FEATURE:
<223> OTHER INFORMATION: Mutagenic oligonucleotide primer.

<400> SEQUENCE: 4 cccttttccaa atagtccaca gtgatttccc catcctctgt ctacc                      45

<210> SEQ ID NO 5
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 5
gcctcccttt ccaaatagtt gacatccatt tcccca                                 36

<210> SEQ ID NO 6
<211> LENGTH: 44
<212> TYPE: DNA
<213> ORGANISM: Artificial Sequence
<220> FEATURE:
<223> OTHER INFORMATION: Mutagenic oligonucleotide primer.

<400> SEQUENCE: 6
ggtcacaatg cctcccttc caaattttcc acatccattt cccc                         44

<210> SEQ ID NO 7
<211> LENGTH: 42
<212> TYPE: DNA
<213> ORGANISM: Artificial Sequence
<220> FEATURE:
<223> OTHER INFORMATION: Mutagenic oligonucleotide primer.

<400> SEQUENCE: 7
agttttctgg ttgcacaact tttcctgcca tgttcttttt gc                          42

<210> SEQ ID NO 8
<211> LENGTH: 39
<212> TYPE: DNA
<213> ORGANISM: Artificial Sequence
<220> FEATURE:
<223> OTHER INFORMATION: Mutagenic oligonucleotide primer.

<400> SEQUENCE: 8
gtatccaatt tgacccttga ttgtccgctc cgggcaacc                              39

<210> SEQ ID NO 9
<211> LENGTH: 35

-continued

```
<212> TYPE: DNA
<213> ORGANISM: Artificial Sequence
<220> FEATURE:
<223> OTHER INFORMATION: Mutagenic oligonucleotide primer.

<400> SEQUENCE: 9
gtctctttct gtatgaaatt tgacccttgt gtgtc                                  35

<210> SEQ ID NO 10
<211> LENGTH: 44
<212> TYPE: DNA
<213> ORGANISM: Artificial Sequence
<220> FEATURE:
<223> OTHER INFORMATION: Mutagenic oligonucleotide primer.

<400> SEQUENCE: 10
aatgtctctt tctgtatcag atttgaccct tgtgtgtccg ctcc                        44

<210> SEQ ID NO 11
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 11
tcctgtttct tcgcacgggg atttttgaaa gtgacc                                 36

<210> SEQ ID NO 12
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 12
acaacaacat cctgtcgctt cgcatgggga tttttg                                 36

<210> SEQ ID NO 13
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      envelope chimera.
<220> FEATURE:
<221> NAME/KEY: CDS
<222> LOCATION: (1)..(1485)
<220> FEATURE:
<221> NAME/KEY: misc_feature
<222> LOCATION: (310)..(312)
<223> OTHER INFORMATION: Mutagenesis of GGA codon to CAC codon produces
      a G104H substitution.
<220> FEATURE:
<221> NAME/KEY: misc_feature
<222> LOCATION: (316)..(318)
<223> OTHER INFORMATION: Mutagenesis of GGA codon to CAA codon produces
      a G106Q substitution.
<220> FEATURE:
<221> NAME/KEY: misc_feature
<222> LOCATION: (319)..(321)
<223> OTHER INFORMATION: Mutagenesis of CTA codon to AAA codon produces
      a L107K substitution.
<220> FEATURE:
<221> NAME/KEY: misc_feature
<222> LOCATION: (376)..(378)
<223> OTHER INFORMATION: Mutagenesis of GAA codon to GCA codon produces
      a E126A substitution.
<220> FEATURE:
<221> NAME/KEY: misc_feature
<222> LOCATION: (676)..(678)
```

<223> OTHER INFORMATION: Mutagenesis of ACA codon to AAT codon produces
a T226N substitution.
<220> FEATURE:
<221> NAME/KEY: misc_feature
<222> LOCATION: (691)..(693)
<223> OTHER INFORMATION: Mutagenesis of TGG codon to TTC codon produces
a W231F substitution.
<220> FEATURE:
<221> NAME/KEY: misc_feature
<222> LOCATION: (691)..(693)
<223> OTHER INFORMATION: Mutagenesis of TGG codon to CTG codon produces
a W231L substitution.

<400> SEQUENCE: 13

```
atg cgt tgc ata gga atg tca aat aga gac ttt gtg gaa ggg gtt tca      48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg      96
Gly Gly Ser Trp Val Asp Ile Val Leu Glu His Gly Ser Cys Val Thr
            20                  25                  30 acg atg gca aaa aac aaa cca aca ttg gat ttt gaa ctg ata aaa aca     144
Thr Met Ala Lys Asn Lys Pro Thr Leu Asp Phe Glu Leu Ile Lys Thr
        35                  40                  45 gaa gcc aaa cag cct gcc acc cta agg aag tac tgt ata gag gca aag     192
Glu Ala Lys Gln Pro Ala Thr Leu Arg Lys Tyr Cys Ile Glu Ala Lys
    50                  55                  60 cta acc aac aca aca aca gaa tct cgc tgc cca aca caa ggg gaa ccc     240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg     288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc     336
Val Asp Arg Gly Trp Gly Asn Gly Cys Gly Leu Phe Gly Lys Gly Gly
            100                 105                 110 att gtg acc tgt gct atg ttc aga tgc aaa aag aac atg gaa gga aaa     384
Ile Val Thr Cys Ala Met Phe Arg Cys Lys Lys Asn Met Glu Gly Lys
        115                 120                 125 gtt gtg caa cca gaa aac ttg gaa tac acc att gtg ata aca cct cac     432
Val Val Gln Pro Glu Asn Leu Glu Tyr Thr Ile Val Ile Thr Pro His
    130                 135                 140 tca ggg gaa gag cat gca gtc gga aat gac aca gga aaa cat ggc aag     480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca     528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac     576
Gly Tyr Gly Thr Val Thr Met Glu Cys Ser Pro Arg Thr Gly Leu Asp
            180                 185                 190 ttc aat gag atg gtg ttg ttg cag atg gaa aat aaa gct tgg ctg gtg     624
Phe Asn Glu Met Val Leu Leu Gln Met Glu Asn Lys Ala Trp Leu Val
        195                 200                 205 cac agg caa tgg ttc cta gac ctg ccg tta cca tgg ttg ccc gga gcg     672
His Arg Gln Trp Phe Leu Asp Leu Pro Leu Pro Trp Leu Pro Gly Ala
    210                 215                 220 gac aca caa ggg tca aat tgg ata cag aaa gag aca ttg gtc act ttc     720
Asp Thr Gln Gly Ser Asn Trp Ile Gln Lys Glu Thr Leu Val Thr Phe
225                 230                 235                 240 aaa aat ccc cat gcg aag aaa cag gat gtt gtt gtt tta gga tcc caa     768
Lys Asn Pro His Ala Lys Lys Gln Asp Val Val Val Leu Gly Ser Gln
                245                 250                 255
```

| | | | | | | | | | | | | | | | | |
|---|---|---|---|---|---|---|---|---|---|---|---|---|---|---|---|---|
| gaa | ggg | gcc | atg | cac | aca | gca | ctt | aca | ggg | gcc | aca | gaa | atc | caa | atg | 816 |
| Glu | Gly | Ala | Met | His | Thr | Ala | Leu | Thr | Gly | Ala | Thr | Glu | Ile | Gln | Met | |
| | | | 260 | | | | | 265 | | | | | 270 | | | |
| tca | tca | gga | aac | tta | ctc | ttc | aca | gga | cat | ctc | aag | tgc | agg | ctg | aga | 864 |
| Ser | Ser | Gly | Asn | Leu | Leu | Phe | Thr | Gly | His | Leu | Lys | Cys | Arg | Leu | Arg | |
| | | 275 | | | | | 280 | | | | | 285 | | | | |
| atg | gac | aag | cta | cag | ctc | aaa | gga | atg | tca | tac | tct | atg | tgc | aca | gga | 912 |
| Met | Asp | Lys | Leu | Gln | Leu | Lys | Gly | Met | Ser | Tyr | Ser | Met | Cys | Thr | Gly | |
| | 290 | | | | | 295 | | | | | 300 | | | | | |
| aag | ttt | aaa | gtt | gtg | aag | gaa | ata | gca | gaa | aca | caa | cat | gga | aca | ata | 960 |
| Lys | Phe | Lys | Val | Val | Lys | Glu | Ile | Ala | Glu | Thr | Gln | His | Gly | Thr | Ile | |
| 305 | | | | | 310 | | | | | 315 | | | | | 320 | |
| gtt | atc | aga | gtg | caa | tat | gaa | ggg | gac | ggc | tct | cca | tgc | aag | atc | cct | 1008 |
| Val | Ile | Arg | Val | Gln | Tyr | Glu | Gly | Asp | Gly | Ser | Pro | Cys | Lys | Ile | Pro | |
| | | | | 325 | | | | | 330 | | | | | 335 | | |
| ttt | gag | ata | atg | gat | ttg | gaa | aaa | aga | cat | gtc | tta | ggt | cgc | ctg | att | 1056 |
| Phe | Glu | Ile | Met | Asp | Leu | Glu | Lys | Arg | His | Val | Leu | Gly | Arg | Leu | Ile | |
| | | | 340 | | | | | 345 | | | | | 350 | | | |
| aca | gtc | aac | cca | att | gtg | aca | gaa | aaa | gat | agc | cca | gtc | aac | ata | gaa | 1104 |
| Thr | Val | Asn | Pro | Ile | Val | Thr | Glu | Lys | Asp | Ser | Pro | Val | Asn | Ile | Glu | |
| | | 355 | | | | | 360 | | | | | 365 | | | | |
| gca | gaa | cct | cca | ttc | gga | gac | agc | tac | atc | atc | ata | gga | gta | gag | ccg | 1152 |
| Ala | Glu | Pro | Pro | Phe | Gly | Asp | Ser | Tyr | Ile | Ile | Ile | Gly | Val | Glu | Pro | |
| | 370 | | | | | 375 | | | | | 380 | | | | | |
| gga | caa | ctg | aag | ctc | aac | tgg | ttt | aag | aaa | gga | agc | acg | ctg | ggc | aag | 1200 |
| Gly | Gln | Leu | Lys | Leu | Asn | Trp | Phe | Lys | Lys | Gly | Ser | Thr | Leu | Gly | Lys | |
| 385 | | | | | 390 | | | | | 395 | | | | | 400 | |
| gcc | ttt | tca | aca | act | ttg | aag | gga | gct | caa | aga | ctg | gca | gcg | ttg | ggc | 1248 |
| Ala | Phe | Ser | Thr | Thr | Leu | Lys | Gly | Ala | Gln | Arg | Leu | Ala | Ala | Leu | Gly | |
| | | | | 405 | | | | | 410 | | | | | 415 | | |
| gac | aca | gcc | tgg | gac | ttt | ggc | tct | att | gga | ggg | gtc | ttc | aac | tcc | ata | 1296 |
| Asp | Thr | Ala | Trp | Asp | Phe | Gly | Ser | Ile | Gly | Gly | Val | Phe | Asn | Ser | Ile | |
| | | | 420 | | | | | 425 | | | | | 430 | | | |
| gga | aaa | gcc | gtt | cac | caa | gtg | ttt | ggt | ggt | gcc | ttc | aga | aca | ctc | ttt | 1344 |
| Gly | Lys | Ala | Val | His | Gln | Val | Phe | Gly | Gly | Ala | Phe | Arg | Thr | Leu | Phe | |
| | | 435 | | | | | 440 | | | | | 445 | | | | |
| ggg | gga | atg | tct | tgg | atc | aca | caa | ggg | cta | atg | ggt | gcc | cta | ctg | ctc | 1392 |
| Gly | Gly | Met | Ser | Trp | Ile | Thr | Gln | Gly | Leu | Met | Gly | Ala | Leu | Leu | Leu | |
| | 450 | | | | | 455 | | | | | 460 | | | | | |
| tgg | atg | ggc | gtc | aac | gca | cga | gac | cga | tca | att | gct | ttg | gcc | ttc | tta | 1440 |
| Trp | Met | Gly | Val | Asn | Ala | Arg | Asp | Arg | Ser | Ile | Ala | Leu | Ala | Phe | Leu | |
| 465 | | | | | 470 | | | | | 475 | | | | | 480 | |
| gcc | aca | ggg | ggt | gtg | ctc | gtg | ttc | tta | gcg | acc | aat | gtg | cat | gct | taa | 1488 |
| Ala | Thr | Gly | Gly | Val | Leu | Val | Phe | Leu | Ala | Thr | Asn | Val | His | Ala | | |
| | | | | 485 | | | | | 490 | | | | | 495 | | |

<210> SEQ ID NO 14
<211> LENGTH: 495
<212> TYPE: PRT
<213> ORGANISM: Artificial Sequence
<220> FEATURE:
<223> OTHER INFORMATION: Synthetic Construct

<400> SEQUENCE: 14

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

-continued

```
Glu Ala Lys Gln Pro Ala Thr Leu Arg Lys Tyr Cys Ile Glu Ala Lys
 50                  55                  60

Leu Thr Asn Thr Thr Thr Glu Ser Arg Cys Pro Thr Gln Gly Glu Pro
 65                  70                  75                  80

Ser Leu Asn Glu Glu Gln Asp Lys Arg Phe Val Cys Lys His Ser Met
                 85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
            435                 440                 445

Gly Gly Met Ser Trp Ile Thr Gln Gly Leu Met Gly Ala Leu Leu Leu
450                 455                 460

Trp Met Gly Val Asn Ala Arg Asp Arg Ser Ile Ala Leu Ala Phe Leu
```

```
                465                 470                 475                 480
Ala Thr Gly Gly Val Leu Val Phe Leu Ala Thr Asn Val His Ala
                    485                 490                 495

<210> SEQ ID NO 15
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      G104H envelope chimera.
<220> FEATURE:
<221> NAME/KEY: CDS
<222> LOCATION: (1)..(1485)

<400> SEQUENCE: 15 atg cgt tgc ata gga atg tca aat aga gac ttt gtg gaa ggg gtt tca      48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg      96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca     144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag     192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc     240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg     288
Ser Leu Asn Glu Glu Gln Asp Lys Arg Phe Val Cys Lys His Ser Met
                85                  90                  95 gta gac aga gga tgg gga aat cac tgt gga cta ttt gga aag gga ggc     336
Val Asp Arg Gly Trp Gly Asn His Cys Gly Leu Phe Gly Lys Gly Gly
                100                 105                 110 att gtg acc tgt gct atg ttc aga tgc aaa aag aac atg gaa gga aaa     384
Ile Val Thr Cys Ala Met Phe Arg Cys Lys Lys Asn Met Glu Gly Lys
            115                 120                 125 gtt gtg caa cca gaa aac ttg gaa tac acc att gtg ata aca cct cac     432
Val Val Gln Pro Glu Asn Leu Glu Tyr Thr Ile Val Ile Thr Pro His
        130                 135                 140 tca ggg gaa gag cat gca gtc gga aat gac aca gga aaa cat ggc aag     480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca     528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac     576
Gly Tyr Gly Thr Val Thr Met Glu Cys Ser Pro Arg Thr Gly Leu Asp
                180                 185                 190 ttc aat gag atg gtg ttg ttg cag atg gaa aat aaa gct tgg ctg gtg     624
Phe Asn Glu Met Val Leu Leu Gln Met Glu Asn Lys Ala Trp Leu Val
            195                 200                 205 cac agg caa tgg ttc cta gac ctg ccg tta cca tgg ttg ccc gga gcg     672
His Arg Gln Trp Phe Leu Asp Leu Pro Leu Pro Trp Leu Pro Gly Ala
        210                 215                 220 gac aca caa ggg tca aat tgg ata cag aaa gag aca ttg gtc act ttc     720
Asp Thr Gln Gly Ser Asn Trp Ile Gln Lys Glu Thr Leu Val Thr Phe
225                 230                 235                 240
```

```
aaa aat ccc cat gcg aag aaa cag gat gtt gtt gtt tta gga tcc caa      768
Lys Asn Pro His Ala Lys Lys Gln Asp Val Val Val Leu Gly Ser Gln
            245                 250                 255 gaa ggg gcc atg cac aca gca ctt aca ggg gcc aca gaa atc caa atg      816
Glu Gly Ala Met His Thr Ala Leu Thr Gly Ala Thr Glu Ile Gln Met
        260                 265                 270 tca tca gga aac tta ctc ttc aca gga cat ctc aag tgc agg ctg aga      864
Ser Ser Gly Asn Leu Leu Phe Thr Gly His Leu Lys Cys Arg Leu Arg
    275                 280                 285 atg gac aag cta cag ctc aaa gga atg tca tac tct atg tgc aca gga      912
Met Asp Lys Leu Gln Leu Lys Gly Met Ser Tyr Ser Met Cys Thr Gly
290                 295                 300 aag ttt aaa gtt gtg aag gaa ata gca gaa aca caa cat gga aca ata      960
Lys Phe Lys Val Val Lys Glu Ile Ala Glu Thr Gln His Gly Thr Ile
305                 310                 315                 320 gtt atc aga gtg caa tat gaa ggg gac ggc tct cca tgc aag atc cct     1008
Val Ile Arg Val Gln Tyr Glu Gly Asp Gly Ser Pro Cys Lys Ile Pro
                325                 330                 335 ttt gag ata atg gat ttg gaa aaa aga cat gtc tta ggt cgc ctg att     1056
Phe Glu Ile Met Asp Leu Glu Lys Arg His Val Leu Gly Arg Leu Ile
            340                 345                 350 aca gtc aac cca att gtg aca gaa aaa gat agc cca gtc aac ata gaa     1104
Thr Val Asn Pro Ile Val Thr Glu Lys Asp Ser Pro Val Asn Ile Glu
        355                 360                 365 gca gaa cct cca ttc gga gac agc tac atc atc ata gga gta gag ccg     1152
Ala Glu Pro Pro Phe Gly Asp Ser Tyr Ile Ile Ile Gly Val Glu Pro
    370                 375                 380 gga caa ctg aag ctc aac tgg ttt aag aaa gga agc acg ctg ggc aag     1200
Gly Gln Leu Lys Leu Asn Trp Phe Lys Lys Gly Ser Thr Leu Gly Lys
385                 390                 395                 400 gcc ttt tca aca act ttg aag gga gct caa aga ctg gca gcg ttg ggc     1248
Ala Phe Ser Thr Thr Leu Lys Gly Ala Gln Arg Leu Ala Ala Leu Gly
                405                 410                 415 gac aca gcc tgg gac ttt ggc tct att gga ggg gtc ttc aac tcc ata     1296
Asp Thr Ala Trp Asp Phe Gly Ser Ile Gly Gly Val Phe Asn Ser Ile
            420                 425                 430 gga aaa gcc gtt cac caa gtg ttt ggt ggt gcc ttc aga aca ctc ttt     1344
Gly Lys Ala Val His Gln Val Phe Gly Gly Ala Phe Arg Thr Leu Phe
        435                 440                 445 ggg gga atg tct tgg atc aca caa ggg cta atg ggt gcc cta ctg ctc     1392
Gly Gly Met Ser Trp Ile Thr Gln Gly Leu Met Gly Ala Leu Leu Leu
    450                 455                 460 tgg atg ggc gtc aac gca cga gac cga tca att gct ttg gcc ttc tta     1440
Trp Met Gly Val Asn Ala Arg Asp Arg Ser Ile Ala Leu Ala Phe Leu
465                 470                 475                 480 gcc aca ggg ggt gtg ctc gtg ttc tta gcg acc aat gtg cat gct taa     1488
Ala Thr Gly Gly Val Leu Val Phe Leu Ala Thr Asn Val His Ala
                485                 490                 495

<210> SEQ ID NO 16
<211> LENGTH: 495
<212> TYPE: PRT
<213> ORGANISM: Artificial Sequence
<220> FEATURE:
<223> OTHER INFORMATION: Synthetic Construct

<400> SEQUENCE: 16

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30
```

-continued

```
Thr Met Ala Lys Asn Lys Pro Thr Leu Asp Phe Glu Leu Ile Lys Thr
         35                  40                  45

Glu Ala Lys Gln Pro Ala Thr Leu Arg Lys Tyr Cys Ile Glu Ala Lys
 50                  55                  60

Leu Thr Asn Thr Thr Thr Glu Ser Arg Cys Pro Thr Gln Gly Glu Pro
 65                  70                  75                  80

Ser Leu Asn Glu Glu Gln Asp Lys Arg Phe Val Cys Lys His Ser Met
                 85                  90                  95

Val Asp Arg Gly Trp Gly Asn His Cys Gly Leu Phe Gly Lys Gly Gly
                100                 105                 110

Ile Val Thr Cys Ala Met Phe Arg Cys Lys Lys Asn Met Glu Gly Lys
                115                 120                 125

Val Val Gln Pro Glu Asn Leu Glu Tyr Thr Ile Val Ile Thr Pro His
                130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
                180                 185                 190

Phe Asn Glu Met Val Leu Leu Gln Met Glu Asn Lys Ala Trp Leu Val
                195                 200                 205

His Arg Gln Trp Phe Leu Asp Leu Pro Leu Pro Trp Leu Pro Gly Ala
                210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
                275                 280                 285

Met Asp Lys Leu Gln Leu Lys Gly Met Ser Tyr Ser Met Cys Thr Gly
                290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Glu Pro
                370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
                420                 425                 430

Gly Lys Ala Val His Gln Val Phe Gly Gly Ala Phe Arg Thr Leu Phe
                435                 440                 445
```

```
Gly Gly Met Ser Trp Ile Thr Gln Gly Leu Met Gly Ala Leu Leu Leu
            450             455             460

Trp Met Gly Val Asn Ala Arg Asp Arg Ser Ile Ala Leu Ala Phe Leu
465             470             475             480

Ala Thr Gly Gly Val Leu Val Phe Leu Ala Thr Asn Val His Ala
                485             490             495

<210> SEQ ID NO 17
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      G106Q envelope chimera.
<220> FEATURE:
<221> NAME/KEY: CDS
<222> LOCATION: (1)..(1485)

<400> SEQUENCE: 17 atg cgt tgc ata gga atg tca aat aga gac ttt gtg gaa ggg gtt tca    48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg    96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca   144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag   192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc   240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg   288
Ser Leu Asn Glu Glu Gln Asp Lys Arg Phe Val Cys Lys His Ser Met
                85                  90                  95 gta gac aga gga tgg gga aat gga tgt caa cta ttt gga aag gga ggc   336
Val Asp Arg Gly Trp Gly Asn Gly Cys Gln Leu Phe Gly Lys Gly Gly
            100                 105                 110 att gtg acc tgt gct atg ttc aga tgc aaa aag aac atg gaa gga aaa   384
Ile Val Thr Cys Ala Met Phe Arg Cys Lys Lys Asn Met Glu Gly Lys
        115                 120                 125 gtt gtg caa cca gaa aac ttg gaa tac acc att gtg ata aca cct cac   432
Val Val Gln Pro Glu Asn Leu Glu Tyr Thr Ile Val Ile Thr Pro His
    130                 135                 140 tca ggg gaa gag cat gca gtc gga aat gac aca gga aaa cat ggc aag   480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca   528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac   576
Gly Tyr Gly Thr Val Thr Met Glu Cys Ser Pro Arg Thr Gly Leu Asp
            180                 185                 190 ttc aat gag atg gtg ttg ttg cag atg gaa aat aaa gct tgg ctg gtg   624
Phe Asn Glu Met Val Leu Leu Gln Met Glu Asn Lys Ala Trp Leu Val
        195                 200                 205 cac agg caa tgg ttc cta gac ctg ccg tta cca tgg ttg ccc gga gcg   672
His Arg Gln Trp Phe Leu Asp Leu Pro Leu Pro Trp Leu Pro Gly Ala
    210                 215                 220
```

```
gac aca caa ggg tca aat tgg ata cag aaa gag aca ttg gtc act ttc       720
Asp Thr Gln Gly Ser Asn Trp Ile Gln Lys Glu Thr Leu Val Thr Phe
225                 230                 235                 240 aaa aat ccc cat gcg aag aaa cag gat gtt gtt gtt tta gga tcc caa       768
Lys Asn Pro His Ala Lys Lys Gln Asp Val Val Val Leu Gly Ser Gln
            245                 250                 255 gaa ggg gcc atg cac aca gca ctt aca ggg gcc aca gaa atc caa atg       816
Glu Gly Ala Met His Thr Ala Leu Thr Gly Ala Thr Glu Ile Gln Met
        260                 265                 270 tca tca gga aac tta ctc ttc aca gga cat ctc aag tgc agg ctg aga       864
Ser Ser Gly Asn Leu Leu Phe Thr Gly His Leu Lys Cys Arg Leu Arg
    275                 280                 285 atg gac aag cta cag ctc aaa gga atg tca tac tct atg tgc aca gga       912
Met Asp Lys Leu Gln Leu Lys Gly Met Ser Tyr Ser Met Cys Thr Gly
290                 295                 300 aag ttt aaa gtt gtg aag gaa ata gca gaa aca caa cat gga aca ata       960
Lys Phe Lys Val Val Lys Glu Ile Ala Glu Thr Gln His Gly Thr Ile
305                 310                 315                 320 gtt atc aga gtg caa tat gaa ggg gac ggc tct cca tgc aag atc cct      1008
Val Ile Arg Val Gln Tyr Glu Gly Asp Gly Ser Pro Cys Lys Ile Pro
            325                 330                 335 ttt gag ata atg gat ttg gaa aaa aga cat gtc tta ggt cgc ctg att      1056
Phe Glu Ile Met Asp Leu Glu Lys Arg His Val Leu Gly Arg Leu Ile
        340                 345                 350 aca gtc aac cca att gtg aca gaa aaa gat agc cca gtc aac ata gaa      1104
Thr Val Asn Pro Ile Val Thr Glu Lys Asp Ser Pro Val Asn Ile Glu
    355                 360                 365 gca gaa cct cca ttc gga gac agc tac atc atc ata gga gta gag ccg      1152
Ala Glu Pro Pro Phe Gly Asp Ser Tyr Ile Ile Ile Gly Val Glu Pro
370                 375                 380 gga caa ctg aag ctc aac tgg ttt aag aaa gga agc acg ctg ggc aag      1200
Gly Gln Leu Lys Leu Asn Trp Phe Lys Lys Gly Ser Thr Leu Gly Lys
385                 390                 395                 400 gcc ttt tca aca act ttg aag gga gct caa aga ctg gca gcg ttg ggc      1248
Ala Phe Ser Thr Thr Leu Lys Gly Ala Gln Arg Leu Ala Ala Leu Gly
            405                 410                 415 gac aca gcc tgg gac ttt ggc tct att gga ggg gtc ttc aac tcc ata      1296
Asp Thr Ala Trp Asp Phe Gly Ser Ile Gly Gly Val Phe Asn Ser Ile
        420                 425                 430 gga aaa gcc gtt cac caa gtg ttt ggt ggt gcc ttc aga aca ctc ttt      1344
Gly Lys Ala Val His Gln Val Phe Gly Gly Ala Phe Arg Thr Leu Phe
    435                 440                 445 ggg gga atg tct tgg atc aca caa ggg cta atg ggt gcc cta ctg ctc      1392
Gly Gly Met Ser Trp Ile Thr Gln Gly Leu Met Gly Ala Leu Leu Leu
450                 455                 460 tgg atg ggc gtc aac gca cga gac cga tca att gct ttg gcc ttc tta      1440
Trp Met Gly Val Asn Ala Arg Asp Arg Ser Ile Ala Leu Ala Phe Leu
465                 470                 475                 480 gcc aca ggg ggt gtg ctc gtg ttc tta gcg acc aat gtg cat gct taa      1488
Ala Thr Gly Gly Val Leu Val Phe Leu Ala Thr Asn Val His Ala
            485                 490                 495

<210> SEQ ID NO 18
<211> LENGTH: 495
<212> TYPE: PRT
<213> ORGANISM: Artificial Sequence
<220> FEATURE:
<223> OTHER INFORMATION: Synthetic Construct

<400> SEQUENCE: 18

Met Arg Cys Ile Gly Met Ser Asn Arg Asp Phe Val Glu Gly Val Ser
```

```
1               5                   10                  15
Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gln Leu Phe Gly Lys Gly Gly
            100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
        130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
        210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430
```

```
Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
        450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
                485                 490                 495

<210> SEQ ID NO 19
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      L107K envelope chimera.
<220> FEATURE:
<221> NAME/KEY: CDS
<222> LOCATION: (1)..(1485)

<400> SEQUENCE: 19 atg cgt tgc ata gga atg tca aat aga gac ttt gtg gaa ggg gtt tca    48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg    96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca   144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag   192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc   240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg   288
Ser Leu Asn Glu Glu Gln Asp Lys Arg Phe Val Cys Lys His Ser Met
                85                  90                  95 gta gac aga gga tgg gga aat gga tgt gga aaa ttt gga aag gga ggc   336
Val Asp Arg Gly Trp Gly Asn Gly Cys Gly Lys Phe Gly Lys Gly Gly
                100                 105                 110 att gtg acc tgt gct atg ttc aga tgc aaa aag aac atg gaa gga aaa   384
Ile Val Thr Cys Ala Met Phe Arg Cys Lys Lys Asn Met Glu Gly Lys
            115                 120                 125 gtt gtg caa cca gaa aac ttg gaa tac acc att gtg ata aca cct cac   432
Val Val Gln Pro Glu Asn Leu Glu Tyr Thr Ile Val Ile Thr Pro His
        130                 135                 140 tca ggg gaa gag cat gca gtc gga aat gac aca gga aaa cat ggc aag   480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca   528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac   576
Gly Tyr Gly Thr Val Thr Met Glu Cys Ser Pro Arg Thr Gly Leu Asp
                180                 185                 190 ttc aat gag atg gtg ttg ttg cag atg gaa aat aaa gct tgg ctg gtg   624
Phe Asn Glu Met Val Leu Leu Gln Met Glu Asn Lys Ala Trp Leu Val
            195                 200                 205
```

| | |
|---|---|
| cac agg caa tgg ttc cta gac ctg ccg tta cca tgg ttg ccc gga gcg<br>His Arg Gln Trp Phe Leu Asp Leu Pro Leu Pro Trp Leu Pro Gly Ala<br>210                        215                    220 | 672 |
| gac aca caa ggg tca aat tgg ata cag aaa gag aca ttg gtc act ttc<br>Asp Thr Gln Gly Ser Asn Trp Ile Gln Lys Glu Thr Leu Val Thr Phe<br>225                       230                  235                 240 | 720 |
| aaa aat ccc cat gcg aag aaa cag gat gtt gtt gtt tta gga tcc caa<br>Lys Asn Pro His Ala Lys Lys Gln Asp Val Val Val Leu Gly Ser Gln<br>                       245                  250                 255 | 768 |
| gaa ggg gcc atg cac aca gca ctt aca ggg gcc aca gaa atc caa atg<br>Glu Gly Ala Met His Thr Ala Leu Thr Gly Ala Thr Glu Ile Gln Met<br>                  260                  265                  270 | 816 |
| tca tca gga aac tta ctc ttc aca gga cat ctc aag tgc agg ctg aga<br>Ser Ser Gly Asn Leu Leu Phe Thr Gly His Leu Lys Cys Arg Leu Arg<br>275                       280                  285 | 864 |
| atg gac aag cta cag ctc aaa gga atg tca tac tct atg tgc aca gga<br>Met Asp Lys Leu Gln Leu Lys Gly Met Ser Tyr Ser Met Cys Thr Gly<br>290                       295                  300 | 912 |
| aag ttt aaa gtt gtg aag gaa ata gca gaa aca caa cat gga aca ata<br>Lys Phe Lys Val Val Lys Glu Ile Ala Glu Thr Gln His Gly Thr Ile<br>305                       310                  315                 320 | 960 |
| gtt atc aga gtg caa tat gaa ggg gac ggc tct cca tgc aag atc cct<br>Val Ile Arg Val Gln Tyr Glu Gly Asp Gly Ser Pro Cys Lys Ile Pro<br>                  325                  330                 335 | 1008 |
| ttt gag ata atg gat ttg gaa aaa aga cat gtc tta ggt cgc ctg att<br>Phe Glu Ile Met Asp Leu Glu Lys Arg His Val Leu Gly Arg Leu Ile<br>                    340                  345                350 | 1056 |
| aca gtc aac cca att gtg aca gaa aaa gat agc cca gtc aac ata gaa<br>Thr Val Asn Pro Ile Val Thr Glu Lys Asp Ser Pro Val Asn Ile Glu<br>355                       360                  365 | 1104 |
| gca gaa cct cca ttc gga gac agc tac atc atc ata gga gta gag ccg<br>Ala Glu Pro Pro Phe Gly Asp Ser Tyr Ile Ile Ile Gly Val Glu Pro<br>370                       375                  380 | 1152 |
| gga caa ctg aag ctc aac tgg ttt aag aaa gga agc acg ctg ggc aag<br>Gly Gln Leu Lys Leu Asn Trp Phe Lys Lys Gly Ser Thr Leu Gly Lys<br>385                       390                  395                 400 | 1200 |
| gcc ttt tca aca act ttg aag gga gct caa aga ctg gca gcg ttg ggc<br>Ala Phe Ser Thr Thr Leu Lys Gly Ala Gln Arg Leu Ala Ala Leu Gly<br>                  405                  410                 415 | 1248 |
| gac aca gcc tgg gac ttt ggc tct att gga ggg gtc ttc aac tcc ata<br>Asp Thr Ala Trp Asp Phe Gly Ser Ile Gly Gly Val Phe Asn Ser Ile<br>                    420                  425                430 | 1296 |
| gga aaa gcc gtt cac caa gtg ttt ggt ggt gcc ttc aga aca ctc ttt<br>Gly Lys Ala Val His Gln Val Phe Gly Gly Ala Phe Arg Thr Leu Phe<br>435                       440                  445 | 1344 |
| ggg gga atg tct tgg atc aca caa ggg cta atg ggt gcc cta ctg ctc<br>Gly Gly Met Ser Trp Ile Thr Gln Gly Leu Met Gly Ala Leu Leu Leu<br>450                       455                  460 | 1392 |
| tgg atg ggc gtc aac gca cga gac cga tca att gct ttg gcc ttc tta<br>Trp Met Gly Val Asn Ala Arg Asp Arg Ser Ile Ala Leu Ala Phe Leu<br>465                       470                  475                 480 | 1440 |
| gcc aca ggg ggt gtg ctc gtg ttc tta gcg acc aat gtg cat gct taa<br>Ala Thr Gly Gly Val Leu Val Phe Leu Ala Thr Asn Val His Ala<br>                       485                  490                 495 | 1488 |

<210> SEQ ID NO 20
<211> LENGTH: 495
<212> TYPE: PRT
<213> ORGANISM: Artificial Sequence
<220> FEATURE:
<223> OTHER INFORMATION: Synthetic Construct

<400> SEQUENCE: 20

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Lys Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly

```
                        405                 410                 415
Asp Thr Ala Trp Asp Phe Gly Ser Ile Gly Gly Val Phe Asn Ser Ile
                420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
    450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
                485                 490                 495

<210> SEQ ID NO 21
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      E126A envelope chimera.
<220> FEATURE:
<221> NAME/KEY: CDS
<222> LOCATION: (1)..(1485)

<400> SEQUENCE: 21 atg cgt tgc ata gga atg tca aat aga gac ttt gtg gaa ggg gtt tca       48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg       96
Gly Gly Ser Trp Val Asp Ile Val Leu Glu His Gly Ser Cys Val Thr
            20                  25                  30 acg atg gca aaa aac aaa cca aca ttg gat ttt gaa ctg ata aaa aca      144
Thr Met Ala Lys Asn Lys Pro Thr Leu Asp Phe Glu Leu Ile Lys Thr
        35                  40                  45 gaa gcc aaa cag cct gcc acc cta agg aag tac tgt ata gag gca aag      192
Glu Ala Lys Gln Pro Ala Thr Leu Arg Lys Tyr Cys Ile Glu Ala Lys
    50                  55                  60 cta acc aac aca aca aca gaa tct cgc tgc cca aca caa ggg gaa ccc      240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg      288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc      336
Val Asp Arg Gly Trp Gly Asn Gly Cys Gly Leu Phe Gly Lys Gly Gly
            100                 105                 110 att gtg acc tgt gct atg ttc aga tgc aaa aag aac atg gca gga aaa      384
Ile Val Thr Cys Ala Met Phe Arg Cys Lys Lys Asn Met Ala Gly Lys
        115                 120                 125 gtt gtg caa cca gaa aac ttg gaa tac acc att gtg ata aca cct cac      432
Val Val Gln Pro Glu Asn Leu Glu Tyr Thr Ile Val Ile Thr Pro His
    130                 135                 140 tca ggg gaa gag cat gca gtc gga aat gac aca gga aaa cat ggc aag      480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca      528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac      576
Gly Tyr Gly Thr Val Thr Met Glu Cys Ser Pro Arg Thr Gly Leu Asp
            180                 185                 190
```

```
ttc aat gag atg gtg ttg ttg cag atg gaa aat aaa gct tgg ctg gtg      624
Phe Asn Glu Met Val Leu Leu Gln Met Glu Asn Lys Ala Trp Leu Val
        195                 200                 205 cac agg caa tgg ttc cta gac ctg ccg tta cca tgg ttg ccc gga gcg      672
His Arg Gln Trp Phe Leu Asp Leu Pro Leu Pro Trp Leu Pro Gly Ala
    210                 215                 220 gac aca caa ggg tca aat tgg ata cag aaa gag aca ttg gtc act ttc      720
Asp Thr Gln Gly Ser Asn Trp Ile Gln Lys Glu Thr Leu Val Thr Phe
225                 230                 235                 240 aaa aat ccc cat gcg aag aaa cag gat gtt gtt gtt tta gga tcc caa      768
Lys Asn Pro His Ala Lys Lys Gln Asp Val Val Val Leu Gly Ser Gln
            245                 250                 255 gaa ggg gcc atg cac aca gca ctt aca ggg gcc aca gaa atc caa atg      816
Glu Gly Ala Met His Thr Ala Leu Thr Gly Ala Thr Glu Ile Gln Met
        260                 265                 270 tca tca gga aac tta ctc ttc aca gga cat ctc aag tgc agg ctg aga      864
Ser Ser Gly Asn Leu Leu Phe Thr Gly His Leu Lys Cys Arg Leu Arg
    275                 280                 285 atg gac aag cta cag ctc aaa gga atg tca tac tct atg tgc aca gga      912
Met Asp Lys Leu Gln Leu Lys Gly Met Ser Tyr Ser Met Cys Thr Gly
290                 295                 300 aag ttt aaa gtt gtg aag gaa ata gca gaa aca caa cat gga aca ata      960
Lys Phe Lys Val Val Lys Glu Ile Ala Glu Thr Gln His Gly Thr Ile
305                 310                 315                 320 gtt atc aga gtg caa tat gaa ggg gac ggc tct cca tgc aag atc cct     1008
Val Ile Arg Val Gln Tyr Glu Gly Asp Gly Ser Pro Cys Lys Ile Pro
            325                 330                 335 ttt gag ata atg gat ttg gaa aaa aga cat gtc tta ggt cgc ctg att     1056
Phe Glu Ile Met Asp Leu Glu Lys Arg His Val Leu Gly Arg Leu Ile
        340                 345                 350 aca gtc aac cca att gtg aca gaa aaa gat agc cca gtc aac ata gaa     1104
Thr Val Asn Pro Ile Val Thr Glu Lys Asp Ser Pro Val Asn Ile Glu
    355                 360                 365 gca gaa cct cca ttc gga gac agc tac atc atc ata gga gta gag ccg     1152
Ala Glu Pro Pro Phe Gly Asp Ser Tyr Ile Ile Ile Gly Val Glu Pro
370                 375                 380 gga caa ctg aag ctc aac tgg ttt aag aaa gga agc acg ctg ggc aag     1200
Gly Gln Leu Lys Leu Asn Trp Phe Lys Lys Gly Ser Thr Leu Gly Lys
385                 390                 395                 400 gcc ttt tca aca act ttg aag gga gct caa aga ctg gca gcg ttg ggc     1248
Ala Phe Ser Thr Thr Leu Lys Gly Ala Gln Arg Leu Ala Ala Leu Gly
            405                 410                 415 gac aca gcc tgg gac ttt ggc tct att gga ggg gtc ttc aac tcc ata     1296
Asp Thr Ala Trp Asp Phe Gly Ser Ile Gly Gly Val Phe Asn Ser Ile
        420                 425                 430 gga aaa gcc gtt cac caa gtg ttt ggt ggt gcc ttc aga aca ctc ttt     1344
Gly Lys Ala Val His Gln Val Phe Gly Gly Ala Phe Arg Thr Leu Phe
    435                 440                 445 ggg gga atg tct tgg atc aca caa ggg cta atg ggt gcc cta ctg ctc     1392
Gly Gly Met Ser Trp Ile Thr Gln Gly Leu Met Gly Ala Leu Leu Leu
450                 455                 460 tgg atg ggc gtc aac gca cga gac cga tca att gct ttg gcc ttc tta     1440
Trp Met Gly Val Asn Ala Arg Asp Arg Ser Ile Ala Leu Ala Phe Leu
465                 470                 475                 480 gcc aca ggg ggt gtg ctc gtg ttc tta gcg acc aat gtg cat gct taa     1488
Ala Thr Gly Gly Val Leu Val Phe Leu Ala Thr Asn Val His Ala
            485                 490                 495

<210> SEQ ID NO 22
<211> LENGTH: 495
```

<212> TYPE: PRT
<213> ORGANISM: Artificial Sequence
<220> FEATURE:
<223> OTHER INFORMATION: Synthetic Construct

<400> SEQUENCE: 22

```
Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Ala Gly Lys
        115                 120                 125

Val Val Gln Pro Glu Asn Leu Glu Tyr Thr Ile Val Ile Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
370                 375                 380
```

```
Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
    450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
                485                 490                 495

<210> SEQ ID NO 23
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      T226N envelope chimera.
<220> FEATURE:
<221> NAME/KEY: CDS
<222> LOCATION: (1)..(1485)

<400> SEQUENCE: 23 atg cgt tgc ata gga atg tca aat aga gac ttt gtg gaa ggg gtt tca     48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg     96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca    144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag    192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc    240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg    288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc    336
Val Asp Arg Gly Trp Gly Asn Gly Cys Gly Leu Phe Gly Lys Gly Gly
                100                 105                 110 att gtg acc tgt gct atg ttc aga tgc aaa aag aac atg gaa gga aaa    384
Ile Val Thr Cys Ala Met Phe Arg Cys Lys Lys Asn Met Glu Gly Lys
            115                 120                 125 gtt gtg caa cca gaa aac ttg gaa tac acc att gtg ata aca cct cac    432
Val Val Gln Pro Glu Asn Leu Glu Tyr Thr Ile Val Ile Thr Pro His
        130                 135                 140 tca ggg gaa gag cat gca gtc gga aat gac aca gga aaa cat ggc aag    480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca    528
Glu Ile Lys Ile Thr Pro Gln Ser Ser Ile Thr Glu Ala Glu Leu Thr
                165                 170                 175
```

-continued

| | | |
|---|---|---|
| ggt tat ggc act gtc aca atg gag tgc tct cca aga acg ggc ctc gac<br>Gly Tyr Gly Thr Val Thr Met Glu Cys Ser Pro Arg Thr Gly Leu Asp<br>180 185 190 | 576 | |
| ttc aat gag atg gtg ttg ttg cag atg gaa aat aaa gct tgg ctg gtg<br>Phe Asn Glu Met Val Leu Leu Gln Met Glu Asn Lys Ala Trp Leu Val<br>195 200 205 | 624 | |
| cac agg caa tgg ttc cta gac ctg ccg tta cca tgg ttg ccc gga gcg<br>His Arg Gln Trp Phe Leu Asp Leu Pro Leu Pro Trp Leu Pro Gly Ala<br>210 215 220 | 672 | |
| gac aat caa ggg tca aat tgg ata cag aaa gag aca ttg gtc act ttc<br>Asp Asn Gln Gly Ser Asn Trp Ile Gln Lys Glu Thr Leu Val Thr Phe<br>225 230 235 240 | 720 | |
| aaa aat ccc cat gcg aag aaa cag gat gtt gtt gtt tta gga tcc caa<br>Lys Asn Pro His Ala Lys Lys Gln Asp Val Val Val Leu Gly Ser Gln<br>245 250 255 | 768 | |
| gaa ggg gcc atg cac aca gca ctt aca ggg gcc aca gaa atc caa atg<br>Glu Gly Ala Met His Thr Ala Leu Thr Gly Ala Thr Glu Ile Gln Met<br>260 265 270 | 816 | |
| tca tca gga aac tta ctc ttc aca gga cat ctc aag tgc agg ctg aga<br>Ser Ser Gly Asn Leu Leu Phe Thr Gly His Leu Lys Cys Arg Leu Arg<br>275 280 285 | 864 | |
| atg gac aag cta cag ctc aaa gga atg tca tac tct atg tgc aca gga<br>Met Asp Lys Leu Gln Leu Lys Gly Met Ser Tyr Ser Met Cys Thr Gly<br>290 295 300 | 912 | |
| aag ttt aaa gtt gtg aag gaa ata gca gaa aca caa cat gga aca ata<br>Lys Phe Lys Val Val Lys Glu Ile Ala Glu Thr Gln His Gly Thr Ile<br>305 310 315 320 | 960 | |
| gtt atc aga gtg caa tat gaa ggg gac ggc tct cca tgc aag atc cct<br>Val Ile Arg Val Gln Tyr Glu Gly Asp Gly Ser Pro Cys Lys Ile Pro<br>325 330 335 | 1008 | |
| ttt gag ata atg gat ttg gaa aaa aga cat gtc tta ggt cgc ctg att<br>Phe Glu Ile Met Asp Leu Glu Lys Arg His Val Leu Gly Arg Leu Ile<br>340 345 350 | 1056 | |
| aca gtc aac cca att gtg aca gaa aaa gat agc cca gtc aac ata gaa<br>Thr Val Asn Pro Ile Val Thr Glu Lys Asp Ser Pro Val Asn Ile Glu<br>355 360 365 | 1104 | |
| gca gaa cct cca ttc gga gac agc tac atc atc ata gga gta gag ccg<br>Ala Glu Pro Pro Phe Gly Asp Ser Tyr Ile Ile Ile Gly Val Glu Pro<br>370 375 380 | 1152 | |
| gga caa ctg aag ctc aac tgg ttt aag aaa gga agc acg ctg ggc aag<br>Gly Gln Leu Lys Leu Asn Trp Phe Lys Lys Gly Ser Thr Leu Gly Lys<br>385 390 395 400 | 1200 | |
| gcc ttt tca aca act ttg aag gga gct caa aga ctg gca gcg ttg ggc<br>Ala Phe Ser Thr Thr Leu Lys Gly Ala Gln Arg Leu Ala Ala Leu Gly<br>405 410 415 | 1248 | |
| gac aca gcc tgg gac ttt ggc tct att gga ggg gtc ttc aac tcc ata<br>Asp Thr Ala Trp Asp Phe Gly Ser Ile Gly Gly Val Phe Asn Ser Ile<br>420 425 430 | 1296 | |
| gga aaa gcc gtt cac caa gtg ttt ggt ggt gcc ttc aga aca ctc ttt<br>Gly Lys Ala Val His Gln Val Phe Gly Gly Ala Phe Arg Thr Leu Phe<br>435 440 445 | 1344 | |
| ggg gga atg tct tgg atc aca caa ggg cta atg ggt gcc cta ctg ctc<br>Gly Gly Met Ser Trp Ile Thr Gln Gly Leu Met Gly Ala Leu Leu Leu<br>450 455 460 | 1392 | |
| tgg atg ggc gtc aac gca cga gac cga tca att gct ttg gcc ttc tta<br>Trp Met Gly Val Asn Ala Arg Asp Arg Ser Ile Ala Leu Ala Phe Leu<br>465 470 475 480 | 1440 | |
| gcc aca ggg ggt gtg ctc gtg ttc tta gcg acc aat gtg cat gct taa<br>Ala Thr Gly Gly Val Leu Val Phe Leu Ala Thr Asn Val His Ala<br>485 490 495 | 1488 | |

<210> SEQ ID NO 24
<211> LENGTH: 495
<212> TYPE: PRT
<213> ORGANISM: Artificial Sequence
<220> FEATURE:
<223> OTHER INFORMATION: Synthetic Construct

<400> SEQUENCE: 24

```
Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Asn Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365
```

```
Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
    450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
                485                 490                 495

<210> SEQ ID NO 25
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      W231F envelope chimera.
<220> FEATURE:
<221> NAME/KEY: CDS
<222> LOCATION: (1)..(1485)

<400> SEQUENCE: 25 atg cgt tgc ata gga atg tca aat aga gac ttt gtg gaa ggg gtt tca      48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg      96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca     144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag     192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc     240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg     288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc     336
Val Asp Arg Gly Trp Gly Asn Gly Cys Gly Leu Phe Gly Lys Gly Gly
                100                 105                 110 att gtg acc tgt gct atg ttc aga tgc aaa aag aac atg gaa gga aaa     384
Ile Val Thr Cys Ala Met Phe Arg Cys Lys Lys Asn Met Glu Gly Lys
            115                 120                 125 gtt gtg caa cca gaa aac ttg gaa tac acc att gtg ata aca cct cac     432
Val Val Gln Pro Glu Asn Leu Glu Tyr Thr Ile Val Ile Thr Pro His
        130                 135                 140 tca ggg gaa gag cat gca gtc gga aat gac aca gga aaa cat ggc aag     480
Ser Gly Glu Glu His Ala Val Gly Asn Asp Thr Gly Lys His Gly Lys
145                 150                 155                 160
```

-continued

```
gaa atc aaa ata aca cca cag agt tcc atc aca gaa gca gaa ttg aca      528
Glu Ile Lys Ile Thr Pro Gln Ser Ser Ile Thr Glu Ala Glu Leu Thr
            165                 170                 175 ggt tat ggc act gtc aca atg gag tgc tct cca aga acg ggc ctc gac      576
Gly Tyr Gly Thr Val Thr Met Glu Cys Ser Pro Arg Thr Gly Leu Asp
        180                 185                 190 ttc aat gag atg gtg ttg ttg cag atg gaa aat aaa gct tgg ctg gtg      624
Phe Asn Glu Met Val Leu Leu Gln Met Glu Asn Lys Ala Trp Leu Val
    195                 200                 205 cac agg caa tgg ttc cta gac ctg ccg tta cca tgg ttg ccc gga gcg      672
His Arg Gln Trp Phe Leu Asp Leu Pro Leu Pro Trp Leu Pro Gly Ala
210                 215                 220 gac aca caa ggg tca aat ttc ata cag aaa gag aca ttg gtc act ttc      720
Asp Thr Gln Gly Ser Asn Phe Ile Gln Lys Glu Thr Leu Val Thr Phe
225                 230                 235                 240 aaa aat ccc cat gcg aag aaa cag gat gtt gtt gtt tta gga tcc caa      768
Lys Asn Pro His Ala Lys Lys Gln Asp Val Val Val Leu Gly Ser Gln
            245                 250                 255 gaa ggg gcc atg cac aca gca ctt aca ggg gcc aca gaa atc caa atg      816
Glu Gly Ala Met His Thr Ala Leu Thr Gly Ala Thr Glu Ile Gln Met
        260                 265                 270 tca tca gga aac tta ctc ttc aca gga cat ctc aag tgc agg ctg aga      864
Ser Ser Gly Asn Leu Leu Phe Thr Gly His Leu Lys Cys Arg Leu Arg
    275                 280                 285 atg gac aag cta cag ctc aaa gga atg tca tac tct atg tgc aca gga      912
Met Asp Lys Leu Gln Leu Lys Gly Met Ser Tyr Ser Met Cys Thr Gly
290                 295                 300 aag ttt aaa gtt gtg aag gaa ata gca gaa aca caa cat gga aca ata      960
Lys Phe Lys Val Val Lys Glu Ile Ala Glu Thr Gln His Gly Thr Ile
305                 310                 315                 320 gtt atc aga gtg caa tat gaa ggg gac ggc tct cca tgc aag atc cct     1008
Val Ile Arg Val Gln Tyr Glu Gly Asp Gly Ser Pro Cys Lys Ile Pro
            325                 330                 335 ttt gag ata atg gat ttg gaa aaa aga cat gtc tta ggt cgc ctg att     1056
Phe Glu Ile Met Asp Leu Glu Lys Arg His Val Leu Gly Arg Leu Ile
        340                 345                 350 aca gtc aac cca att gtg aca gaa aaa gat agc cca gtc aac ata gaa     1104
Thr Val Asn Pro Ile Val Thr Glu Lys Asp Ser Pro Val Asn Ile Glu
    355                 360                 365 gca gaa cct cca ttc gga gac agc tac atc atc ata gga gta gag ccg     1152
Ala Glu Pro Pro Phe Gly Asp Ser Tyr Ile Ile Ile Gly Val Glu Pro
370                 375                 380 gga caa ctg aag ctc aac tgg ttt aag aaa gga agc acg ctg ggc aag     1200
Gly Gln Leu Lys Leu Asn Trp Phe Lys Lys Gly Ser Thr Leu Gly Lys
385                 390                 395                 400 gcc ttt tca aca act ttg aag gga gct caa aga ctg gca gcg ttg ggc     1248
Ala Phe Ser Thr Thr Leu Lys Gly Ala Gln Arg Leu Ala Ala Leu Gly
            405                 410                 415 gac aca gcc tgg gac ttt ggc tct att gga ggg gtc ttc aac tcc ata     1296
Asp Thr Ala Trp Asp Phe Gly Ser Ile Gly Gly Val Phe Asn Ser Ile
        420                 425                 430 gga aaa gcc gtt cac caa gtg ttt ggt ggt gcc ttc aga aca ctc ttt     1344
Gly Lys Ala Val His Gln Val Phe Gly Gly Ala Phe Arg Thr Leu Phe
    435                 440                 445 ggg gga atg tct tgg atc aca caa ggg cta atg ggt gcc cta ctg ctc     1392
Gly Gly Met Ser Trp Ile Thr Gln Gly Leu Met Gly Ala Leu Leu Leu
450                 455                 460 tgg atg ggc gtc aac gca cga gac cga tca att gct ttg gcc ttc tta     1440
Trp Met Gly Val Asn Ala Arg Asp Arg Ser Ile Ala Leu Ala Phe Leu
465                 470                 475                 480
```

```
gcc aca ggg ggt gtg ctc gtg ttc tta gcg acc aat gtg cat gct taa    1488
Ala Thr Gly Gly Val Leu Val Phe Leu Ala Thr Asn Val His Ala
                485                 490                 495
```

<210> SEQ ID NO 26
<211> LENGTH: 495
<212> TYPE: PRT
<213> ORGANISM: Artificial Sequence
<220> FEATURE:
<223> OTHER INFORMATION: Synthetic Construct

<400> SEQUENCE: 26

```
Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
                180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
    210                 215                 220

Asp Thr Gln Gly Ser Asn Phe Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
```

```
                340              345              350
Thr Val Asn Pro Ile Val Thr Glu Lys Asp Ser Pro Val Asn Ile Glu
                355              360              365

Ala Glu Pro Pro Phe Gly Asp Ser Tyr Ile Ile Ile Gly Val Glu Pro
            370              375              380

Gly Gln Leu Lys Leu Asn Trp Phe Lys Lys Gly Ser Thr Leu Gly Lys
385              390              395              400

Ala Phe Ser Thr Thr Leu Lys Gly Ala Gln Arg Leu Ala Ala Leu Gly
                405              410              415

Asp Thr Ala Trp Asp Phe Gly Ser Ile Gly Gly Val Phe Asn Ser Ile
            420              425              430

Gly Lys Ala Val His Gln Val Phe Gly Gly Ala Phe Arg Thr Leu Phe
            435              440              445

Gly Gly Met Ser Trp Ile Thr Gln Gly Leu Met Gly Ala Leu Leu Leu
            450              455              460

Trp Met Gly Val Asn Ala Arg Asp Arg Ser Ile Ala Leu Ala Phe Leu
465              470              475              480

Ala Thr Gly Gly Val Leu Val Phe Leu Ala Thr Asn Val His Ala
                485              490              495

<210> SEQ ID NO 27
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      W231L envelope chimera.
<220> FEATURE:
<221> NAME/KEY: CDS
<222> LOCATION: (1)..(1485)

<400> SEQUENCE: 27 atg cgt tgc ata gga atg tca aat aga gac ttt gtg gaa ggg gtt tca     48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg     96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca    144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag    192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc    240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg    288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc    336
Val Asp Arg Gly Trp Gly Asn Gly Cys Gly Leu Phe Gly Lys Gly Gly
                100                 105                 110 att gtg acc tgt gct atg ttc aga tgc aaa aag aac atg gaa gga aaa    384
Ile Val Thr Cys Ala Met Phe Arg Cys Lys Lys Asn Met Glu Gly Lys
            115                 120                 125 gtt gtg caa cca gaa aac ttg gaa tac acc att gtg ata aca cct cac    432
Val Val Gln Pro Glu Asn Leu Glu Tyr Thr Ile Val Ile Thr Pro His
        130                 135                 140
```

```
tca ggg gaa gag cat gca gtc gga aat gac aca gga aaa cat ggc aag      480
Ser Gly Glu Glu His Ala Val Gly Asn Asp Thr Gly Lys His Gly Lys
145                 150                 155                 160 gaa atc aaa ata aca cca cag agt tcc atc aca gaa gca gaa ttg aca      528
Glu Ile Lys Ile Thr Pro Gln Ser Ser Ile Thr Glu Ala Glu Leu Thr
                165                 170                 175 ggt tat ggc act gtc aca atg gag tgc tct cca aga acg ggc ctc gac      576
Gly Tyr Gly Thr Val Thr Met Glu Cys Ser Pro Arg Thr Gly Leu Asp
            180                 185                 190 ttc aat gag atg gtg ttg ttg cag atg gaa aat aaa gct tgg ctg gtg      624
Phe Asn Glu Met Val Leu Leu Gln Met Glu Asn Lys Ala Trp Leu Val
        195                 200                 205 cac agg caa tgg ttc cta gac ctg ccg tta cca tgg ttg ccc gga gcg      672
His Arg Gln Trp Phe Leu Asp Leu Pro Leu Pro Trp Leu Pro Gly Ala
    210                 215                 220 gac aca caa ggg tca aat ctg ata cag aaa gag aca ttg gtc act ttc      720
Asp Thr Gln Gly Ser Asn Leu Ile Gln Lys Glu Thr Leu Val Thr Phe
225                 230                 235                 240 aaa aat ccc cat gcg aag aaa cag gat gtt gtt gtt tta gga tcc caa      768
Lys Asn Pro His Ala Lys Lys Gln Asp Val Val Val Leu Gly Ser Gln
                245                 250                 255 gaa ggg gcc atg cac aca gca ctt aca ggg gcc aca gaa atc caa atg      816
Glu Gly Ala Met His Thr Ala Leu Thr Gly Ala Thr Glu Ile Gln Met
            260                 265                 270 tca tca gga aac tta ctc ttc aca gga cat ctc aag tgc agg ctg aga      864
Ser Ser Gly Asn Leu Leu Phe Thr Gly His Leu Lys Cys Arg Leu Arg
        275                 280                 285 atg gac aag cta cag ctc aaa gga atg tca tac tct atg tgc aca gga      912
Met Asp Lys Leu Gln Leu Lys Gly Met Ser Tyr Ser Met Cys Thr Gly
    290                 295                 300 aag ttt aaa gtt gtg aag gaa ata gca gaa aca caa cat gga aca ata      960
Lys Phe Lys Val Val Lys Glu Ile Ala Glu Thr Gln His Gly Thr Ile
305                 310                 315                 320 gtt atc aga gtg caa tat gaa ggg gac ggc tct cca tgc aag atc cct     1008
Val Ile Arg Val Gln Tyr Glu Gly Asp Gly Ser Pro Cys Lys Ile Pro
                325                 330                 335 ttt gag ata atg gat ttg gaa aaa aga cat gtc tta ggt cgc ctg att     1056
Phe Glu Ile Met Asp Leu Glu Lys Arg His Val Leu Gly Arg Leu Ile
            340                 345                 350 aca gtc aac cca att gtg aca gaa aaa gat agc cca gtc aac ata gaa     1104
Thr Val Asn Pro Ile Val Thr Glu Lys Asp Ser Pro Val Asn Ile Glu
        355                 360                 365 gca gaa cct cca ttc gga gac agc tac atc atc ata gga gta gag ccg     1152
Ala Glu Pro Pro Phe Gly Asp Ser Tyr Ile Ile Ile Gly Val Glu Pro
    370                 375                 380 gga caa ctg aag ctc aac tgg ttt aag aaa gga agc acg ctg ggc aag     1200
Gly Gln Leu Lys Leu Asn Trp Phe Lys Lys Gly Ser Thr Leu Gly Lys
385                 390                 395                 400 gcc ttt tca aca act ttg aag gga gct caa aga ctg gca gcg ttg ggc     1248
Ala Phe Ser Thr Thr Leu Lys Gly Ala Gln Arg Leu Ala Ala Leu Gly
                405                 410                 415 gac aca gcc tgg gac ttt ggc tct att gga ggg gtc ttc aac tcc ata     1296
Asp Thr Ala Trp Asp Phe Gly Ser Ile Gly Gly Val Phe Asn Ser Ile
            420                 425                 430 gga aaa gcc gtt cac caa gtg ttt ggt ggt gcc ttc aga aca ctc ttt     1344
Gly Lys Ala Val His Gln Val Phe Gly Gly Ala Phe Arg Thr Leu Phe
        435                 440                 445 ggg gga atg tct tgg atc aca caa ggg cta atg ggt gcc cta ctg ctc     1392
Gly Gly Met Ser Trp Ile Thr Gln Gly Leu Met Gly Ala Leu Leu Leu
    450                 455                 460
```

-continued

```
tgg atg ggc gtc aac gca cga gac cga tca att gct ttg gcc ttc tta    1440
Trp Met Gly Val Asn Ala Arg Asp Arg Ser Ile Ala Leu Ala Phe Leu
465                 470                 475                 480 gcc aca ggg ggt gtg ctc gtg ttc tta gcg acc aat gtg cat gct taa    1488
Ala Thr Gly Gly Val Leu Val Phe Leu Ala Thr Asn Val His Ala
                485                 490                 495
```

<210> SEQ ID NO 28
<211> LENGTH: 495
<212> TYPE: PRT
<213> ORGANISM: Artificial Sequence
<220> FEATURE:
<223> OTHER INFORMATION: Synthetic Construct

<400> SEQUENCE: 28

```
Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
        50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
        130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
                180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
        210                 215                 220

Asp Thr Gln Gly Ser Asn Leu Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320
```

-continued

```
Val Ile Arg Val Gln Tyr Glu Gly Asp Gly Ser Pro Cys Lys Ile Pro
            325                 330                 335

Phe Glu Ile Met Asp Leu Glu Lys Arg His Val Leu Gly Arg Leu Ile
        340                 345                 350

Thr Val Asn Pro Ile Val Thr Glu Lys Asp Ser Pro Val Asn Ile Glu
    355                 360                 365

Ala Glu Pro Pro Phe Gly Asp Ser Tyr Ile Ile Ile Gly Val Glu Pro
370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
            405                 410                 415

Asp Thr Ala Trp Asp Phe Gly Ser Ile Gly Gly Val Phe Asn Ser Ile
        420                 425                 430

Gly Lys Ala Val His Gln Val Phe Gly Ala Phe Arg Thr Leu Phe
    435                 440                 445

Gly Gly Met Ser Trp Ile Thr Gln Gly Leu Met Gly Ala Leu Leu Leu
    450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
            485                 490                 495

<210> SEQ ID NO 29
<211> LENGTH: 1488
<212> TYPE: DNA
<213> ORGANISM: Artificial Sequence
<220> FEATURE:
<223> OTHER INFORMATION: Dengue virus-2/Japanese encephalitis virus
      E126A/T226N envelope chimera.
<220> FEATURE:
<221> NAME/KEY: CDS
<222> LOCATION: (1)..(1485)

<400> SEQUENCE: 29 atg cgt tgc ata gga atg tca aat aga gac ttt gtg gaa ggg gtt tca      48
Met Arg Cys Ile Gly Met Ser Asn Arg Asp Phe Val Glu Gly Val Ser
1               5                   10                  15 gga gga agc tgg gtt gac ata gtc tta gaa cat ggg agc tgt gtg acg      96
Gly Gly Ser Trp Val Asp Ile Val Leu Glu His Gly Ser Cys Val Thr
                20                  25                  30 acg atg gca aaa aac aaa cca aca ttg gat ttt gaa ctg ata aaa aca     144
Thr Met Ala Lys Asn Lys Pro Thr Leu Asp Phe Glu Leu Ile Lys Thr
            35                  40                  45 gaa gcc aaa cag cct gcc acc cta agg aag tac tgt ata gag gca aag     192
Glu Ala Lys Gln Pro Ala Thr Leu Arg Lys Tyr Cys Ile Glu Ala Lys
        50                  55                  60 cta acc aac aca aca aca gaa tct cgc tgc cca aca caa ggg gaa ccc     240
Leu Thr Asn Thr Thr Thr Glu Ser Arg Cys Pro Thr Gln Gly Glu Pro
65                  70                  75                  80 agc cta aat gaa gag cag gac aaa agg ttc gtc tgc aaa cac tcc atg     288
Ser Leu Asn Glu Glu Gln Asp Lys Arg Phe Val Cys Lys His Ser Met
                85                  90                  95 gta gac aga gga tgg gga aat gga tgt gga cta ttt gga aag gga ggc     336
Val Asp Arg Gly Trp Gly Asn Gly Cys Gly Leu Phe Gly Lys Gly Gly
                100                 105                 110 att gtg acc tgt gct atg ttc aga tgc aaa aag aac atg gca gga aaa     384
Ile Val Thr Cys Ala Met Phe Arg Cys Lys Lys Asn Met Ala Gly Lys
            115                 120                 125
```

```
gtt gtg caa cca gaa aac ttg gaa tac acc att gtg ata aca cct cac     432
Val Val Gln Pro Glu Asn Leu Glu Tyr Thr Ile Val Ile Thr Pro His
    130             135             140 tca ggg gaa gag cat gca gtc gga aat gac aca gga aaa cat ggc aag     480
Ser Gly Glu Glu His Ala Val Gly Asn Asp Thr Gly Lys His Gly Lys
145             150             155             160 gaa atc aaa ata aca cca cag agt tcc atc aca gaa gca gaa ttg aca     528
Glu Ile Lys Ile Thr Pro Gln Ser Ser Ile Thr Glu Ala Glu Leu Thr
            165             170             175 ggt tat ggc act gtc aca atg gag tgc tct cca aga acg ggc ctc gac     576
Gly Tyr Gly Thr Val Thr Met Glu Cys Ser Pro Arg Thr Gly Leu Asp
        180             185             190 ttc aat gag atg gtg ttg ttg cag atg gaa aat aaa gct tgg ctg gtg     624
Phe Asn Glu Met Val Leu Leu Gln Met Glu Asn Lys Ala Trp Leu Val
    195             200             205 cac agg caa tgg ttc cta gac ctg ccg tta cca tgg ttg ccc gga gcg     672
His Arg Gln Trp Phe Leu Asp Leu Pro Leu Pro Trp Leu Pro Gly Ala
210             215             220 gac aat caa ggg tca aat tgg ata cag aaa gag aca ttg gtc act ttc     720
Asp Asn Gln Gly Ser Asn Trp Ile Gln Lys Glu Thr Leu Val Thr Phe
225             230             235             240 aaa aat ccc cat gcg aag aaa cag gat gtt gtt gtt tta gga tcc caa     768
Lys Asn Pro His Ala Lys Lys Gln Asp Val Val Val Leu Gly Ser Gln
            245             250             255 gaa ggg gcc atg cac aca gca ctt aca ggg gcc aca gaa atc caa atg     816
Glu Gly Ala Met His Thr Ala Leu Thr Gly Ala Thr Glu Ile Gln Met
        260             265             270 tca tca gga aac tta ctc ttc aca gga cat ctc aag tgc agg ctg aga     864
Ser Ser Gly Asn Leu Leu Phe Thr Gly His Leu Lys Cys Arg Leu Arg
    275             280             285 atg gac aag cta cag ctc aaa gga atg tca tac tct atg tgc aca gga     912
Met Asp Lys Leu Gln Leu Lys Gly Met Ser Tyr Ser Met Cys Thr Gly
290             295             300 aag ttt aaa gtt gtg aag gaa ata gca gaa aca caa cat gga aca ata     960
Lys Phe Lys Val Val Lys Glu Ile Ala Glu Thr Gln His Gly Thr Ile
305             310             315             320 gtt atc aga gtg caa tat gaa ggg gac ggc tct cca tgc aag atc cct    1008
Val Ile Arg Val Gln Tyr Glu Gly Asp Gly Ser Pro Cys Lys Ile Pro
            325             330             335 ttt gag ata atg gat ttg gaa aaa aga cat gtc tta ggt cgc ctg att    1056
Phe Glu Ile Met Asp Leu Glu Lys Arg His Val Leu Gly Arg Leu Ile
        340             345             350 aca gtc aac cca att gtg aca gaa aaa gat agc cca gtc aac ata gaa    1104
Thr Val Asn Pro Ile Val Thr Glu Lys Asp Ser Pro Val Asn Ile Glu
    355             360             365 gca gaa cct cca ttc gga gac agc tac atc atc ata gga gta gag ccg    1152
Ala Glu Pro Pro Phe Gly Asp Ser Tyr Ile Ile Ile Gly Val Glu Pro
370             375             380 gga caa ctg aag ctc aac tgg ttt aag aaa gga agc acg ctg ggc aag    1200
Gly Gln Leu Lys Leu Asn Trp Phe Lys Lys Gly Ser Thr Leu Gly Lys
385             390             395             400 gcc ttt tca aca act ttg aag gga gct caa aga ctg gca gcg ttg ggc    1248
Ala Phe Ser Thr Thr Leu Lys Gly Ala Gln Arg Leu Ala Ala Leu Gly
            405             410             415 gac aca gcc tgg gac ttt ggc tct att gga ggg gtc ttc aac tcc ata    1296
Asp Thr Ala Trp Asp Phe Gly Ser Ile Gly Gly Val Phe Asn Ser Ile
        420             425             430 gga aaa gcc gtt cac caa gtg ttt ggt ggt gcc ttc aga aca ctc ttt    1344
Gly Lys Ala Val His Gln Val Phe Gly Gly Ala Phe Arg Thr Leu Phe
    435             440             445
```

```
ggg gga atg tct tgg atc aca caa ggg cta atg ggt gcc cta ctg ctc    1392
Gly Gly Met Ser Trp Ile Thr Gln Gly Leu Met Gly Ala Leu Leu Leu
450                 455                 460 tgg atg ggc gtc aac gca cga gac cga tca att gct ttg gcc ttc tta    1440
Trp Met Gly Val Asn Ala Arg Asp Arg Ser Ile Ala Leu Ala Phe Leu
465                 470                 475                 480 gcc aca ggg ggt gtc ctc gtg ttc tta gcg acc aat gtg cat gct taa    1488
Ala Thr Gly Gly Val Leu Val Phe Leu Ala Thr Asn Val His Ala
                485                 490                 495

<210> SEQ ID NO 30
<211> LENGTH: 495
<212> TYPE: PRT
<213> ORGANISM: Artificial Sequence
<220> FEATURE:
<223> OTHER INFORMATION: Synthetic Construct

<400> SEQUENCE: 30

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Arg Cys Lys Lys Asn Met Ala Gly Lys
            115                 120                 125

Val Val Gln Pro Glu Asn Leu Glu Tyr Thr Ile Val Ile Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Asn Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300
```

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Gly Val Glu Pro
    370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
450                 455                 460

Trp Met Gly Val Asn Ala Arg Asp Arg Ser Ile Ala Leu Ala Phe Leu
465                 470                 475                 480

Ala Thr Gly Gly Val Leu Val Phe Leu Ala Thr Asn Val His Ala
                485                 490                 495

<210> SEQ ID NO 31
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 31
ctcccttttc caaacagacc acagtggtta ccccatccgc                    40

<210> SEQ ID NO 32
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 32
ctcccttttc caaacagacc acagttgtta ccccatccgc                    40

<210> SEQ ID NO 33
<211> LENGTH: 38
<212> TYPE: DNA
<213> ORGANISM: Artificial Sequence
<220> FEATURE:
<223> OTHER INFORMATION: Mutagenic oligonucleotide primer.

<400> SEQUENCE: 33
cccttttcca aacagaccac agtcgttacc ccatccgc                      38

<210> SEQ ID NO 34
<211> LENGTH: 40
<212> TYPE: DNA
<213> ORGANISM: Artificial Sequence
<220> FEATURE:

<223> OTHER INFORMATION: Mutagenic oligonucleotide primer.

<400> SEQUENCE: 34
ctcccttttc caaacagacc acacttgtta ccccatccgc                                    40

<210> SEQ ID NO 35
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 35
ctcccttttc caaacagctg acatccgtta ccccatccgc                                    40

<210> SEQ ID NO 36
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 36
ctcccttttc caaacagctt acatccgtta ccccatccgc                                    40

<210> SEQ ID NO 37
<211> LENGTH: 39
<212> TYPE: DNA
<213> ORGANISM: Artificial Sequence
<220> FEATURE:
<223> OTHER INFORMATION: Mutagenic oligonucleotide primer.

<400> SEQUENCE: 37
tcccttttcc aaacagtaca catccgttac cccatccgc                                     39

<210> SEQ ID NO 38
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 38
cttttccaaa cagatcacat ccgttacccc atccgc                                        36

<210> SEQ ID NO 39
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 39
ctcccttttc caaagaaacc acatccgtta ccccatccgc                                    40

<210> SEQ ID NO 40
<211> LENGTH: 44
<212> TYPE: DNA
<213> ORGANISM: Artificial Sequence
<220> FEATURE:
<223> OTHER INFORMATION: Mutagenic oligonucleotide primer.

<400> SEQUENCE: 40
aatgctccct tttccaaaga actgacatcc gttaccccat ccgc                               44

```
<210> SEQ ID NO 41
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 41
cgggcttatg gtgaattgag ccgcttggtt ttttcc                              36

<210> SEQ ID NO 42
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 42
ttccatactc gcccatgttg gcaataaagg acggtg                              36

<210> SEQ ID NO 43
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 43
gtaactgttc catactcgga catgttggcc gtaaagg                             37

<210> SEQ ID NO 44
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 44
gtaactgttc catagttgcc catgttggcc gtaaagg                             37

<210> SEQ ID NO 45
<211> LENGTH: 35
<212> TYPE: DNA
<213> ORGANISM: Artificial Sequence
<220> FEATURE:
<223> OTHER INFORMATION: Mutagenic oligonucleotide primer.

<400> SEQUENCE: 45
ctctgttgcg ccaatcgttt gtggcagggc tcgtc                               35

<210> SEQ ID NO 46
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 46
ttctctgttg cggaaatcag ttgtggcagg gctcgtc                             37

<210> SEQ ID NO 47
<211> LENGTH: 33
<212> TYPE: DNA
<213> ORGANISM: Artificial Sequence
<220> FEATURE:
<223> OTHER INFORMATION: Mutagenic oligonucleotide primer.
```

<400> SEQUENCE: 47
tactacagtt tgcttggtgg cacgcggttc ctc                          33

<210> SEQ ID NO 48
<211> LENGTH: 36
<212> TYPE: DNA
<213> ORGANISM: Artificial Sequence
<220> FEATURE:
<223> OTHER INFORMATION: Mutagenic oligonucleotide primer.

<400> SEQUENCE: 48
tgattgcaag gttagggttg atccgctaac agtggc                       36

<210> SEQ ID NO 49
<211> LENGTH: 38
<212> TYPE: DNA
<213> ORGANISM: Artificial Sequence
<220> FEATURE:
<223> OTHER INFORMATION: Mutagenic oligonucleotide primer.

<400> SEQUENCE: 49
cgttcccttg attttgacgt agtcaagctt agctctgc                     38

<210> SEQ ID NO 50
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 50
acacatgcca tatgccgttc ccttgatttt gacc                         34

<210> SEQ ID NO 51
<211> LENGTH: 35
<212> TYPE: DNA
<213> ORGANISM: Artificial Sequence
<220> FEATURE:
<223> OTHER INFORMATION: Mutagenic oligonucleotide primer.

<400> SEQUENCE: 51
cagggtccgt tgcttccatc atactgcagt tccac                        35

<210> SEQ ID NO 52
<211> LENGTH: 33
<212> TYPE: DNA
<213> ORGANISM: Artificial Sequence
<220> FEATURE:
<223> OTHER INFORMATION: Mutagenic oligonucleotide primer.

<400> SEQUENCE: 52
cgatcatgac cttgttgttc gatccccctg tgc                          33

<210> SEQ ID NO 53
<211> LENGTH: 35
<212> TYPE: DNA
<213> ORGANISM: Artificial Sequence
<220> FEATURE:
<223> OTHER INFORMATION: Mutagenic oligonucleotide primer.

<400> SEQUENCE: 53
ttcgatcatg accttgttga acgctccccc tgtgc                        35

<210> SEQ ID NO 54
<211> LENGTH: 35

```
<212> TYPE: DNA
<213> ORGANISM: Artificial Sequence
<220> FEATURE:
<223> OTHER INFORMATION: Mutagenic oligonucleotide primer.

<400> SEQUENCE: 54
tttgccaaat agtccgcagt tgttgcccca gcccc                        35

<210> SEQ ID NO 55
<211> LENGTH: 31
<212> TYPE: DNA
<213> ORGANISM: Artificial Sequence
<220> FEATURE:
<223> OTHER INFORMATION: Mutagenic oligonucleotide primer.

<400> SEQUENCE: 55
ttgccaaata gtccgcagtc gttgccccag c                            31

<210> SEQ ID NO 56
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 56
cctttgccaa atagtccgca cttgttgccc cagcccc                      37

<210> SEQ ID NO 57
<211> LENGTH: 31
<212> TYPE: DNA
<213> ORGANISM: Artificial Sequence
<220> FEATURE:
<223> OTHER INFORMATION: Mutagenic oligonucleotide primer.

<400> SEQUENCE: 57
ttgccaaata gtccgcatgc gttgccccag c                            31

<210> SEQ ID NO 58
<211> LENGTH: 33
<212> TYPE: DNA
<213> ORGANISM: Artificial Sequence
<220> FEATURE:
<223> OTHER INFORMATION: Mutagenic oligonucleotide primer.

<400> SEQUENCE: 58
tttgccaaat aggacgcagc cgttgcccca gcc                          33

<210> SEQ ID NO 59
<211> LENGTH: 33
<212> TYPE: DNA
<213> ORGANISM: Artificial Sequence
<220> FEATURE:
<223> OTHER INFORMATION: Mutagenic oligonucleotide primer.

<400> SEQUENCE: 59
tttgccaaat agcctgcagc cgttgcccca gcc                          33

<210> SEQ ID NO 60
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 60
```
cctttgccaa ataggtagca gccgttgccc cagcccc                                37

<210> SEQ ID NO 61
<211> LENGTH: 33
<212> TYPE: DNA
<213> ORGANISM: Artificial Sequence
<220> FEATURE:
<223> OTHER INFORMATION: Mutagenic oligonucleotide primer.

<400> SEQUENCE: 61
tttgccaaat agagcgcagc cgttgcccca gcc                                    33

<210> SEQ ID NO 62
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 62
ttcctttgcc aaagtatccg cagccgttgc cccagcc                                37

<210> SEQ ID NO 63
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 63
cctttgccaa agaatccgca gccgttgccc cagc                                   34

<210> SEQ ID NO 64
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 64
cctttgccaa aatgtccgca gccgttgccc cagc                                   34

<210> SEQ ID NO 65
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 65
cctttgccaa atcttccgca gccgttgccc cagc                                   34

<210> SEQ ID NO 66
<211> LENGTH: 33
<212> TYPE: DNA
<213> ORGANISM: Artificial Sequence
<220> FEATURE:
<223> OTHER INFORMATION: Mutagenic oligonucleotide primer.

<400> SEQUENCE: 66
cttggtagag caggcaaata cggcgcatgt gtc                                    33

<210> SEQ ID NO 67
<211> LENGTH: 30
<212> TYPE: DNA
<213> ORGANISM: Artificial Sequence
<220> FEATURE:
<223> OTHER INFORMATION: Mutagenic oligonucleotide primer.

<400> SEQUENCE: 67
ccaacctgtg tggagtagtc tccgtgcgac    30

<210> SEQ ID NO 68
<211> LENGTH: 32
<212> TYPE: DNA
<213> ORGANISM: Artificial Sequence
<220> FEATURE:
<223> OTHER INFORMATION: Mutagenic oligonucleotide primer.

<400> SEQUENCE: 68
ccaacctgtg tggagccgtt tccgtgcgac tc    32

<210> SEQ ID NO 69
<211> LENGTH: 38
<212> TYPE: DNA
<213> ORGANISM: Artificial Sequence
<220> FEATURE:
<223> OTHER INFORMATION: Mutagenic oligonucleotide primer.

<400> SEQUENCE: 69
ctgagtggct ccaacatctg tggagtagtt tccgtgcg    38

<210> SEQ ID NO 70
<211> LENGTH: 32
<212> TYPE: DNA
<213> ORGANISM: Artificial Sequence
<220> FEATURE:
<223> OTHER INFORMATION: Mutagenic oligonucleotide primer.

<400> SEQUENCE: 70
aggagtgatg ctgaagtacc ctgcctgagt gg    32

<210> SEQ ID NO 71
<211> LENGTH: 34
<212> TYPE: DNA
<213> ORGANISM: Artificial Sequence
<220> FEATURE:
<223> OTHER INFORMATION: Mutagenic oligonucleotide primer.

<400> SEQUENCE: 71
ccaagcttta gtacgtatga aggcgccgca ggag    34

<210> SEQ ID NO 72
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 72
cctctccata gcctccaagc tttagtgtgt atgaagg    37

<210> SEQ ID NO 73
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 73
aacgtctctc tgttcctgaa cacagtactt ccagcac    37

-continued

<210> SEQ ID NO 74
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 74
ccgacgtcaa cttgacagtg ttgtctgaaa attccacagg                          40

<210> SEQ ID NO 75
<211> LENGTH: 39
<212> TYPE: DNA
<213> ORGANISM: Artificial Sequence
<220> FEATURE:
<223> OTHER INFORMATION: Mutagenic oligonucleotide primer.

<400> SEQUENCE: 75
gttcccttca actgcaagtt ttccatcttc actctacac                           39

<210> SEQ ID NO 76
<211> LENGTH: 40
<212> TYPE: DNA
<213> ORGANISM: Artificial Sequence
<220> FEATURE:
<223> OTHER INFORMATION: Mutagenic oligonucleotide primer.

<400> SEQUENCE: 76
acagacgcca tagtttgttc ccttcaactg caattttttcc                         40

<210> SEQ ID NO 77
<211> LENGTH: 37
<212> TYPE: DNA
<213> ORGANISM: Artificial Sequence
<220> FEATURE:
<223> OTHER INFORMATION: Mutagenic oligonucleotide primer.

<400> SEQUENCE: 77
ccatccgtgc cgttgtactg caattccaac accacag                             37

<210> SEQ ID NO 78
<211> LENGTH: 31
<212> TYPE: DNA
<213> ORGANISM: Artificial Sequence
<220> FEATURE:
<223> OTHER INFORMATION: Mutagenic oligonucleotide primer.

<400> SEQUENCE: 78
ggaccttagc gttgaccgtg gccactgaaa c                                   31

<210> SEQ ID NO 79
<211> LENGTH: 29
<212> TYPE: DNA
<213> ORGANISM: Artificial Sequence
<220> FEATURE:
<223> OTHER INFORMATION: Mutagenic oligonucleotide primer.

<400> SEQUENCE: 79
accttagcgc tggccgtggc cactgaaac                                      29

<210> SEQ ID NO 80
<211> LENGTH: 1506
<212> TYPE: DNA
<213> ORGANISM: Artificial Sequence
<220> FEATURE:
<223> OTHER INFORMATION: St. Louis encephalitis virus/Japanese

```
      encephalitis virus envelope chimera.
<220> FEATURE:
<221> NAME/KEY: CDS
<222> LOCATION: (1)..(1503)
<220> FEATURE:
<221> NAME/KEY: misc_feature
<222> LOCATION: (316)..(318)
<223> OTHER INFORMATION: Mutagenesis of GGT codon to CAG codon produces
      a G106Q substitution.

<400> SEQUENCE: 80 ttc aac tgt ctg gga aca tca aac agg gac ttt gtc gag gga gcc agt        48
Phe Asn Cys Leu Gly Thr Ser Asn Arg Asp Phe Val Glu Gly Ala Ser
1               5                   10                  15 ggg gca aca tgg att gac ttg gta ctt gaa ggg gga agc tgt gtc aca        96
Gly Ala Thr Trp Ile Asp Leu Val Leu Glu Gly Gly Ser Cys Val Thr
            20                  25                  30 gtg atg gca cca gag aaa cca aca ctg gac ttc aaa gtg atg aag atg       144
Val Met Ala Pro Glu Lys Pro Thr Leu Asp Phe Lys Val Met Lys Met
        35                  40                  45 gag gct acc gag tta gcc act gtg cgt gag tat tgt tac gaa gca acc       192
Glu Ala Thr Glu Leu Ala Thr Val Arg Glu Tyr Cys Tyr Glu Ala Thr
    50                  55                  60 ttg gac acg ctg tca aca gtg gca agg tgc ccc aca aca gga gaa gct       240
Leu Asp Thr Leu Ser Thr Val Ala Arg Cys Pro Thr Thr Gly Glu Ala
65                  70                  75                  80 cac aac acc aaa agg agt gac cca aca ttt gtc tgc aaa aga gat gtt       288
His Asn Thr Lys Arg Ser Asp Pro Thr Phe Val Cys Lys Arg Asp Val
                85                  90                  95 gtg gac cgc gga tgg ggt aac gga tgt ggt ctg ttt gga aaa ggg agc       336
Val Asp Arg Gly Trp Gly Asn Gly Cys Gly Leu Phe Gly Lys Gly Ser
            100                 105                 110 att gac aca tgc gct aag ttc aca tgc aaa aac aag gca aca ggg aag       384
Ile Asp Thr Cys Ala Lys Phe Thr Cys Lys Asn Lys Ala Thr Gly Lys
        115                 120                 125 acg atc ttg aga gaa aac atc aag tat gag gtt gca atc ttt gtg cat       432
Thr Ile Leu Arg Glu Asn Ile Lys Tyr Glu Val Ala Ile Phe Val His
    130                 135                 140 ggt tca acg gac tct acg tca cat ggc aat tac ttt gag cag att gga       480
Gly Ser Thr Asp Ser Thr Ser His Gly Asn Tyr Phe Glu Gln Ile Gly
145                 150                 155                 160 aaa aac caa gcg gct aga ttc acc ata agc ccg caa gca ccg tcc ttt       528
Lys Asn Gln Ala Ala Arg Phe Thr Ile Ser Pro Gln Ala Pro Ser Phe
                165                 170                 175 acg gcc aac atg ggc gag tat gga aca gtt acc att gat tgt gaa gca       576
Thr Ala Asn Met Gly Glu Tyr Gly Thr Val Thr Ile Asp Cys Glu Ala
            180                 185                 190 aga tca gga atc aac acg gag gat tat tat gtt ttc act gtc aag gag       624
Arg Ser Gly Ile Asn Thr Glu Asp Tyr Tyr Val Phe Thr Val Lys Glu
        195                 200                 205 aag tca tgg cta gtg aac agg gac tgg ttt cac gac ttg aac ctt cca       672
Lys Ser Trp Leu Val Asn Arg Asp Trp Phe His Asp Leu Asn Leu Pro
    210                 215                 220 tgg acg agc cct gcc aca act gat tgg cgc aac aga gaa aca ctg gtg       720
Trp Thr Ser Pro Ala Thr Thr Asp Trp Arg Asn Arg Glu Thr Leu Val
225                 230                 235                 240 gaa ttt gag gaa ccg cat gcc acc aag caa act gta gta gcc cta gga       768
Glu Phe Glu Glu Pro His Ala Thr Lys Gln Thr Val Val Ala Leu Gly
                245                 250                 255 tcg caa gaa ggt gcc ctg cac aca gca ttg gct gga gcc att cca gcc       816
Ser Gln Glu Gly Ala Leu His Thr Ala Leu Ala Gly Ala Ile Pro Ala
            260                 265                 270
```

```
act gtt agc agc tca acc cta acc ttg caa tca ggg cat ttg aaa tgc    864
Thr Val Ser Ser Ser Thr Leu Thr Leu Gln Ser Gly His Leu Lys Cys
        275                 280                 285 aga gct aag ctt gac aag gtc aaa atc aag gga acg aca tat ggc atg    912
Arg Ala Lys Leu Asp Lys Val Lys Ile Lys Gly Thr Thr Tyr Gly Met
    290                 295                 300 tgt gac tct gcc ttc acc ttc agc aag aac cca gct gac aca ggg cac    960
Cys Asp Ser Ala Phe Thr Phe Ser Lys Asn Pro Ala Asp Thr Gly His
305                 310                 315                 320 ggg aca gtg att gtg gaa ctg cag tat act gga agc aac gga ccc tgc   1008
Gly Thr Val Ile Val Glu Leu Gln Tyr Thr Gly Ser Asn Gly Pro Cys
            325                 330                 335 cga gtt ccc atc tcc gtg act gca aac ctc atg gat ttg aca ccg gtt   1056
Arg Val Pro Ile Ser Val Thr Ala Asn Leu Met Asp Leu Thr Pro Val
        340                 345                 350 gga aga ttg gtc acg gtc aat ccc ttt ata agc aca ggg gga gcg aac   1104
Gly Arg Leu Val Thr Val Asn Pro Phe Ile Ser Thr Gly Gly Ala Asn
    355                 360                 365 aac aag gtc atg atc gaa gtt gaa cca ccc ttt ggc gat tct tac atc   1152
Asn Lys Val Met Ile Glu Val Glu Pro Pro Phe Gly Asp Ser Tyr Ile
370                 375                 380 gtc gtc gga aga ggc acc acc cag att aac tac cac tgg cac aaa gag   1200
Val Val Gly Arg Gly Thr Thr Gln Ile Asn Tyr His Trp His Lys Glu
385                 390                 395                 400 gga agc acg ctg ggc aag gcc ttt tca aca act ttg aag gga gct caa   1248
Gly Ser Thr Leu Gly Lys Ala Phe Ser Thr Thr Leu Lys Gly Ala Gln
            405                 410                 415 aga ctg gca gcg ttg ggc gac aca gcc tgg gac ttt ggc tct att gga   1296
Arg Leu Ala Ala Leu Gly Asp Thr Ala Trp Asp Phe Gly Ser Ile Gly
        420                 425                 430 ggg gtc ttc aac tcc ata gga aaa gcc gtt cac caa gtg ttt ggt ggt   1344
Gly Val Phe Asn Ser Ile Gly Lys Ala Val His Gln Val Phe Gly Gly
    435                 440                 445 gcc ttc aga aca ctc ttt ggg gga atg tct tgg atc aca caa ggg cta   1392
Ala Phe Arg Thr Leu Phe Gly Gly Met Ser Trp Ile Thr Gln Gly Leu
450                 455                 460 atg ggt gcc cta ctg ctc tgg atg ggc gtc aac gca cga gac cga tca   1440
Met Gly Ala Leu Leu Leu Trp Met Gly Val Asn Ala Arg Asp Arg Ser
465                 470                 475                 480 att gct ttg gcc ttc tta gcc aca ggg ggt gtg ctc gtg ttc tta gcg   1488
Ile Ala Leu Ala Phe Leu Ala Thr Gly Gly Val Leu Val Phe Leu Ala
            485                 490                 495 acc aat gtg cat gct taa                                           1506
Thr Asn Val His Ala
            500

<210> SEQ ID NO 81
<211> LENGTH: 501
<212> TYPE: PRT
<213> ORGANISM: Artificial Sequence
<220> FEATURE:
<223> OTHER INFORMATION: Synthetic Construct

<400> SEQUENCE: 81

Phe Asn Cys Leu Gly Thr Ser Asn Arg Asp Phe Val Glu Gly Ala Ser
1               5                   10                  15

Gly Ala Thr Trp Ile Asp Leu Val Leu Glu Gly Gly Ser Cys Val Thr
            20                  25                  30

Val Met Ala Pro Glu Lys Pro Thr Leu Asp Phe Lys Val Met Lys Met
        35                  40                  45
```

```
Glu Ala Thr Glu Leu Ala Thr Val Arg Glu Tyr Cys Tyr Glu Ala Thr
 50                  55                  60

Leu Asp Thr Leu Ser Thr Val Ala Arg Cys Pro Thr Thr Gly Glu Ala
 65                  70                  75                  80

His Asn Thr Lys Arg Ser Asp Pro Thr Phe Val Cys Lys Arg Asp Val
             85                  90                  95

Val Asp Arg Gly Trp Gly Asn Gly Cys Gly Leu Phe Gly Lys Gly Ser
            100                 105                 110

Ile Asp Thr Cys Ala Lys Phe Thr Cys Lys Asn Lys Ala Thr Gly Lys
            115                 120                 125

Thr Ile Leu Arg Glu Asn Ile Lys Tyr Glu Val Ala Ile Phe Val His
130                 135                 140

Gly Ser Thr Asp Ser Thr Ser His Gly Asn Tyr Phe Glu Gln Ile Gly
145                 150                 155                 160

Lys Asn Gln Ala Ala Arg Phe Thr Ile Ser Pro Gln Ala Pro Ser Phe
                165                 170                 175

Thr Ala Asn Met Gly Glu Tyr Gly Thr Val Thr Ile Asp Cys Glu Ala
            180                 185                 190

Arg Ser Gly Ile Asn Thr Glu Asp Tyr Tyr Val Phe Thr Val Lys Glu
            195                 200                 205

Lys Ser Trp Leu Val Asn Arg Asp Trp Phe His Asp Leu Asn Leu Pro
210                 215                 220

Trp Thr Ser Pro Ala Thr Thr Asp Trp Arg Asn Arg Glu Thr Leu Val
225                 230                 235                 240

Glu Phe Glu Glu Pro His Ala Thr Lys Gln Thr Val Val Ala Leu Gly
                245                 250                 255

Ser Gln Glu Gly Ala Leu His Thr Ala Leu Ala Gly Ala Ile Pro Ala
            260                 265                 270

Thr Val Ser Ser Ser Thr Leu Thr Leu Gln Ser Gly His Leu Lys Cys
            275                 280                 285

Arg Ala Lys Leu Asp Lys Val Lys Ile Lys Gly Thr Thr Tyr Gly Met
290                 295                 300

Cys Asp Ser Ala Phe Thr Phe Ser Lys Asn Pro Ala Asp Thr Gly His
305                 310                 315                 320

Gly Thr Val Ile Val Glu Leu Gln Tyr Thr Gly Ser Asn Gly Pro Cys
                325                 330                 335

Arg Val Pro Ile Ser Val Thr Ala Asn Leu Met Asp Leu Thr Pro Val
            340                 345                 350

Gly Arg Leu Val Thr Val Asn Pro Phe Ile Ser Thr Gly Gly Ala Asn
            355                 360                 365

Asn Lys Val Met Ile Glu Val Glu Pro Pro Phe Gly Asp Ser Tyr Ile
370                 375                 380

Val Val Gly Arg Gly Thr Thr Gln Ile Asn Tyr His Trp His Lys Glu
385                 390                 395                 400

Gly Ser Thr Leu Gly Lys Ala Phe Ser Thr Thr Leu Lys Gly Ala Gln
                405                 410                 415

Arg Leu Ala Ala Leu Gly Asp Thr Ala Trp Asp Phe Gly Ser Ile Gly
            420                 425                 430

Gly Val Phe Asn Ser Ile Gly Lys Ala Val His Gln Val Phe Gly Gly
            435                 440                 445

Ala Phe Arg Thr Leu Phe Gly Gly Met Ser Trp Ile Thr Gln Gly Leu
450                 455                 460
```

```
Met Gly Ala Leu Leu Leu Trp Met Gly Val Asn Ala Arg Asp Arg Ser
465                 470                 475                 480

Ile Ala Leu Ala Phe Leu Ala Thr Gly Gly Val Leu Val Phe Leu Ala
                485                 490                 495

Thr Asn Val His Ala
            500

<210> SEQ ID NO 82
<211> LENGTH: 1506
<212> TYPE: DNA
<213> ORGANISM: Artificial Sequence
<220> FEATURE:
<223> OTHER INFORMATION: St. Louis encephalitis virus/Japanese
      encephalitis virus G106Q envelope chimera.
<220> FEATURE:
<221> NAME/KEY: CDS
<222> LOCATION: (1)..(1503)

<400> SEQUENCE: 82 ttc aac tgt ctg gga aca tca aac agg gac ttt gtc gag gga gcc agt         48
Phe Asn Cys Leu Gly Thr Ser Asn Arg Asp Phe Val Glu Gly Ala Ser
1               5                   10                  15 ggg gca aca tgg att gac ttg gta ctt gaa ggg gga agc tgt gtc aca         96
Gly Ala Thr Trp Ile Asp Leu Val Leu Glu Gly Gly Ser Cys Val Thr
            20                  25                  30 gtg atg gca cca gag aaa cca aca ctg gac ttc aaa gtg atg aag atg        144
Val Met Ala Pro Glu Lys Pro Thr Leu Asp Phe Lys Val Met Lys Met
        35                  40                  45 gag gct acc gag tta gcc act gtg cgt gag tat tgt tac gaa gca acc        192
Glu Ala Thr Glu Leu Ala Thr Val Arg Glu Tyr Cys Tyr Glu Ala Thr
    50                  55                  60 ttg gac acg ctg tca aca gtg gca agg tgc ccc aca aca gga gaa gct        240
Leu Asp Thr Leu Ser Thr Val Ala Arg Cys Pro Thr Thr Gly Glu Ala
65                  70                  75                  80 cac aac acc aaa agg agt gac cca aca ttt gtc tgc aaa aga gat gtt        288
His Asn Thr Lys Arg Ser Asp Pro Thr Phe Val Cys Lys Arg Asp Val
                85                  90                  95 gtg gac cgc gga tgg ggt aac gga tgt cag ctg ttt gga aaa ggg agc        336
Val Asp Arg Gly Trp Gly Asn Gly Cys Gln Leu Phe Gly Lys Gly Ser
            100                 105                 110 att gac aca tgc gct aag ttc aca tgc aaa aac aag gca aca ggg aag        384
Ile Asp Thr Cys Ala Lys Phe Thr Cys Lys Asn Lys Ala Thr Gly Lys
        115                 120                 125 acg atc ttg aga gaa aac atc aag tat gag gtt gca atc ttt gtg cat        432
Thr Ile Leu Arg Glu Asn Ile Lys Tyr Glu Val Ala Ile Phe Val His
    130                 135                 140 ggt tca acg gac tct acg tca cat ggc aat tac ttt gag cag att gga        480
Gly Ser Thr Asp Ser Thr Ser His Gly Asn Tyr Phe Glu Gln Ile Gly
145                 150                 155                 160 aaa aac caa gcg gct aga ttc acc ata agc ccg caa gca ccg tcc ttt        528
Lys Asn Gln Ala Ala Arg Phe Thr Ile Ser Pro Gln Ala Pro Ser Phe
                165                 170                 175 acg gcc aac atg ggc gag tat gga aca gtt acc att gat tgt gaa gca        576
Thr Ala Asn Met Gly Glu Tyr Gly Thr Val Thr Ile Asp Cys Glu Ala
            180                 185                 190 aga tca gga atc aac acg gag gat tat tat gtt ttc act gtc aag gag        624
Arg Ser Gly Ile Asn Thr Glu Asp Tyr Tyr Val Phe Thr Val Lys Glu
        195                 200                 205 aag tca tgg cta gtg aac agg gac tgg ttt cac gac ttg aac ctt cca        672
Lys Ser Trp Leu Val Asn Arg Asp Trp Phe His Asp Leu Asn Leu Pro
    210                 215                 220
```

```
tgg acg agc cct gcc aca act gat tgg cgc aac aga gaa aca ctg gtg      720
Trp Thr Ser Pro Ala Thr Thr Asp Trp Arg Asn Arg Glu Thr Leu Val
225                 230                 235                 240 gaa ttt gag gaa ccg cat gcc acc aag caa act gta gta gcc cta gga      768
Glu Phe Glu Glu Pro His Ala Thr Lys Gln Thr Val Val Ala Leu Gly
                245                 250                 255 tcg caa gaa ggt gcc ctg cac aca gca ttg gct gga gcc att cca gcc      816
Ser Gln Glu Gly Ala Leu His Thr Ala Leu Ala Gly Ala Ile Pro Ala
            260                 265                 270 act gtt agc agc tca acc cta acc ttg caa tca ggg cat ttg aaa tgc      864
Thr Val Ser Ser Ser Thr Leu Thr Leu Gln Ser Gly His Leu Lys Cys
        275                 280                 285 aga gct aag ctt gac aag gtc aaa atc aag gga acg aca tat ggc atg      912
Arg Ala Lys Leu Asp Lys Val Lys Ile Lys Gly Thr Thr Tyr Gly Met
    290                 295                 300 tgt gac tct gcc ttc acc ttc agc aag aac cca gct gac aca ggg cac      960
Cys Asp Ser Ala Phe Thr Phe Ser Lys Asn Pro Ala Asp Thr Gly His
305                 310                 315                 320 ggg aca gtg att gtg gaa ctg cag tat act gga agc aac gga ccc tgc     1008
Gly Thr Val Ile Val Glu Leu Gln Tyr Thr Gly Ser Asn Gly Pro Cys
                325                 330                 335 cga gtt ccc atc tcc gtg act gca aac ctc atg gat ttg aca ccg gtt     1056
Arg Val Pro Ile Ser Val Thr Ala Asn Leu Met Asp Leu Thr Pro Val
            340                 345                 350 gga aga ttg gtc acg gtc aat ccc ttt ata agc aca ggg gga gcg aac     1104
Gly Arg Leu Val Thr Val Asn Pro Phe Ile Ser Thr Gly Gly Ala Asn
        355                 360                 365 aac aag gtc atg atc gaa gtt gaa cca ccc ttt ggc gat tct tac atc     1152
Asn Lys Val Met Ile Glu Val Glu Pro Pro Phe Gly Asp Ser Tyr Ile
    370                 375                 380 gtc gtc gga aga ggc acc acc cag att aac tac cac tgg cac aaa gag     1200
Val Val Gly Arg Gly Thr Thr Gln Ile Asn Tyr His Trp His Lys Glu
385                 390                 395                 400 gga agc acg ctg ggc aag gcc ttt tca aca act ttg aag gga gct caa     1248
Gly Ser Thr Leu Gly Lys Ala Phe Ser Thr Thr Leu Lys Gly Ala Gln
                405                 410                 415 aga ctg gca gcg ttg ggc gac aca gcc tgg gac ttt ggc tct att gga     1296
Arg Leu Ala Ala Leu Gly Asp Thr Ala Trp Asp Phe Gly Ser Ile Gly
            420                 425                 430 ggg gtc ttc aac tcc ata gga aaa gcc gtt cac caa gtg ttt ggt ggt     1344
Gly Val Phe Asn Ser Ile Gly Lys Ala Val His Gln Val Phe Gly Gly
        435                 440                 445 gcc ttc aga aca ctc ttt ggg gga atg tct tgg atc aca caa ggg cta     1392
Ala Phe Arg Thr Leu Phe Gly Gly Met Ser Trp Ile Thr Gln Gly Leu
    450                 455                 460 atg ggt gcc cta ctg ctc tgg atg ggc gtc aac gca cga gac cga tca     1440
Met Gly Ala Leu Leu Leu Trp Met Gly Val Asn Ala Arg Asp Arg Ser
465                 470                 475                 480 att gct ttg gcc ttc tta gcc aca ggg ggt gtg ctc gtg ttc tta gcg     1488
Ile Ala Leu Ala Phe Leu Ala Thr Gly Gly Val Leu Val Phe Leu Ala
                485                 490                 495 acc aat gtg cat gct taa                                             1506
Thr Asn Val His Ala
            500

<210> SEQ ID NO 83
<211> LENGTH: 501
<212> TYPE: PRT
<213> ORGANISM: Artificial Sequence
<220> FEATURE:
<223> OTHER INFORMATION: Synthetic Construct
```

<400> SEQUENCE: 83

Phe Asn Cys Leu Gly Thr Ser Asn Arg Asp Phe Val Glu Gly Ala Ser
1               5                   10                  15

Gly Ala Thr Trp Ile Asp Leu Val Leu Glu Gly Gly Ser Cys Val Thr
            20                  25                  30

Val Met Ala Pro Glu Lys Pro Thr Leu Asp Phe Lys Val Met Lys Met
        35                  40                  45

Glu Ala Thr Glu Leu Ala Thr Val Arg Glu Tyr Cys Tyr Glu Ala Thr
    50                  55                  60

Leu Asp Thr Leu Ser Thr Val Ala Arg Cys Pro Thr Thr Gly Glu Ala
65                  70                  75                  80

His Asn Thr Lys Arg Ser Asp Pro Thr Phe Val Cys Lys Arg Asp Val
                85                  90                  95

Val Asp Arg Gly Trp Gly Asn Gly Cys Gln Leu Phe Gly Lys Gly Ser
            100                 105                 110

Ile Asp Thr Cys Ala Lys Phe Thr Cys Lys Asn Lys Ala Thr Gly Lys
        115                 120                 125

Thr Ile Leu Arg Glu Asn Ile Lys Tyr Glu Val Ala Ile Phe Val His
130                 135                 140

Gly Ser Thr Asp Ser Thr Ser His Gly Asn Tyr Phe Glu Gln Ile Gly
145                 150                 155                 160

Lys Asn Gln Ala Ala Arg Phe Thr Ile Ser Pro Gln Ala Pro Ser Phe
                165                 170                 175

Thr Ala Asn Met Gly Glu Tyr Gly Thr Val Thr Ile Asp Cys Glu Ala
            180                 185                 190

Arg Ser Gly Ile Asn Thr Glu Asp Tyr Tyr Val Phe Thr Val Lys Glu
        195                 200                 205

Lys Ser Trp Leu Val Asn Arg Asp Trp Phe His Asp Leu Asn Leu Pro
210                 215                 220

Trp Thr Ser Pro Ala Thr Thr Asp Trp Arg Asn Arg Glu Thr Leu Val
225                 230                 235                 240

Glu Phe Glu Glu Pro His Ala Thr Lys Gln Thr Val Val Ala Leu Gly
                245                 250                 255

Ser Gln Glu Gly Ala Leu His Thr Ala Leu Ala Gly Ala Ile Pro Ala
            260                 265                 270

Thr Val Ser Ser Ser Thr Leu Thr Leu Gln Ser Gly His Leu Lys Cys
        275                 280                 285

Arg Ala Lys Leu Asp Lys Val Lys Ile Lys Gly Thr Thr Tyr Gly Met
290                 295                 300

Cys Asp Ser Ala Phe Thr Phe Ser Lys Asn Pro Ala Asp Thr Gly His
305                 310                 315                 320

Gly Thr Val Ile Val Glu Leu Gln Tyr Thr Gly Ser Asn Gly Pro Cys
                325                 330                 335

Arg Val Pro Ile Ser Val Thr Ala Asn Leu Met Asp Leu Thr Pro Val
            340                 345                 350

Gly Arg Leu Val Thr Val Asn Pro Phe Ile Ser Thr Gly Gly Ala Asn
        355                 360                 365

Asn Lys Val Met Ile Glu Val Glu Pro Pro Phe Gly Asp Ser Tyr Ile
370                 375                 380

Val Val Gly Arg Gly Thr Thr Gln Ile Asn Tyr His Trp His Lys Glu
385                 390                 395                 400

Gly Ser Thr Leu Gly Lys Ala Phe Ser Thr Thr Leu Lys Gly Ala Gln

```
                    405                 410                 415
Arg Leu Ala Ala Leu Gly Asp Thr Ala Trp Asp Phe Gly Ser Ile Gly
            420                 425                 430

Gly Val Phe Asn Ser Ile Gly Lys Ala Val His Gln Val Phe Gly Gly
        435                 440                 445

Ala Phe Arg Thr Leu Phe Gly Met Ser Trp Ile Thr Gln Gly Leu
    450                 455                 460

Met Gly Ala Leu Leu Leu Trp Met Gly Val Asn Ala Arg Asp Arg Ser
465                 470                 475                 480

Ile Ala Leu Ala Phe Leu Ala Thr Gly Gly Val Leu Val Phe Leu Ala
                485                 490                 495

Thr Asn Val His Ala
            500

<210> SEQ ID NO 84
<211> LENGTH: 1506
<212> TYPE: DNA
<213> ORGANISM: Artificial Sequence
<220> FEATURE:
<223> OTHER INFORMATION: West Nile virus envelope gene region.
<220> FEATURE:
<221> NAME/KEY: CDS
<222> LOCATION: (1)..(1503)
<220> FEATURE:
<221> NAME/KEY: misc_feature
<222> LOCATION: (316)..(318)
<223> OTHER INFORMATION: Mutagenesis of GGA codon to GTC codon produces
      a G106V substitution.

<400> SEQUENCE: 84 ttc aac tgc ctt gga atg agc aac aga gac ttc ttg gaa gga gtg tct       48
Phe Asn Cys Leu Gly Met Ser Asn Arg Asp Phe Leu Glu Gly Val Ser
1               5                   10                  15 gga gca aca tgg gtg gat ttg gtt ctc gaa ggc gac agc tgc gtg act       96
Gly Ala Thr Trp Val Asp Leu Val Leu Glu Gly Asp Ser Cys Val Thr
            20                  25                  30 atc atg tct aag gac aag cct acc atc gat gtg aag atg atg aat atg      144
Ile Met Ser Lys Asp Lys Pro Thr Ile Asp Val Lys Met Met Asn Met
        35                  40                  45 gag gcg gcc aac ctg gca gag gtc cgc agt tat tgc tat ttg gct acc      192
Glu Ala Ala Asn Leu Ala Glu Val Arg Ser Tyr Cys Tyr Leu Ala Thr
    50                  55                  60 gtc agc gat ctc tcc acc aaa gct gcg tgc ccg acc atg gga gaa gct      240
Val Ser Asp Leu Ser Thr Lys Ala Ala Cys Pro Thr Met Gly Glu Ala
65                  70                  75                  80 cac aat gac aaa cgt gct gac cca gct ttt gtg tgc aga caa gga gtg      288
His Asn Asp Lys Arg Ala Asp Pro Ala Phe Val Cys Arg Gln Gly Val
                85                  90                  95 gtg gac agg ggc tgg ggc aac ggc tgc gga cta ttt ggc aaa gga agc      336
Val Asp Arg Gly Trp Gly Asn Gly Cys Gly Leu Phe Gly Lys Gly Ser
            100                 105                 110 att gac aca tgc gcc aaa ttt gcc tgc tct acc aag gca ata gga aga      384
Ile Asp Thr Cys Ala Lys Phe Ala Cys Ser Thr Lys Ala Ile Gly Arg
        115                 120                 125 acc atc ttg aaa gag aat atc aag tac gaa gtg gcc att ttt gtc cat      432
Thr Ile Leu Lys Glu Asn Ile Lys Tyr Glu Val Ala Ile Phe Val His
    130                 135                 140 gga cca act act gtg gag tcg cac gga aac tac tcc aca cag gtt gga      480
Gly Pro Thr Thr Val Glu Ser His Gly Asn Tyr Ser Thr Gln Val Gly
145                 150                 155                 160 gcc act cag gca ggg aga ttc agc atc act cct gcg gcg cct tca tac      528
```

-continued

|  |  |  |  |  |  |  |  |  |  |  |  |  |  |
|---|---|---|---|---|---|---|---|---|---|---|---|---|---|
| Ala | Thr | Gln | Ala | Gly | Arg | Phe | Ser | Ile | Thr | Pro | Ala | Pro | Ser | Tyr |
|  |  |  |  | 165 |  |  |  | 170 |  |  |  | 175 |

```
aca cta aag ctt gga gaa tat gga gag gtg aca gtg gac tgt gaa cca      576
Thr Leu Lys Leu Gly Glu Tyr Gly Glu Val Thr Val Asp Cys Glu Pro
        180                 185                 190 cgg tca ggg att gac acc aat gca tac tac gtg atg act gtt gga aca      624
Arg Ser Gly Ile Asp Thr Asn Ala Tyr Tyr Val Met Thr Val Gly Thr
            195                 200                 205 aag acg ttc ttg gtc cat cgt gag tgg ttc atg gac ctc aac ctc cct      672
Lys Thr Phe Leu Val His Arg Glu Trp Phe Met Asp Leu Asn Leu Pro
    210                 215                 220 tgg agc agt gct gga agt act gtg tgg agg aac aga gag acg tta atg      720
Trp Ser Ser Ala Gly Ser Thr Val Trp Arg Asn Arg Glu Thr Leu Met
225                 230                 235                 240 gag ttt gag gaa cca cac gcc acg aag cag tct gtg ata gca ttg ggc      768
Glu Phe Glu Glu Pro His Ala Thr Lys Gln Ser Val Ile Ala Leu Gly
                245                 250                 255 tca caa gag gga gct ctg cat caa gct ttg gct gga gcc att cct gtg      816
Ser Gln Glu Gly Ala Leu His Gln Ala Leu Ala Gly Ala Ile Pro Val
            260                 265                 270 gaa ttt tca agc aac act gtc aag ttg acg tcg ggt cat ttg aag tgt      864
Glu Phe Ser Ser Asn Thr Val Lys Leu Thr Ser Gly His Leu Lys Cys
        275                 280                 285 aga gtg aag atg gaa aaa ttg cag ttg aag gga aca acc tat ggc gtc      912
Arg Val Lys Met Glu Lys Leu Gln Leu Lys Gly Thr Thr Tyr Gly Val
    290                 295                 300 tgt tca aag gct ttc aag ttt ctt ggg act ccc gcg gac aca ggt cac      960
Cys Ser Lys Ala Phe Lys Phe Leu Gly Thr Pro Ala Asp Thr Gly His
305                 310                 315                 320 ggc act gtg gtg ttg gaa ttg cag tac act ggc acg gat gga cct tgc     1008
Gly Thr Val Val Leu Glu Leu Gln Tyr Thr Gly Thr Asp Gly Pro Cys
                325                 330                 335 aaa gtt cct atc tcg tca gtg gct tca ttg aac gac cta acg cca gtg     1056
Lys Val Pro Ile Ser Ser Val Ala Ser Leu Asn Asp Leu Thr Pro Val
            340                 345                 350 ggc aga ttg gtc act gtc aac cct ttt gtt tca gtg gcc acg gcc aac     1104
Gly Arg Leu Val Thr Val Asn Pro Phe Val Ser Val Ala Thr Ala Asn
        355                 360                 365 gct aag gtc ctg att gaa ttg gaa cca ccc ttt gga gac tca tac ata     1152
Ala Lys Val Leu Ile Glu Leu Glu Pro Pro Phe Gly Asp Ser Tyr Ile
    370                 375                 380 gtg gtg ggc aga gga gaa caa cag atc aat cac cat tgg cac aag tct     1200
Val Val Gly Arg Gly Glu Gln Gln Ile Asn His His Trp His Lys Ser
385                 390                 395                 400 gga agc agc att ggc aaa gcc ttt aca acc acc ctc aaa gga gcg cag     1248
Gly Ser Ser Ile Gly Lys Ala Phe Thr Thr Thr Leu Lys Gly Ala Gln
                405                 410                 415 aga cta gcc gct cta gga gac aca gct tgg gac ttt gga tca gtt gga     1296
Arg Leu Ala Ala Leu Gly Asp Thr Ala Trp Asp Phe Gly Ser Val Gly
            420                 425                 430 ggg gtg ttc acc tca gtt ggg aag gct gtc cat caa gtg ttc gga gga     1344
Gly Val Phe Thr Ser Val Gly Lys Ala Val His Gln Val Phe Gly Gly
        435                 440                 445 gca ttc cgc tca ctg ttc gga ggc atg tcc tgg ata acg caa gga ttg     1392
Ala Phe Arg Ser Leu Phe Gly Gly Met Ser Trp Ile Thr Gln Gly Leu
    450                 455                 460 ctg ggg gct ctc ctg ttg tgg atg ggc atc aat gct cgt gat agg tcc     1440
Leu Gly Ala Leu Leu Leu Trp Met Gly Ile Asn Ala Arg Asp Arg Ser
465                 470                 475                 480
```

|  |  |  |  |  |  |  |  |  |  |  |  |  |
|---|---|---|---|---|---|---|---|---|---|---|---|---|
| ata | gct | ctc | acg | ttt | ctc | gca | gtt | gga | gga | gtt | ctg | ctc | ttc | ctc | tcc | 1488 |
| Ile | Ala | Leu | Thr | Phe | Leu | Ala | Val | Gly | Gly | Val | Leu | Leu | Phe | Leu | Ser |
|  |  |  | 485 |  |  |  |  | 490 |  |  |  |  | 495 |  |  |
| gtg | aac | gtg | cac | gcc | tga |  |  |  |  |  |  |  |  |  |  | 1506 |
| Val | Asn | Val | His | Ala |
|  |  |  | 500 |

<210> SEQ ID NO 85
<211> LENGTH: 501
<212> TYPE: PRT
<213> ORGANISM: Artificial Sequence
<220> FEATURE:
<223> OTHER INFORMATION: Synthetic Construct

<400> SEQUENCE: 85

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys

```
                    325                 330                 335
Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
            355                 360                 365

Ala Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
            405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
            435                 440                 445

Ala Phe Arg Ser Leu Phe Gly Gly Met Ser Trp Ile Thr Gln Gly Leu
            450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
            485                 490                 495

Val Asn Val His Ala
            500

<210> SEQ ID NO 86
<211> LENGTH: 1506
<212> TYPE: DNA
<213> ORGANISM: Artificial Sequence
<220> FEATURE:
<223> OTHER INFORMATION: West Nile virus envelope gene region with G106V
      substitution.
<220> FEATURE:
<221> NAME/KEY: CDS
<222> LOCATION: (1)..(1503)

<400> SEQUENCE: 86 ttc aac tgc ctt gga atg agc aac aga gac ttc ttg gaa gga gtg tct      48
Phe Asn Cys Leu Gly Met Ser Asn Arg Asp Phe Leu Glu Gly Val Ser
1               5                   10                  15 gga gca aca tgg gtg gat ttg gtt ctc gaa ggc gac agc tgc gtg act      96
Gly Ala Thr Trp Val Asp Leu Val Leu Glu Gly Asp Ser Cys Val Thr
            20                  25                  30 atc atg tct aag gac aag cct acc atc gat gtg aag atg atg aat atg     144
Ile Met Ser Lys Asp Lys Pro Thr Ile Asp Val Lys Met Met Asn Met
        35                  40                  45 gag gcg gcc aac ctg gca gag gtc cgc agt tat tgc tat ttg gct acc     192
Glu Ala Ala Asn Leu Ala Glu Val Arg Ser Tyr Cys Tyr Leu Ala Thr
    50                  55                  60 gtc agc gat ctc tcc acc aaa gct gcg tgc ccg acc atg gga gaa gct     240
Val Ser Asp Leu Ser Thr Lys Ala Ala Cys Pro Thr Met Gly Glu Ala
65                  70                  75                  80 cac aat gac aaa cgt gct gac cca gct ttt gtg tgc aga caa gga gtg     288
His Asn Asp Lys Arg Ala Asp Pro Ala Phe Val Cys Arg Gln Gly Val
                85                  90                  95 gtg gac agg ggc tgg ggc aac ggc tgc gtc cta ttt ggc aaa gga agc     336
Val Asp Arg Gly Trp Gly Asn Gly Cys Val Leu Phe Gly Lys Gly Ser
            100                 105                 110 att gac aca tgc gcc aaa ttt gcc tgc tct acc aag gca ata gga aga     384
Ile Asp Thr Cys Ala Lys Phe Ala Cys Ser Thr Lys Ala Ile Gly Arg
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |
| acc | atc | ttg | aaa | gag | aat | atc | aag | tac | gaa | gtg | gcc | att | ttt | gtc | cat | 432 |
| Thr | Ile | Leu | Lys | Glu | Asn | Ile | Lys | Tyr | Glu | Val | Ala | Ile | Phe | Val | His |  |
|  | 130 |  |  |  |  | 135 |  |  |  |  | 140 |  |  |  |  |  |
| gga | cca | act | act | gtg | gag | tcg | cac | gga | aac | tac | tcc | aca | cag | gtt | gga | 480 |
| Gly | Pro | Thr | Thr | Val | Glu | Ser | His | Gly | Asn | Tyr | Ser | Thr | Gln | Val | Gly |  |
| 145 |  |  |  |  | 150 |  |  |  |  | 155 |  |  |  |  | 160 |  |
| gcc | act | cag | gca | ggg | aga | ttc | agc | atc | act | cct | gcg | gcg | cct | tca | tac | 528 |
| Ala | Thr | Gln | Ala | Gly | Arg | Phe | Ser | Ile | Thr | Pro | Ala | Ala | Pro | Ser | Tyr |  |
|  |  |  |  | 165 |  |  |  |  | 170 |  |  |  |  | 175 |  |  |
| aca | cta | aag | ctt | gga | gaa | tat | gga | gag | gtg | aca | gtg | gac | tgt | gaa | cca | 576 |
| Thr | Leu | Lys | Leu | Gly | Glu | Tyr | Gly | Glu | Val | Thr | Val | Asp | Cys | Glu | Pro |  |
|  |  |  | 180 |  |  |  |  | 185 |  |  |  |  | 190 |  |  |  |
| cgg | tca | ggg | att | gac | acc | aat | gca | tac | tac | gtg | atg | act | gtt | gga | aca | 624 |
| Arg | Ser | Gly | Ile | Asp | Thr | Asn | Ala | Tyr | Tyr | Val | Met | Thr | Val | Gly | Thr |  |
|  |  | 195 |  |  |  |  | 200 |  |  |  |  | 205 |  |  |  |  |
| aag | acg | ttc | ttg | gtc | cat | cgt | gag | tgg | ttc | atg | gac | ctc | aac | ctc | cct | 672 |
| Lys | Thr | Phe | Leu | Val | His | Arg | Glu | Trp | Phe | Met | Asp | Leu | Asn | Leu | Pro |  |
|  | 210 |  |  |  |  | 215 |  |  |  |  | 220 |  |  |  |  |  |
| tgg | agc | agt | gct | gga | agt | act | gtg | tgg | agg | aac | aga | gag | acg | tta | atg | 720 |
| Trp | Ser | Ser | Ala | Gly | Ser | Thr | Val | Trp | Arg | Asn | Arg | Glu | Thr | Leu | Met |  |
| 225 |  |  |  |  | 230 |  |  |  |  | 235 |  |  |  |  | 240 |  |
| gag | ttt | gag | gaa | cca | cac | gcc | acg | aag | cag | tct | gtg | ata | gca | ttg | ggc | 768 |
| Glu | Phe | Glu | Glu | Pro | His | Ala | Thr | Lys | Gln | Ser | Val | Ile | Ala | Leu | Gly |  |
|  |  |  |  | 245 |  |  |  |  | 250 |  |  |  |  | 255 |  |  |
| tca | caa | gag | gga | gct | ctg | cat | caa | gct | ttg | gct | gga | gcc | att | cct | gtg | 816 |
| Ser | Gln | Glu | Gly | Ala | Leu | His | Gln | Ala | Leu | Ala | Gly | Ala | Ile | Pro | Val |  |
|  |  |  | 260 |  |  |  |  | 265 |  |  |  |  | 270 |  |  |  |
| gaa | ttt | tca | agc | aac | act | gtc | aag | ttg | acg | tcg | ggt | cat | ttg | aag | tgt | 864 |
| Glu | Phe | Ser | Ser | Asn | Thr | Val | Lys | Leu | Thr | Ser | Gly | His | Leu | Lys | Cys |  |
|  |  | 275 |  |  |  |  | 280 |  |  |  |  | 285 |  |  |  |  |
| aga | gtg | aag | atg | gaa | aaa | ttg | cag | ttg | aag | gga | aca | acc | tat | ggc | gtc | 912 |
| Arg | Val | Lys | Met | Glu | Lys | Leu | Gln | Leu | Lys | Gly | Thr | Thr | Tyr | Gly | Val |  |
|  | 290 |  |  |  |  | 295 |  |  |  |  | 300 |  |  |  |  |  |
| tgt | tca | aag | gct | ttc | aag | ttt | ctt | ggg | act | ccc | gcg | gac | aca | ggt | cac | 960 |
| Cys | Ser | Lys | Ala | Phe | Lys | Phe | Leu | Gly | Thr | Pro | Ala | Asp | Thr | Gly | His |  |
| 305 |  |  |  |  | 310 |  |  |  |  | 315 |  |  |  |  | 320 |  |
| ggc | act | gtg | gtg | ttg | gaa | ttg | cag | tac | act | ggc | acg | gat | gga | cct | tgc | 1008 |
| Gly | Thr | Val | Val | Leu | Glu | Leu | Gln | Tyr | Thr | Gly | Thr | Asp | Gly | Pro | Cys |  |
|  |  |  |  | 325 |  |  |  |  | 330 |  |  |  |  | 335 |  |  |
| aaa | gtt | cct | atc | tcg | tca | gtg | gct | tca | ttg | aac | gac | cta | acg | cca | gtg | 1056 |
| Lys | Val | Pro | Ile | Ser | Ser | Val | Ala | Ser | Leu | Asn | Asp | Leu | Thr | Pro | Val |  |
|  |  |  | 340 |  |  |  |  | 345 |  |  |  |  | 350 |  |  |  |
| ggc | aga | ttg | gtc | act | gtc | aac | cct | ttt | gtt | tca | gtg | gcc | acg | gcc | aac | 1104 |
| Gly | Arg | Leu | Val | Thr | Val | Asn | Pro | Phe | Val | Ser | Val | Ala | Thr | Ala | Asn |  |
|  |  | 355 |  |  |  |  | 360 |  |  |  |  | 365 |  |  |  |  |
| gct | aag | gtc | ctg | att | gaa | ttg | gaa | cca | ccc | ttt | gga | gac | tca | tac | ata | 1152 |
| Ala | Lys | Val | Leu | Ile | Glu | Leu | Glu | Pro | Pro | Phe | Gly | Asp | Ser | Tyr | Ile |  |
|  | 370 |  |  |  |  | 375 |  |  |  |  | 380 |  |  |  |  |  |
| gtg | gtg | ggc | aga | gga | gaa | caa | cag | atc | aat | cac | cat | tgg | cac | aag | tct | 1200 |
| Val | Val | Gly | Arg | Gly | Glu | Gln | Gln | Ile | Asn | His | His | Trp | His | Lys | Ser |  |
| 385 |  |  |  |  | 390 |  |  |  |  | 395 |  |  |  |  | 400 |  |
| gga | agc | agc | att | ggc | aaa | gcc | ttt | aca | acc | acc | ctc | aaa | gga | gcg | cag | 1248 |
| Gly | Ser | Ser | Ile | Gly | Lys | Ala | Phe | Thr | Thr | Thr | Leu | Lys | Gly | Ala | Gln |  |
|  |  |  |  | 405 |  |  |  |  | 410 |  |  |  |  | 415 |  |  |
| aga | cta | gcc | gct | cta | gga | gac | aca | gct | tgg | gac | ttt | gga | tca | gtt | gga | 1296 |
| Arg | Leu | Ala | Ala | Leu | Gly | Asp | Thr | Ala | Trp | Asp | Phe | Gly | Ser | Val | Gly |  |
|  |  |  | 420 |  |  |  |  | 425 |  |  |  |  | 430 |  |  |  |
| ggg | gtg | ttc | acc | tca | gtt | ggg | aag | gct | gtc | cat | caa | gtg | ttc | gga | gga | 1344 |

```
Gly Val Phe Thr Ser Val Gly Lys Ala Val His Gln Val Phe Gly Gly
            435                 440                 445 gca ttc cgc tca ctg ttc gga ggc atg tcc tgg ata acg caa gga ttg      1392
Ala Phe Arg Ser Leu Phe Gly Gly Met Ser Trp Ile Thr Gln Gly Leu
        450                 455                 460 ctg ggg gct ctc ctg ttg tgg atg ggc atc aat gct cgt gat agg tcc      1440
Leu Gly Ala Leu Leu Leu Trp Met Gly Ile Asn Ala Arg Asp Arg Ser
465                 470                 475                 480 ata gct ctc acg ttt ctc gca gtt gga gga gtt ctg ctc ttc ctc tcc      1488
Ile Ala Leu Thr Phe Leu Ala Val Gly Gly Val Leu Leu Phe Leu Ser
                485                 490                 495 gtg aac gtg cac gcc tga                                              1506
Val Asn Val His Ala
                500

<210> SEQ ID NO 87
<211> LENGTH: 501
<212> TYPE: PRT
<213> ORGANISM: Artificial Sequence
<220> FEATURE:
<223> OTHER INFORMATION: Synthetic Construct

<400> SEQUENCE: 87

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Val Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270
```

-continued

```
Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
                355                 360                 365

Ala Lys Val Leu Ile Glu Leu Glu Pro Pro Phe Gly Asp Ser Tyr Ile
        370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
                405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
                435                 440                 445

Ala Phe Arg Ser Leu Phe Gly Gly Met Ser Trp Ile Thr Gln Gly Leu
        450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
                485                 490                 495

Val Asn Val His Ala
            500
```

LOCALIZATION AND CHARACTERIZATION OF FLAVIVIRUS ENVELOPE GLYCOPROTEIN CROSS-REACTIVE EPITOPES AND METHODS FOR THEIR USE

PRIORITY CLAIM

This is a Divisional of U.S. patent application Ser. No. 11/572,805, filed Jan. 26, 2007, now U.S. Pat. No. 7,906,292, issued Mar. 15, 2011, which is a §371 U.S. National Stage of PCT/US2005/026672, filed Jul. 27, 2005 (published in English under PCT Article 21(2)), which in turn claims the benefit of U.S. Provisional Patent Application No. 60/591,898, filed Jul. 27, 2004, each of which is incorporated herein by reference in its entirety.

STATEMENT OF GOVERNMENT SUPPORT

This invention was made by the Centers for Disease Control and Prevention, an agency of the United States Government. Therefore, the U.S. Government has certain rights in this invention.

FIELD

This disclosure relates to a structure-based rational mutagenesis method for identifying flavivirus envelope (E)-glycoprotein cross-reactive epitopes. The disclosure further relates to flavivirus E-glycoprotein cross-reactive epitopes and mutants thereof having reduced or ablated cross-reactivity. Flavivirus cross-reactive E-glycoprotein epitopes with reduced or ablated cross-reactivity are useful in the diagnosis, inhibition and treatment of diseases caused by flaviviruses.

BACKGROUND

The Flaviviridae are a diverse family of enveloped viruses infecting both arthropods and vertebrates. Flaviviruses have a positive-sense single-stranded RNA genome 10.7 kb in length, transcribed into a single polyprotein precursor encoding three structural proteins, capsid, premembrane (prM), envelope (E), and seven non-structural proteins (Lindenbach & Rice, *Flaviviridae: the viruses and their replication*. In *Fields Virology*, 4$^{th}$ ed., Knipe and Howley. Eds., Philadelphia, Lippincott Williams & Wilkins, pp. 991-1041, 2001; Rice et al., *Science* 229:726-33, 1985). The flavivirus E-glycoprotein is the primary antigen, inducing protective immunity; it is essential for membrane fusion, and mediates binding to cellular receptors (Allison et al., *J. Virol.* 75:4268-75, 2001; Crill & Roehrig, *J. Virol.* 75:7769-73, 2001; Rey et al., *Nature* 375:291-98, 1995). Flavivirus E-glycoprotein therefore directly affects host range, tissue tropism, and the virulence of these viruses.

The flavivirus E-glycoprotein contains three structural and functional domains. Domain I (DI) is an 8-stranded β-barrel containing two large insertion loops that form the elongated finger-like domain II (DII) (Rey et al., *Nature* 375:291-98, 1995). DII is involved in stabilizing the E-glycoprotein dimer and contains the internal fusion peptide (Allison et al., *J. Virol.* 75:4268-75, 2001). Domain III (DIII) forms a ten-stranded β-barrel with an immunoglobulin-like fold and contains the cellular receptor-binding motifs (Crill & Roehrig, *J. Virol.* 75:7769-73, 2001; Modis et al., *PNAS* 100:6986-91, 2003). DI and DIII contain predominately type-specific and subcomplex-reactive epitopes, whereas DII contains the major flavivirus group- and subgroup-cross-reactive epitopes, which are sensitive to reduction and denaturation and are formed from discontinuous amino acid sequences (Mandl et al., *J. Virol.* 63:564-71, 1989; Rey et al., *Nature* 375:291-98, 1995; Roehrig et al., *Virology* 246:317-28, 1998).

Members of the Flaviviridae family that infect humans frequently cause severe morbidity and mortality, and epidemics of flaviviruses continue to be a major public health concern worldwide. More than two billion people are at risk of being infected with members of the genus Flavivirus which includes at least 70 distinct virus species (Burke & Monath, Flaviviruses. In *Fields Virology*, 4$^{th}$ ed., Knipe and Howley. Eds., Philadelphia, Lippincott Williams & Wilkins, pp. 1043-1125, 2001; Kuno et al., *J. Virol.* 72:73-83, 1998; Solomon & Mallewa, *J. Infect.* 42:104-15, 2001). The medically important flaviviruses include yellow fever (YF) virus in Africa, Latin and South America; Japanese encephalitis (JE) virus in Asia and Australia; West Nile (WN) virus in Africa, Central Europe, and most recently in North America; tick-borne encephalitis (TBE) complex viruses in the temperate regions of Europe, North America and Asia; and the four serotypes of dengue viruses (DEN-1, -2, -3, and -4) in tropical and sub-tropical regions of, the world (Lindenbach & Rice, *Flaviviridae: the viruses and their replication*. In *Fields Virology*, 4$^{th}$ ed., Knipe and Howley. Eds., Philadelphia, Lippincott Williams & Wilkins, pp. 991-1041, 2001).

Human infection by flaviviruses results in a humoral immune response involving virus species-specific as well as flavivirus cross-reactive antibodies (Calisher et al., *J. Gen. Virol.* 70:37-43, 1989; Tesh et al., *Emerg. Inf. Dis.* 8:245-51, 2002). The presence of flavivirus cross-reactive antibodies in human sera produces two public health concerns upon secondary infection with a heterologous flavivirus. Serodiagnosis of secondary flavivirus infections, especially in areas with multiple co-circulating flaviviruses, can be particularly difficult due to the inability to differentiate primary from secondary cross-reactive serum antibodies using currently available viral antigens. Therefore, definitive epidemiological information either cannot be obtained or is delayed to the point that effective control and prevention strategies may be delayed. Additionally, the presence of sub-neutralizing levels of flavivirus cross-reactive serum antibodies may result in increasing the severity of secondary flavivirus infections due to antibody-dependant enhancement (ADE), in particular, following secondary dengue virus infection (Ferguson et al., *PNAS* 96:790-94, 1999; Halstead, *Rev. Infect. Dis.* 11:830-39, 1989; Takada & Kawaoka, *Rev. Med. Virol.* 13:387-98, 2003; Wallace et al., *J. Gen Virol.* 84:1723-28, 2003). Thus, there exists a need for a method for identifying and characterizing flavivirus cross-reactive epitopes for improved flavivirus serodiagnosis and development of flavivirus vaccines.

SUMMARY OF THE DISCLOSURE

Multiple flavivirus E-glycoprotein cross-reactive epitopes and mutant E-glycoprotein polypeptides thereof exhibiting reduced or ablated cross-reactivity have been identified. In various embodiments, these E-glycoprotein polypeptides with reduced or ablated cross-reactivity are capable of eliciting effective type-specific immune responses against Flaviviruses. In one example, the identified cross-reactive epitopes incorporate the highly conserved $Gly_{104}$, $Gly_{106}$, and $Leu_{107}$ residues. In another example, the identified cross-reactive epitope centers on the strictly conserved $Trp_{231}$ residue and its structurally related neighbors $Glu_{126}$ and $Thr_{226}$.

Also described herein are recombinant flavivirus E-glycoprotein constructs that can be used directly or indirectly to stimulate flavivirus type-specific antibodies. These constructs are designed to elicit T-cell, B-cell, or both T-cell and B-cell responses against flavivirus type-specific epitopes. The constructs, when integrated into a vector, can be used as immunogens, can be used as DNA vaccines, and can be used as sources of recombinant protein for stimulation of immune responses in subjects, as well as for protein boosts to subjects who have received a nucleic acid construct previously. Also provided are methods of identifying and characterizing flavivirus E-glycoprotein amino acid residues incorporated into cross-reactive epitopes, using structure-based rational mutagenesis.

The foregoing and other features and advantages will become more apparent from the following detailed description of several embodiments, which proceeds with reference to the accompanying figures.

BRIEF DESCRIPTION OF THE FIGURES

FIGS. 2A to 2C are diagrammatical representations of the structural locations of cross-reactive epitope residues for flavivirus cross-reactive monoclonal antibodies (mAbs) in the atomic structure of the DEN-2 virus E-glycoprotein dimer, as well as a bar graph indicating fold reductions in mAb reactivities assayed by indirect immuno-fluorescence assay (IFA) and/or antigen-capture ELISA (Ag-ELISA) for mutations at these E-glycoprotein positions.

FIG. 2A is a diagrammatical representation of a portion of the atomic structure of the DEN-2 virus E-glycoprotein homodimer, showing the flavivirus group-reactive mAb 4G2 and 6B6C-1 epitope residues from the fusion peptide region of DII. The flavivirus fusion peptide comprises the highly conserved E-glycoprotein residues 98-113, which form a surface exposed loop of hydrophobic residues rich in glycine at the tip of DII (Rey et al., Nature 375:291-98, 1995; Allison et al., J. Virol. 75:4268-75, 2001). The view is looking downward toward the viral membrane surface at an angle of approximately 45°, while looking in towards the fusion peptide region about 45° off of parallel to the dimer's longitudinal axis. The molecular surfaces of DI and DIII from the alternate sub-unit are depicted as space-filling Van der Waals surfaces to highlight the close fitting of the fusion peptide into this region. Fusion peptide residues 100-108 are depicted as stick representations with the participating amino acids labeled. Glycan moieties attached to $Asn_{153}$ and $Asn_{67}$ are labeled CHO153 and CHO67, respectively.

FIG. 2B is a diagrammatical representation of a portion of the atomic structure of the DEN-2 virus E-glycoprotein homodimer, showing the flavivirus subgroup-reactive mAb 1B7-5 epitope residues. The view and labeling are the same as in FIG. 2A. Identified residues are depicted as sticks and labeled.

FIG. 2C is a bar graph showing fold decreases in mAb reactivities in Ag-ELISA for DEN-2 VLPs with substitutions at the listed residues. mAbs 4G2 and 6B6C-1 are flavivirus group-reactive and 1B7-5 is flavivirus subgroup-reactive. Substitutions at $G_{104}$ and $W_{231}$ produced plasmids that were unable to secrete measurable VLP antigen into tissue culture media. Therefore, fold decreases in mAb reactivities for these two constructs are from IFA. Wild-type plasmid did not produce an endpoint nearly as far out in IFA as in Ag-ELISA (see Table 3), therefore the fold reductions for substitutions at $G_{104}$ and $W_{231}$ were not as great as for other constructs measured by Ag-ELISA, even though substitutions at these two positions appeared to completely ablate mAb reactivity.

FIG. 3 is a bar graph showing the percent of cross-reactive epitope residue substitutions altering reactivities of mAbs of different cross-reactivities. The total number of SLEV and WNV mAbs of each type is shown in the legend on the y-axis, and the number of substitutions altering these mAbs is shown in the columns.

BRIEF DESCRIPTION OF THE APPENDICES

Figure 1:
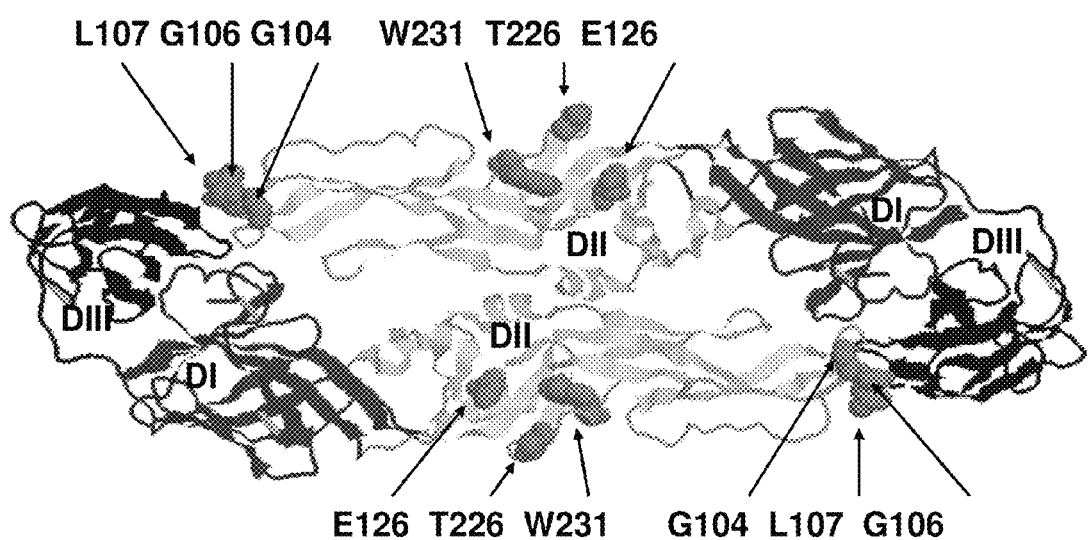
FIG. 1 is a diagrammatical representation of the quaternary structure of the DEN-2 virus E-glycoprotein homodimer, top view, looking down towards the viral surface, showing the locations of flavivirus cross-reactive epitope residues (space-filling representation). The structural and functional domains I, II, and III are also shown.

Appendix I contains Tables 1-13.

Sequence Listing

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-12 show the nucleic acid sequences of mutagenic primers used to generate the $K_{64}N$ mutation, $T_{76}M$ mutation, $Q_{77}R$ mutation, $G_{104}H$ mutation, $G_{106}Q$ mutation, $L_{107}K$ mutation, $E_{126}A$ mutation, $T_{226}N$ mutation, $W_{231}F$ mutation, $W_{231}L$ mutation, $H_{244}R$ mutation, and $K_{247}R$ mutation, respectively, in the pCB8D2-2J-2-9-1 DEN-2 prM/E expression plasmid.

SEQ ID NOs: 13 and 14 show the nucleic and amino acid sequences of a recombinant DEN-2 virus E-glycoprotein antigen.

SEQ ID NOs: 15 and 16 show the nucleic and amino acid sequences of a recombinant DEN-2 virus E-glycoprotein antigen incorporating the $G_{104}H$ substitution.

SEQ ID NOs: 17 and 18 show the nucleic and amino acid sequences of a recombinant DEN-2 virus E-glycoprotein antigen incorporating the $G_{106}Q$ substitution.

SEQ ID NOs: 19 and 20 show the nucleic and amino acid sequences of a recombinant DEN-2 virus E-glycoprotein antigen incorporating the $L_{107}K$ substitution.

SEQ ID NOs: 21 and 22 show the nucleic and amino acid sequences of a recombinant DEN-2 virus E-glycoprotein antigen incorporating the $E_{126}A$ substitution.

SEQ ID NOs: 23 and 24 show the nucleic and amino acid sequences of a recombinant DEN-2 virus E-glycoprotein antigen incorporating the $T_{226}N$ substitution.

SEQ ID NOs: 25 and 26 show the nucleic and amino acid sequences of a recombinant DEN-2 virus E-glycoprotein antigen incorporating the $W_{231}F$ substitution.

SEQ ID NOs: 27 and 28 show the nucleic and amino acid sequences of a recombinant DEN-2 virus E-glycoprotein antigen incorporating the $W_{231}L$ substitution.

SEQ ID NOs: 29 and 30 show the nucleic and amino acid sequences of a recombinant DEN-2 virus E-glycoprotein antigen incorporating the double $E_{126}A/T_{226}N$ substitution.

SEQ ID NOs: 31-79 show the nucleic acid sequences of mutagenic primers used to generate site-specific mutations into the SLEV and WNV E genes.

SEQ ID NOs: 80 and 81 show the nucleic and amino acid sequences of a recombinant SLEV virus E-glycoprotein antigen.

SEQ ID NOs: 82 and 83 show the nucleic and amino acid sequences of a recombinant SLEV virus E-glycoprotein antigen incorporating the $G_{106}Q$ substitution.

SEQ ID NOs: 84 and 85 show the nucleic and amino acid sequences of a recombinant WNV virus E-glycoprotein antigen.

SEQ ID NOs: 86 and 87 show the nucleic and amino acid sequences of a recombinant WNV virus E-glycoprotein antigen incorporating the $G_{106}V$ substitution.

The Sequence Listing is submitted as an ASCII text file in the form of the file named Sequence_Listing.txt, which was created on Sep. 27, 2010, and is 164,645 bytes, which is incorporated by reference herein.

Detailed Description

I. Abbreviations
ADE antibody-dependant enhancement
Ag-ELISA antigen-capture ELISA
D domain
DEN dengue
DENV dengue virus
E envelope
ELISA enzyme-linked immunoabsorbent assay
IFA indirect immuno-fluorescence assay
JE Japanese encephalitis
JEV Japanese encephalitis virus
mAb monoclonal antibody
MHIAF murine hyper-immune ascetic fluid
MVEV Murray Valley encephalitis virus
PCR polymerase chain reaction
prM premembrane
SLE St. Louis encephalitis
SLEV St. Louis encephalitis virus
TBE tick-borne encephalitis
VLP virus-like particle
WN West Nile
WNV West Nile virus
YF yellow fever II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. The materials, methods, and examples are illustrative only and not intended to be limiting.

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($k_d$), which is the concentration of Y that is required to occupy half of the binding sites of X present in a solution. A smaller ($k_d$) indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

In one example, antibody binding affinity is measured by end-point titration in an Ag-ELISA assay. Antibody binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a flavivirus antigen.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Epitope: An antigenic determinant. These are particular chemical groups, such as contiguous or non-contiguous peptide sequences, on a molecule that are antigenic, that is, that elicit a specific immune response. An antibody binds a particular antigenic epitope based on the three dimensional structure of the antibody and the matching (or cognate) three dimensional structure of the epitope.

A "cross-reactive epitope" is an epitope found in two or more antigens expressed by different genes, and responsible for inducing cross-reactive antibodies. For example, a "flavivirus cross-reactive epitope" is a flavivirus epitope found in a peptide from two or more flaviviruses, and responsible for inducing flavivirus cross-reactive antibodies.

A "substituted epitope" comprises at least one structural substitution in the epitope, such as a substitution of one amino acid for another. In certain provided embodiments, amino acid substitutions at probable or identified cross-reactive epitope residues are designed to reduce or ablate cross-reactive antibody recognition without substantially altering E-glycoprotein structural conformation or affecting type-specific antibody binding sites, disrupting dimer interactions, or impairing particle formation, maturation, or secretion.

Flavivirus cross-reactive antibody: An antibody that recognizes (that is, specifically binds to) an epitope found on a peptide from more than one species of flavivirus. Flavivirus cross-reactive antibodies are classified as either complex cross-reactive or group cross-reactive antibodies. Complex cross-reactive antibodies recognize epitopes shared by all viruses within a complex, such as the JE virus complex or the DEN virus complex. Group cross-reactive antibodies recognize epitopes shared by all members of the genus Flavivirus.

Antibody cross-reactivity is further refined within the sub-complex and sub-group cross-reactive categories. Sub-complex cross-reactive antibodies recognize epitopes shared by most, but not all, members of a particular flavivirus complex (e.g., DENV-1, -2, and -3, but not DENV-4), while sub-group cross-reactive antibodies recognize epitopes shared by flaviviruses from several complexes, but not all members of the flavivirus group (e.g., all members of the DEN virus and JE virus complexes, but not all members of the tick-borne virus complex). Specific, non-limiting examples of flavivirus cross-reactive antibodies include the group cross-reactive mAbs 4G2 and 6B6C-1, the sub-group cross-reactive mAb 1B7-5, and the sub-complex cross-reactive mAb 10A1D-2.

Flavivirus E-glycoprotein: A structural envelope protein that mediates binding of flavivirus virions to cellular receptors on host cells. The flavivirus E-glycoprotein is required for membrane fusion, and is the primary antigen inducing protective immunity to flavivirus infection. Flavivirus E-glycoprotein affects host range, tissue tropism and viral virulence. The flavivirus E-glycoprotein contains three structural and functional domains, DI-DIII. In mature virus particles the E-glycoprotein forms head to tail homodimers lying flat and forming a dense lattice on the viral surface.

Flavivirus E-glycoprotein domain: A domain of a protein is a part of a protein that shares common structural, physiochemical and/or functional features; for example hydrophobic, polar, globular, helical domains or properties, for example a DNA binding domain, an ATP binding domain, and the like. The flavivirus E-glycoprotein contains three recognized structural and functional domains, DI-DIII. DI is an 8-stranded β-barrel containing two large insertion loops that form the elongated finger-like DII. DII is involved in stabilizing the E-glycoprotein dimer and contains the internal fusion peptide that mediates flaviviral entry into host cells via membrane fusion. DIII forms a ten-stranded β-barrel with an immunoglobulin-like fold and contains the cellular receptor-binding motifs. DI and DIII contain predominately type- and subtype-specific epitopes, whereas DII contains the major flavivirus group and subgroup cross-reactive epitopes, which are sensitive to reduction and denaturation and are therefore believed to be formed from discontinuous amino acid sequences.

Flavivirus type-specific antibody: An antibody that recognizes (that is, specifically binds to) an epitope found on a peptide from only one specific member of the Flaviviruses. Specific, non-limiting examples of flavivirus type-specific antibodies include: DI mAb 9A4D-1, DII mAb 1A5D-1, and DIII mAbs 3H5, 9A3D-8 and 9D12, which only recognize epitopes found in the DENV-2 E-glycoprotein.

Hybridization: Oligonucleotides and their analogs hybridize by hydrogen bonding, which includes Watson-Crick, Hoogsteen or reversed Hoogsteen hydrogen bonding, between complementary bases. Generally, nucleic'acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune stimulatory composition: A term used herein to mean a composition useful for stimulating or eliciting a specific immune response (or immunogenic response) in a vertebrate. The immune stimulatory composition can be a protein antigen or a plasmid vector used to express a protein antigen. In some embodiments, the immunogenic response is protective or provides protective immunity, in that it enables the vertebrate animal to better resist infection with or disease progression from the organism against which the immune stimulatory composition is directed.

Without wishing to be bound by a specific theory, it is believed that an immunogenic response induced by an immune stimulatory composition may arise from the generation of an antibody specific to one or more of the epitopes provided in the immune stimulatory composition. Alternatively, the response may comprise a T-helper or cytotoxic cell-based response to one or more of the epitopes provided in the immune stimulatory composition. All three of these responses may originate from naïve or memory cells. One specific example of a type of immune stimulatory composition is a vaccine.

In some embodiments, an "effective amount" or "immunestimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Inhibiting or treating a disease: Inhibiting the full development of a disease or condition, for example, in a subject who is at risk for a disease. Specific examples of diseases include dengue fever, dengue hemorrhagic fever, yellow fever, Japanese encephalitis, tick-borne encephalitis, and West Nile disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Oligonucleotide: A nucleic acid molecule generally comprising a length of 300 bases or fewer. The term often refers to single-stranded deoxyribonucleotides, but it can refer as well to single- or double-stranded ribonucleotides, RNA:DNA hybrids and double-stranded DNAs, among others. The term "oligonucleotide" also includes oligonucleotides (that is, an oligonucleotide minus the phosphate) and any other organic base polymer.

In some examples, oligonucleotides are about 10 to about 90 bases in length, for example, 12, 13, 14, 15, 16, 17, 18, 19 or 20 bases in length. Other oligonucleotides are about 25, about 30, about 35, about 40, about 45, about 50, about 55, about 60 bases, about 65 bases, about 70 bases, about 75 bases or about 80 bases in length. Oligonucleotides may be single-stranded, for example, for use as probes or primers, or may be double-stranded, for example, for use in the construction of a mutant gene. Oligonucleotides can be either sense or anti-sense oligonucleotides. An oligonucleotide can be modified as discussed above in reference to nucleic acid molecules. Oligonucleotides can be obtained from existing nucleic acid sources (for example, genomic or cDNA), but can also be synthetic (for example, produced by laboratory or in vitro oligonucleotide synthesis).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence is the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Paratope: That portion of an antibody that is responsible for its binding to an antigenic determinant (epitope) on an antigen.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules such as glycoproteins. The term "polypeptide" is specifically intended to cover naturally occurring proteins, as well as those which are recombinantly or synthetically produced.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, $4^{th}$ ed., John Wiley & Sons, Inc., 1999.

Primers are short nucleic acid molecules, for instance DNA oligonucleotides 6 nucleotides or more in length, for example that hybridize to contiguous complementary nucleotides or a sequence to be amplified. Longer DNA oligonucleotides may be about 10, 12, 15, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Recombinant nucleic acid: A nucleic acid molecule that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Regulatory sequences or elements: These terms refer generally to a class of DNA sequences that influence or control expression of genes. Included in the term are promoters, enhancers, locus control regions (LCRs), insulators/boundary elements, silencers, matrix attachment regions (MARs, also referred to as scaffold attachment regions), repressor, transcriptional terminators, origins of replication, centromeres, and meiotic recombination hotspots. Promoters are sequences of DNA near the 5'-end of a gene that act as a binding site for DNA-dependent RNA polymerase, and from which transcription is initiated. Enhancers are control elements that elevate the level of transcription from a promoter, usually independently of the enhancer's orientation or distance from the promoter. LCRs confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also know as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. MARs are sequences within DNA that bind to the nuclear scaffold; they can affect transcription, possibly by separating chromosomes into regulatory domains. It is believed that MARs mediate higher-order, looped structures within chromosomes. Transcriptional terminators are regions within the gene vicinity where RNA Polymerase is released from the template. Origins of replication are regions of the genome, during DNA synthesis or replication phases of cell division, that begin the replication process of DNA. Meiotic recombination hotspots are regions of the genome that recombine more frequently than average during meiosis.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specific binding agent: An agent that binds substantially only to a defined target. Thus a protein-specific binding agent binds substantially only the defined protein, or to a specific region within the protein. As used herein, protein-specific binding agents include antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. Examples of suitable in vitro assays which make use of the Western blotting procedure include IFA and Ag-ELISA, and are described in many standard texts, including Harlow and Lane, *Using Antibodies: A Laboratory Manual*, CSHL, New York, 1999.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

III. Overview of Several Embodiments

Isolated mutant flavivirus polypeptides exhibiting measurably reduced antibody cross-reactivity (compared to corresponding wild-type polypeptides) are disclosed herein. In one embodiment, the isolated flavivirus polypeptides are flavivirus E-glycoproteins that include an amino acid sequence as shown in SEQ ID NO: 14, wherein at least one of the amino acids at position 104, 106, 107, 126, 226, or 231 is substituted (compared to corresponding wild-type E-glycoproteins). Specific, non-limiting examples of the amino acid substitutions at positions 104, 106, 107, 126, 226, and 231 include: $G_{104}H$ (SEQ ID NO: 16), $G_{106}Q$ (SEQ ID NO: 18), $L_{107}K$ (SEQ ID NO: 20), $E_{126}A$ (SEQ ID NO: 22), $T_{226}N$ (SEQ ID NO: 24), $W_{231}F$ (SEQ ID NO: 26), and $W_{231}L$ (SEQ ID NO: 28). Also disclosed are isolated nucleic acid molecules encoding the flavivirus polypeptides with at least one amino acid substitution at position 104, 106, 107, 126, 226, or 231 of SEQ ID NO: 14. Representative nucleic acid molecules are shown in SEQ ID NOs: 15, 17, 19, 21, 23, 25, and 27.

In another embodiment, the isolated flavivirus polypeptides are flavivirus E-glycoproteins that include an amino acid sequence as shown in SEQ ID NO: 81, wherein at least one of the amino acids at position 106 is substituted (compared to corresponding wild-type E-glycoproteins). Specific, non-limiting examples of the amino acid substitutions at position 106 include: $G_{106}Q$ (SEQ ID NO: 83). Also disclosed are isolated nucleic acid molecules encoding the flavivirus polypeptides with at least one amino acid substitution at position 106 of SEQ ID NO: 81. A representative nucleic acid molecule is shown in SEQ ID NO: 82.

In yet another embodiment, the isolated flavivirus polypeptides are flavivirus E-glycoproteins that include an amino acid sequence as shown in SEQ ID NO: 85, wherein at least one of the amino acids at position 106 is substituted (compared to corresponding wild-type E-glycoproteins). Specific, non-limiting examples of the amino acid substitutions at position 106 include: $G_{106}V$ (SEQ ID NO: 87). Also disclosed are isolated nucleic acid molecules encoding the flavivirus polypeptides with at least one amino acid substitution at position 106 of SEQ ID NO: 85. A representative nucleic acid molecule is shown in SEQ ID NO: 86.

Pharmaceutical and immune stimulatory compositions are also disclosed that include one or more flavivirus E-glycoprotein polypeptides exhibiting measurably reduced antibody cross-reactivity, with at least one amino acid substitution at position 104, 106, 107, 126, 226, or 231 of SEQ ID NO: 14. Also disclosed are pharmaceutical and immune stimulatory compositions that include one or more nucleic acid molecules encoding the flavivirus polypeptides with at least one amino acid substitution at position 104, 106, 107, 126, 226, or 231 of SEQ ID NO: 14. Representative nucleic acid molecules are shown in SEQ ID NOs: 15, 17, 19, 21, 23, 25, and 27.

Also disclosed are pharmaceutical and immune stimulatory compositions that include one or more flavivirus E-glycoprotein polypeptides exhibiting measurably reduced antibody cross-reactivity, with at least one amino acid substitution at position 106 of SEQ ID NO: 81 or SEQ ID NO: 85. Also disclosed are pharmaceutical and immune stimulatory compositions that include one or more nucleic acid molecules encoding the flavivirus polypeptides with at least one amino acid substitution at position 106 of SEQ ID NO: 81 or SEQ ID NO: 85. Representative nucleic acid molecules are shown in SEQ ID NOs: 82 and 86.

In another embodiment, a method is provided for identifying and modifying a flavivirus cross-reactive epitope. This method includes selecting a candidate cross-reactive epitope using a structure-based design approach, and designing a substituted epitope including at least one amino acid residue substitution compared to the candidate epitope. The candidate epitope is then contacted with a specific binding agent under conditions whereby a candidate epitope/specific binding agent complex can form. Likewise, the substituted epitope is contacted with the same specific binding agent under the same conditions used for candidate epitope/specific binding agent complex formation. A candidate epitope is identified as a flavivirus cross-reactive epitope when the substituted epitope has a substantially lower binding affinity for the specific binding agent compared to the candidate epitope, and wherein the flavivirus cross-reactive epitope binds to a specific binding agent that binds to at least two flaviviruses. In specific, non-limiting examples, the at least two flaviviruses are selected from dengue serotype I virus, dengue serotype 2 virus, dengue serotype 3 virus, dengue serotype 4 virus, yellow fever virus, Japanese encephalitis virus, St. Louis encephalitis virus, and West Nile virus. In yet another specific example of the provided method, the specific binding agent is a flavivirus cross-reactive antibody.

In a further specific example of the provided method, the structure-based design approach includes identifying at least one conserved flavivirus amino acid between two or more flavivirus groups or subgroups, and mapping the conserved flavivirus amino acid onto a structure of a flavivirus E-glycoprotein. In another specific example, the conserved flavivirus amino acid exhibits two or more of the following structural characteristics: it is located in DII of the E-glycoprotein, it is conserved across the flaviviruses, it is on the outer or lateral surface of the E-glycoprotein dimer, it has at least 35% surface accessibility potential, its side chain projection is accessible for antibody paratopes, or it has a high β-factor.

In yet a further specific example of the provided method, the structure-based design approach includes identifying at least one conserved flavivirus amino acid between two or more flavivirus complexes or subcomplexes, and mapping the conserved flavivirus amino acid onto a structure of a flavivirus E-glycoprotein. In still another specific example, the conserved flavivirus amino acid exhibits two or more of the following structural characteristics: it has at least 35% surface accessibility potential, it is on the outer or lateral surface of the E-glycoprotein dimer, it is conserved across the flaviviruses, its side chain projection is accessible for antibody paratopes, or it has a high β-factor.

In another embodiment, a method is provided for detecting a flavivirus antibody in a sample. This method includes contacting the sample with the disclosed mutant flavivirus polypeptides under conditions whereby a polypeptide/antibody complex can form, and detecting polypeptide/antibody complex formation, thereby detecting a flavivirus antibody in a sample. Also disclosed are methods of diagnosing a flavivirus infection in a subject. In one embodiment, the method includes contacting a sample from the subject with the disclosed mutant flavivirus polypeptides under conditions whereby a polypeptide/antibody complex can form, and detecting polypeptide/antibody complex formation, thereby diagnosing a flavivirus infection in a subject.

Also disclosed is a flavivirus E-glycoprotein engineered to comprise at least one amino acid residue substitution according to the methods described herein.

IV. Identifying Flavivirus Cross-Reactive Epitopes

The current disclosure provides methods for identifying flavivirus cross-reactive epitopes, as well as distinguishing such epitopes from species-specific (or type-specific) epitopes.

In one embodiment, the method comprises a structure-based design approach, which optionally includes one or more of the following requirements in order to identify cross-reactive epitopes: 1) the epitope is located in DII of the E-glycoprotein, for example, amino acids 52-135 and 195-285 in the TBE virus E-glycoprotein, 52-132 and 193-280 in the DEN-2 virus E-glycoprotein, and conserved across the flaviviruses or multiple flaviviral species; 2) the epitope is on the outer or lateral surface of the E-glycoprotein dimer; 3) the epitope has at least 35% surface accessibility potential; 4) one or more side chain projections of amino acids within the epitope are accessible to antibody paratopes; and 5) residues with high temperature (β) factors are favored.

In one embodiment, a structure-based design approach comprises a procedural algorithm developed to localize epitopes responsible for inducing flavivirus cross-reactive antibodies. Strictly-conserved flavivirus residues are initially identified. These residues are mapped, for example, onto a 2.0 Å resolution E-glycoprotein structure for TBE virus (Rey et al., *Nature* 375:291-98, 1995), a high resolution DEN-2 virus E-glycoprotein structure (Modis et al., *PNAS* 100:6986-91, 2003), or other similar structure. Optionally, strictly-conserved flavivirus residues are also mapped onto a computer predicted homology model structure for the DEN-2 virus E-glycoprotein using, for example, the Swiss-Pdb Viewer 3.7 structure analysis software (Guex et al., *Electrophoresis* 18:2714-23, 1997).

The following criteria (individually or in combination of two or more) are then employed in certain embodiments to select probable flavivirus group or subgroup cross-reactive epitope residues: 1) an amino acid located in DII (for example, amino acids 52-135 and 195-285 in the TBE virus E-glycoprotein (Rey et al., *Nature* 375:291-98, 1995); 52-132 and 193-280 in the DEN-2 virus E-glycoprotein (Modis et al., *PNAS* 100:6986-91, 2003)), and conserved among more than one flavivirus; 2) amino acids on the outer or lateral surface of the E-glycoprotein dimer; 3) amino acids with at least 35% surface accessibility potential; 4) side chain projections accessible to antibody paratopes; and 5) residues with high temperature ($\beta$) factors should be favored, as these residues tend to be flexible and are able to conform to the antibody paratope, increasing the antibody-antigen (Ab-Ag) affinity.

Similar criteria (individually or in combination of two or more) are employed in certain embodiments to select probable flavivirus complex or subcomplex cross-reactive epitope residues. The procedural algorithm for the identification of flavivirus complex and sub-complex cross-reactive epitopes utilizes the following optimality criteria: 1) The identification and selection of amino acid residues with ≥35% of their surface solvent accessible. These residues are identified from the published atomic structure coordinates of the DENV-2 soluble ectodomain of the envelope glycoprotein and homology models of SLEV and WNV derived from the DENV-2 structure (Modis et al., *Proc. Natl. Acad. Sci. USA* 100:6986-91, 2003). In addition to examination of amino acid residues in structural domain II, residues in domains I and III were examined, since published results indicate that some complex and sub-complex cross-reactive epitopes are mapped onto domains I and III in addition to domain II (Roehrig et al., *Virology* 246:317-28, 1998). 2) Amino acids on the outer or lateral surface of the E-glycoprotein dimer, and accessible to antibody. 3) Amino acid conservation across the flavivirus complex (based upon a structural alignment of the protein sequences). Residues conserved across all member viruses of the same complex are favored. If conserved within but not across the entire complex, then residues with shared identities between WNV and SLEV are favored in the JEV complex, and residues with shared identities between DENV-2 and two or more other viruses in the DENV complex are favored over those shared with DENV-2 and only one other DENV complex virus. 4) Side chain projections exposed towards the outer surface and accessible to antibody paratopes. 5) Residues with high temperature ($\beta$-) factors should be favored, as these residues tend to be flexible and are able to conform to the antibody paratope, increasing the antibody-antigen affinity. Amino acid residues with high temperature factors are more commonly found in antigen epitopes than lower temperature factor residues. 6) Following identification of potential individual flavivirus complex and sub-complex cross-reactive epitope residues, all residues are mapped and highlighted on the same E-glycoprotein dimer structure together. With this technique, groups of potential cross-reactive epitope residues forming clusters (and hence probable epitopes) are readily identified. 7) Residues fitting all of these criteria and occurring in structural clusters approximately 20×30 Å$^2$ (which is the average "footprint" of an antibody Fab that interacts with an antigen epitope) are favored over residues that are more isolated in the protein structure. 8) Within an identified structural cluster of potential epitope residues, residues that more completely satisfy greater numbers of the optimality criteria are selected for the first round of mutagenesis analysis.

A. Outer and/or Lateral Surface Amino Acids

In one embodiment, the outer and/or lateral surface of the E-glycoprotein dimer comprises those residues which are exposed on the surface of the E-glycoprotein dimer in a way that they are physically capable of interacting with a host-derived immunoglobulin antibody molecule. The flavivirus virion contains a host cell-derived lipid bilayer, with E-glycoprotein dimers imbedded within this lipid bilayer via their trans-membrane domains. The ectodomains of the E-glycoprotein dimers lie on top of this bilayer, forming a dense lattice and essentially coating the virion in a protein shell. Because of this structural organization, there are regions of the E-glycoprotein that, under general assembled virion conditions, cannot physically interact with an immunoglobulin molecule, and therefore are highly unlikely to form part of an antibody epitope. Such inaccessible regions include the trans-membrane domains (because they are imbedded within the lipid bilayer and are covered by the ectodomain) and more than two-thirds of the residues of the ectodomain itself, which are either on the bottom surface of the dimer (and therefore packed between the lipid layer and the ectodomain), or are packed into the interior of this globular protein rather than on its surface. Because of these structural constraints, under normal conditions immunoglobulin molecules can only interact with residues on the outer exposed surface of the E-glycoprotein dimer, and with a subset of residues on the outer lateral surface. Because of the close packing of E-glycoprotein dimers into a network across the surface of the virion, and the difficulty of a large immunoglobulin molecule accessing these narrow spaces, it is believed that only some of the lateral surface residues are available for immunoglobulin interaction. For these reasons, only residues located on the outer or lateral surface of the E-glycoprotein are considered as participating in possible flavivirus cross-reactive epitopes. An inspection of the location of a residue (e.g., a residue conserved among more than one flavivirus, such as $Gly_{104}$, $Gly_{106}$, $Leu_{107}$, or $Trp_{231}$) in the E-glycoprotein dimer atomic structure allows for a determination as to whether or not a residue is located on the outer or lateral surface of the dimer.

B. Surface Accessibility Potential

In one embodiment, surface accessibility potential comprises that portion of the predicted electron density surrounding any amino acid residue's side chain that is exposed on the surface of the protein, and theoretically available to interact with another molecule. For any given "surface" residue, its surface accessibility is affected by the local (and surrounding) secondary structure of the alpha-carbon main chain, and the positions and types of immediately surrounding side-chain projections. Thus, by definition, maximum accessibility would be for a residue X in the peptide GGXGG in an extended conformation, as the glycine residues have no side chains and therefore amino acid X's surface accessibility is not constrained by either the alpha-carbon backbone shape or the surrounding residues' side chain projections (see, e.g., Li et al., *Nature Struct. Bio.* 10:482-88, 2003; and Faelber et al., *J. Mol. Biol.* 313:83-97, 2001).

C. Accessible Side Chain Projections

In one embodiment, the side chain projection(s) accessible for antibody paratopes comprises a qualitative assessment of how exposed and/or available a given amino acid's reactive side chain is to interact with a hypothetical immunoglobulin molecule. The angle of projection of a side chain is determined primarily by its position in the primary amino acid chain. However, upon folding of this polypeptide chain, the side chain projections are additionally altered or affected by electrostatic and other forces from surrounding residues. The accessibility of an amino acid's side chain projections to be bound by antibody is a specific criterion that is inherent in an amino acid's "surface accessibility." Hence, theoretical amino acid X could have 50% surface accessibility and yet its side-chain may still be directed towards the interior of the protein and therefore be unlikely to interact energetically with an immunoglobulin molecule (see, e.g., Li et al., *Nature Struct. Bio.* 10:482-88, 2003; Faelber et al., *J. Mol. Biol.* 313:83-97, 2001; and Eyal et al., *J. Comp. Chem.* 25: 712-24, 2003).

D. High Temperature Factors

In one embodiment, a temperature or β-factor comprises a criterion which represents a particular amino acid's potential flexibility within the protein. Any given atom within a protein structure is defined by four parameters, the three x, y and z coordinates, defining its position in space, and its β- or temperature factor. For well defined, high-resolution crystal structures, β-values are typically ≤20 Å$^2$. High β-values, for example, ≥40 Å$^2$ can be a signal that there is little confidence in the assignment of these atoms within the protein (for example, if the protein is disordered and does not consistently fold into the same structure). However, in well-defined atomic-level resolution protein structures, high β-factors associated with particular atoms for individual amino acids are typically interpreted as indicators of that residue or atom's potential flexibility. This criterion is relevant to epitope determination, as shape complementarity of the molecular surfaces of both the antibody paratope and the antigen epitope is know to be an important factor effecting antibody avidity. Flexible residues, identified by their higher β-factors, are better able to make slight positional adjustments, thereby improving shape complementarity and the energetics of the Ag-Ab interaction. It has been demonstrated that epitope amino acids involved in antibody interactions are more likely to have high β-factors than are amino acids from the same protein that do not interact with antibodies (see, e.g., Mylvaganam et al., *J. Mol. Biol.* 281:301-22, 1998).

Amino acid substitutions at probable cross-reactive epitope residues are modeled, selecting substitutions that should reduce or ablate antibody recognition without altering E-glycoprotein structural conformation, disrupting dimer interactions, or impairing particle formation, maturation, or secretion. For this reason, cysteine residues otherwise satisfying the cross-reactive epitope criteria are not recommended for mutagenesis because their involvement in disulphide bridging is believed to be necessary for proper E-glycoprotein structure and function (Modis et al., *PNAS* 100:6986-91, 2003; Rey et al., *Nature* 375:291-98, 1995). Stability calculations are performed for all possible amino acid substitutions of candidate residues using, for example, the FOLD-X server (Guerois et al., *J. Mol. Biol.* 320:369-87, 2002; available on the internes) and the TBE virus E-glycoprotein pdb file coordinates (Rey et al., *Nature* 375:291-98, 1995). By way of example, amino acid substitutions modeled in the TBE virus E-glycoprotein with free energies of folding equal to or less than that of the non-mutated wild-type E-glycoprotein are re-examined with the Swiss-PdbViewer software, to identify those substitutions that minimized local structural disturbances while maintaining structurally relevant biochemical interactions such as hydrogen bonding and/or charge interactions with neighboring amino acids.

Optionally, upon the successful identification of cross-reactive epitope residues, the E-glycoprotein structure can be further analyzed to identify additional residues forming cross-reactive epitopes. By way of example, a "nearest neighbor" search is conducted of the surface of the E-glycoprotein structure, looking for additional residues located within 10-15 Å of the identified residue. This distance is within the binding footprint of a single antibody paratope (Faebler et al., *J. Mol. Biol.* 313:83-97, 2001). In this second iteration of cross-reactive epitope residue identification, the same five optimality criterion as above are used, with one change. The criterion of strict conservation across the flaviviruses is relaxed to now include variable residues. In this way, residues either conserved in their physiochemical nature and/or conserved only within a particular flavivirus complex (such as the four DEN serotypes) or subgroup can be identified.

Also provided are methods for designing a substituted epitope comprising at least one amino acid residue substitution compared to a wild-type candidate epitope; obtaining a first sample comprising the candidate epitope; obtaining a second sample comprising the substituted epitope; contacting the first sample with a specific binding agent; and contacting the second sample with the specific binding agent, wherein the cross-reactive epitope is identified when the substituted epitope has a substantially lower binding affinity for the specific binding agent compared to the candidate epitope. Antibody binding affinities can be determined by many methods well known in the art, such as end-point titration in an Ag-ELISA assay, competition binding in an ELISA assay, a solid-phase radioimmunoassay, and the Biacore® surface plasmon resonance technique (Malmqvist, *Biochem. Soc. Trans.* 27:335-40, 1999; and Drake et al., *Anal. Biochem.* 328:35-43, 2004).

In some embodiments the specific binding agent is an antibody, for example, a polyclonal antibody or a mAb. A specific, non-limiting example of a polyclonal antibody is polyclonal anti-DEN-2 MHIAF. Specific, non-limiting examples of mAbs include 4G2 (ATCC No. HB-112), 6B6C-1, 1B7-5, 10A1D-2, 1A5D-1, and 1B4C-2 (Roehrig et al., *Virology* 246:317-28, 1998).

V. Flavivirus Cross-Reactive Epitopes and Variants Thereof

The disclosure also provides an isolated polypeptide comprising at least one flavivirus cross-reactive epitope residue, wherein the antibody cross-reactivity of the at least one flavivirus cross-reactive epitope has been reduced or ablated. In one embodiment, one or more amino acid substitutions of one or more flavivirus cross-reactive epitope residues causes the reduction or ablation of antibody cross-reactivity. In another embodiment, the at least one flavivirus cross-reactive epitope residue with reduced or ablated cross-reactivity has measurably lower binding affinity with one or more flavivirus group-reactive mAbs, due to substitution of the flavivirus cross-reactive epitope residue(s), but its binding with one or more DEN-2 virus type-specific mAbs is not affected.

Specific, non-limiting examples of an isolated polypeptide comprising at least one flavivirus cross-reactive epitope residue with reduced or ablated cross-reactivity include, the amino acid sequences shown in SEQ ID NO: 16 ($G_{104}H$), SEQ ID NO: 18 ($G_{106}Q$), SEQ ID NO: 20 ($L_{107}K$), SEQ ID NO: 22 ($E_{126}A$), SEQ ID NO: 24 ($T_{226}N$), SEQ ID NO: 26 ($W_{231}F$), SEQ ID NO: 28 ($W_{231}L$), SEQ ID NO: 30 ($E_{126}A/T_{226}N$), SEQ ID NO: 83, and SEQ ID NO: 87.

Manipulation of the nucleotide sequence of a flavivirus cross-reactive epitope using standard procedures, including for instance site-directed mutagenesis or PCR and M13 primer mutagenesis, can be used to produce variants with reduced or ablated cross-reactivity. Details of these techniques are provided in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989. The simplest modifications involve the substitution of one or more amino acids for amino acids having similar physiochemical and/or structural properties. These so-called conservative substitutions are likely to have minimal impact on the activity and/or structure of the resultant protein. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Substitutions that should reduce or ablate antibody recognition without altering E-glycoprotein structural conformation, disrupting dimer interactions, or impairing particle formation, maturation, or secretion include: Gly to His, Gly to Gln, Leu to Lys, Glu to Ala, Thr to Asn, Trp to Phe, and Trp to Leu.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

The disclosure also provides isolated nucleic acids that encode the described polypeptides. Nucleic acids of the invention thus include nucleic acids that encode: 1) polypeptides comprising at least one flavivirus cross-reactive epitope with reduced or ablated cross-reactivity; and 2) polypeptides that that are at least 95% identical to the polypeptides comprising at least one flavivirus cross-reactive epitope with reduced or ablated cross-reactivity.

Recombinant nucleic acids may, for instance, contain all or part of a disclosed nucleic acid operably linked to a regulatory sequence or element, such as a promoter, for instance, as part of a clone designed to express a protein. Cloning and expression systems are commercially available for such purposes and are well known in the art. The disclosure also provides cells or organisms transformed with recombinant nucleic acid constructs that encode all or part of the described polypeptides. Also disclosed are virus-like particles (VLPs) that include one or more of the described flavivirus E-glycoprotein polypeptides.

VI. Specific Binding Agents

This disclosure provides specific binding agents that bind to polypeptides disclosed herein, e.g., flavivirus E-glycoprotein polypeptides with reduced or ablated cross-reactivity. The binding agent may be useful for identifying flavivirus cross-reactive epitopes, and for detecting and purifying polypeptides comprising flavivirus cross-reactive epitopes. Examples of the binding agents are a polyclonal or monoclonal antibody, and fragments thereof, that bind to polypeptides disclosed herein. A specific, non-limiting example of a polyclonal antibody is polyclonal anti-DEN-2 MHIAF. Specific, non-limiting examples of mAbs include 4G2, 6B6C-1, 1B7-5, 10A1D-2, 1A5D-1, and 1B4C-2.

Monoclonal or polyclonal antibodies can be raised to recognize the polypeptides described herein, or variants thereof. Optimally, antibodies raised against these polypeptides will specifically detect the polypeptide with which the antibodies are generated. That is, antibodies raised against the polypeptide will recognize and bind the polypeptide, and will not substantially recognize or bind to other polypeptides or antigens. The determination that an antibody specifically binds to a target polypeptide is made by any one of a number of standard immunoassay methods; for instance, the Western blotting technique (Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1.989), Ag-ELISA and IFA.

Substantially pure flavivirus recombinant polypeptide antigens suitable for use as immunogens can be isolated from the transformed cells described herein, using methods well known in the art. Monoclonal or polyclonal antibodies to the antigens can then be prepared.

Monoclonal antibodies to the polypeptides can be prepared from murine hybridomas according to the classic method of Kohler & Milstein (*Nature* 256:495-97, 1975), or a derivative method thereof. Briefly, a mouse is repetitively inoculated with a few micrograms of the selected protein immunogen (for example, a polypeptide comprising at least one flavivirus cross-reactive epitope with reduced or ablated cross-reactivity, a portion of a polypeptide comprising at least one flavivirus cross-reactive epitope with reduced or ablated cross-reactivity, or a synthetic peptide comprising at least one flavivirus cross-reactive epitope with reduced or ablated cross-reactivity) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microliter plate where growth of the culture is continued. Antibody-producing clones are identified by detection of antibody in the supernatant fluid of the wells by immunoassay procedures, such as ELISA, as originally described by Engvall (*Meth. Enzymol.*, 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual*, CSHL, New York, 1999.

Polyclonal antiserum containing antibodies can be prepared by immunizing suitable animals with a polypeptide comprising at least one flavivirus cross-reactive epitope with reduced or ablated cross-reactivity, a portion of a polypeptide comprising at least one flavivirus cross-reactive epitope with reduced or ablated cross-reactivity, or a synthetic peptide comprising at least one flavivirus cross-reactive epitope with reduced or ablated cross-reactivity, which can be unmodified or modified, to enhance immunogenicity.

Effective antibody production (whether monoclonal or polyclonal) is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.*, 33:988-91, 1971).

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., *Handbook of Experimental Immunology*, Wier, D. (ed.), Chapter 19, Blackwell, 1973. A plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178:476-96, 1989; Glockshuber et al., *Biochemistry* 29:1362-67, 1990; and U.S. Pat. No. 5,648,237 (Expression of Functional Antibody Fragments); U.S. Pat. No. 4,946,778 (Single Polypeptide Chain Binding Molecules); and U.S. Pat. No. 5,455,030 (Immunotherapy Using Single Chain Polypeptide Binding Molecules), and references cited therein. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., *Current Protocols in Immunology*, Wiley, NY, 1995), agglutination assays, flocculation assays, cell panning, etc., as are well known to one of skill in the art.

Binding agents of this disclosure can be bound to a substrate (for example, beads, tubes, slides, plates, nitrocellulose sheets, etc.) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $^{32}P$, $^{125}I$, $^{35}S$), an enzyme moiety (for example, horseradish peroxidase, alkaline phosphatase), a colloidal gold moiety, and a biotin moiety. Such conjugation techniques are standard in the art (for example, see Harlow and Lane, *Using Antibodies: A Laboratory Manual*, CSHL, New York, 1999; Yang et al., *Nature*, 382:319-24, 1996).

VII. Detection of Flavivirus Antibodies

The present disclosure further provides a method of detecting a flavivirus-reactive antibody in a sample, comprising contacting the sample with a polypeptide or peptide of this disclosure under condition whereby an antibody/polypeptide complex can form; and detecting formation of the complex, thereby detecting flavivirus antibody in a sample.

The method of detecting flavivirus-reactive antibody in a sample can be performed, for example, by contacting a fluid or tissue sample from a subject with a polypeptide of this disclosure and detecting the binding of the polypeptide to the antibody. A fluid sample of this method can comprise any biological fluid which could contain the antibody, such as cerebrospinal fluid, blood, bile plasma, serum, saliva and urine. Other possible examples of body fluids include sputum, mucus and the like.

Enzyme immunoassays such as IFA, ELISA and immunoblotting can be readily adapted to accomplish the detection of flavivirus antibodies according to the methods of this disclosure. An ELISA method effective for the detection of the antibodies can, for example, be as follows: 1) bind the polypeptide to a substrate; 2) contact the bound polypeptide with a fluid or tissue sample containing the antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

Another immunologic technique that can be useful in the detection of flavivirus antibodies uses mAbs for detection of antibodies specifically reactive with flavivirus polypeptides in a competitive inhibition assay. Briefly, a sample is contacted with a polypeptide of this invention which is bound to a substrate (for example, a 96-well plate). Excess sample is thoroughly washed away. A labeled (for example, enzyme-linked, fluorescent, radioactive, etc.) mAb is then contacted with any previously formed polypeptide-antibody complexes and the amount of mAb binding is measured. The amount of inhibition of mAb binding is measured relative to a control (no antibody), allowing for detection and measurement of antibody in the sample. The degree of mAb binding inhibition can be a very specific assay for detecting a particular flavivirus variety or strain, when based on mAb binding specificity for a particular variety or strain of flavivirus. mAbs can also be used for direct detection of flavivirus in cells by, for example, IFA according to standard methods.

As a further example, a micro-agglutination test can be used to detect the presence of flavivirus antibodies in a sample. Briefly, latex beads, red blood cells or other agglutinable particles are coated with a polypeptide of this disclosure and mixed with a sample, such that antibodies in the sample that are specifically reactive with the antigen crosslink with the antigen, causing agglutination. The agglutinated polypeptide-antibody complexes form a precipitate, visible with the naked eye or measurable by spectrophotometer.

In yet another example, a microsphere-based immunoassay can be used to detect the presence of flavivirus antibodies in a sample. Briefly, microsphere beads are coated with a polypeptide of this disclosure and mixed with a sample, such that antibodies in the sample that are specifically reactive with the antigen bind the antigen. The bead-bound polypeptide-antibody complexes are allowed to react with fluorescent-dye labeled anti-species antibody (such as FITC-labeled goat anti-human IgM), and are measured using a microsphere reader (such as a Luminex instrument).

The present disclosure further provides a method of diagnosing a flavivirus infection in a subject, comprising contacting a sample from the subject with the polypeptide of this disclosure under conditions whereby an antibody/polypeptide complex can form; and detecting antibody/polypeptide complex formation, thereby diagnosing a flavivirus infection in a subject.

In examples of the diagnostic methods, the polypeptide of this disclosure can be bound to a substrate and contacted with a fluid sample such as blood, serum, urine or saliva. This sample can be taken directly from the patient or in a partially purified form. In this manner, antibodies specific for the polypeptide (the primary antibody) will specifically react with the bound polypeptide. Thereafter, a secondary antibody bound to, or labeled with, a detectable moiety can be added to enhance the detection of the primary antibody. Generally, the secondary antibody will be selected for its ability to react with multiple sites on the primary antibody. Thus, for example, several molecules of the secondary antibodies can react with each primary antibody, making the primary antibody more detectable.

The detectable moiety allows for visual detection of a precipitate or a color change, visual detection by microscopy, or automated detection by spectrometry, radiometric measurement or the like. Examples of detectable moieties include fluorescein, rhodamine, Cy5, and Cy3 (for fluorescence microscopy and/or the microsphere-based immunoassay), horseradish peroxidase (for either light or electron microscopy and biochemical detection), biotin-streptavidin (for light or electron microscopy) and alkaline phosphatase (for biochemical detection by color change).

VIII. Pharmaceutical and Immune Stimulatory Compositions and Uses Thereof

Pharmaceutical compositions including flavivirus nucleic acid sequences or flavivirus polypeptides comprising at least one flavivirus cross-reactive epitope with reduced or ablated cross-reactivity are also encompassed by the present disclosure. These pharmaceutical compositions include a therapeutically effective amount of one or more active compounds, such as flavivirus polypeptides comprising at least one flavivirus cross-reactive epitope with reduced or ablated cross-reactivity, or one or more nucleic acid molecules encoding these polypeptides, in conjunction with a pharmaceutically acceptable carrier. It is contemplated that in certain embodiments, flavivirus nucleic acid sequences or flavivirus polypeptides comprising multiple flavivirus cross-reactive epitopes with reduced or ablated cross-reactivity will be useful in preparing the pharmaceutical compositions of the disclosure.

Disclosed herein are substances suitable for use as immune stimulatory compositions for the inhibition or treatment of a flavivirus infection, for example, a dengue virus infection. In one embodiment, an immune stimulatory composition contains a flavivirus polypeptide including at least one flavivirus cross-reactive epitope with reduced or ablated cross-reactivity. In a further embodiment, the immune stimulatory composition contains a nucleic acid vector that includes flavivirus nucleic acid molecules described herein, or that includes a nucleic acid sequence encoding at least one flavivirus cross-reactive epitope with reduced or ablated cross-reactivity. In a specific, non-limiting example, a nucleic acid sequence encoding at least one flavivirus cross-reactive epitope with reduced or ablated cross-reactivity is expressed in a transcriptional unit, such as those described in published PCT Application Nos. PCT/US99/12298 and PCT/US02/10764 (both of which are incorporated herein in their entirety).

The provided immune stimulatory flavivirus polypeptides, constructs or vectors encoding such polypeptides, are combined with a pharmaceutically acceptable carrier or vehicle for administration as an immune stimulatory composition to human or animal subjects. In a particular embodiment, the immune stimulatory composition administered to a subject directs the synthesis of a mutant flavivirus E-glycoprotein as described herein, and a cell within the body of the subject, after incorporating the nucleic acid within it, secretes VLPs comprising the mutant E-glycoprotein with reduced or ablated cross-reactivity. It is believed that such VLPs then serve as an in vivo immune stimulatory composition, stimulating the immune system of the subject to generate protective immunological responses. In some embodiments, more than one immune stimulatory flavivirus polypeptide, construct or vector may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid sequence encoding a flavivirus polypeptide comprising at least one flavivirus cross-reactive epitope with reduced or ablated cross-reactivity may be utilized in such DNA vaccination methods.

Thus, the term "immune stimulatory composition" as used herein also includes nucleic acid vaccines in which a nucleic acid molecule encoding a flavivirus polypeptide comprising at least one flavivirus cross-reactive epitope with reduced or ablated cross-reactivity is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264: 16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., Proc. Natl. Acad. Sci. 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 μg to about 1 mg, with some embodiments having a range of about 10 μg to about 800 μg, and still other embodiments a range of from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

It is also contemplated that the provided immunostimulatory molecules and compositions can be administered to a subject indirectly, by first stimulating a cell in vitro, which stimulated cell is thereafter administered to the subject to elicit an immune response. Additionally, the pharmaceutical or immune stimulatory compositions or methods of treatment may be administered in combination with other therapeutic treatments.

IX. Kits

Also provided herein are kits useful in the detection and/or diagnosis of flaviviruses. An example of an assay kit provided herein is a recombinant flavivirus polypeptide (or fragment thereof) as an antigen and an enzyme-conjugated anti-human antibody as a second antibody. Examples of such kits also can include one or more enzymatic substrates. Such kits can be used to test if a sample from a subject contains antibodies against a flavivirus-specific protein. In such a kit, an appropriate amount of a flavivirus polypeptide (or fragment thereof) is provided in one or more containers, or held on a substrate. A flavivirus polypeptide can be provided in an aqueous solution or as a freeze-dried or lyophilized powder, for instance. The container(s) in which the flavivirus polypeptide(s) are supplied can be any conventional container that is capable of holding the supplied form, for instance, microfuge tubes, ampoules, or bottles.

The amount of each polypeptide supplied in the kit can be any appropriate amount, and can depend on the market to which the product is directed. For instance, if the kit is adapted for research or clinical use, the amount of each polypeptide provided would likely be an amount sufficient for several assays. General guidelines for determining appropriate amounts can be found, for example, in Ausubel et al. (eds.), *Short Protocols in Molecular Biology*, John Wiley and Sons, New York, N.Y., 1999 and Harlow and Lane, *Using Antibodies: A Laboratory Manual*, CSHL, New York, 1999.

The subject matter of the present disclosure is further illustrated by the following non-limiting Examples.

EXAMPLE 1

Identification of DII Cross-Reactive Epitope Residues

This example demonstrates the identification of flavivirus cross-reactive epitopes using a structure-based rational mutagenesis method.

Cell Culture, Virus Strain and Recombinant Plasmid

COS-1 cells (ATCC CRL 1650; Manassas, Va.) were grown at 37° C. with 5% $CO_2$ on Dulbecco's modified Eagle's minimal essential medium (DMEM, GIBCO, Grand Island, N.Y.) supplemented with 10% heat-inactivated fetal bovine serum (FBS, Hyclone Laboratories, Inc., Logan, Utah), 110 mg/l sodium pyruvate, 0.1 mM nonessential amino acids, 2 mM L-glutamine, 20 ml/l 7.5% $NaHCO_3$, 100 U/ml penicillin, and 100 μg/ml streptomycin. CHO cells (ATCC CCL 61; Manassas, Va.) were grown under the same conditions as COS-1 cells with DMEM/F12 nutrient mixture (GIBCO, Grand Island, N.Y.).

Flavivirus plasmids capable of expressing extracellular VLPs composed of prM/M and E-glycoproteins for JE, WN, SLE, and the four DEN virus serotypes have been constructed (Chang et al., *J. Virol.* 74:4244-52, 2000; Chang et al., *Virology* 306:170-80, 2003; Davis et al., *J. Virol.* 75:4040-47, 2001). These VLPs, produced by recombinant plasmid-transformed eukaryotic cells, contain the flavivirus prM/M and E-glycoproteins in their native viral conformations, and although non-infectious, they maintain many of the same properties as mature virus particles including, hemagglutination activity, membrane fusion, and the induction of protective immune responses in animals (Chang et al., *J. Virol.* 74:4244-52, 2000; Chang et al., *Virology* 306:170-80, 2003; Davis et al., *J. Virol.* 75:4040-47, 2001; Hunt, et al., *J. Virol. Methods* 97:133-49, 2001).

The recombinant expression plasmid pCB8D2-2J-2-9-1 (the DEN-2 prM/E expression plasmid, Chang et al., *Virology* 306:170-80, 2003) was used as the template DNA for both site-directed mutagenesis and for transient expression of DEN-2 recombinant antigen (see below). This plasmid includes the human cytomegalovirus early gene promoter, Kozak sequence, JE virus signal sequence, DEN-2 virus prM/M gene, DEN-2 virus chimeric E gene (with amino-terminal 80% from DEN-2 virus and carboxy-terminal 20% from JE virus), and bovine growth hormone poly(A) signal. The replacement of the terminal 20% of DEN-2 virus E gene sequences with JE virus E gene sequences dramatically increases the secretion of extracellular VLPs into the culture medium without altering the native DEN-2 virus E-glycoprotein conformation (Chang et al., *Virology* 306:170-80, 2003).

Procedural Algorithm

To localize the epitopes responsible for inducing flavivirus cross-reactive antibodies, the following procedural algorithm was developed: Strictly-conserved flavivirus residues were initially identified. These residues were mapped onto the 2.0 Å resolution E-glycoprotein structure for TBE virus (Rey et al., *Nature* 375:291-98, 1995) and onto a computer predicted homology model structure for the DEN-2 virus E-glycoprotein using the Swiss-Pdb Viewer 3.7 structure analysis software (Guex et al., *Electrophoresis* 18:2714-23, 1997; available on the ExPASy Molecular Biology Server). A brief review of high resolution structures for antigen-antibody complexes revealed that 10-20 residues typically are involved in making direct contacts between the antigen epitope and antibody paratope. These contacts result in 20-30 residues that are "buried" by the typical antibody footprint, measuring approximately 20×30 Å. On average however, only 25% of the buried side chains, or 4-6 residues, account for most of the mAb binding energy (Arevalo et al., *Nature* 356:859-63, 1993; Bhat et al., *PNAS* 91:1089-93, 1994; Davies & Cohen, *PNAS* 93:7-12, 1996; Faebler et al., *J. Mol. Biol.* 313:83-97, 2001; Fleury et al., *Nature St. Biol.* 6:530-34, 1999; Li et al., *Biochemistry* 39:6296-6309, 2000; Lo et al., *J. Mol. Biol.* 285:2177-98, 1999; and Mylvaganam et al., *J. Mol. Biol.* 281:301-22, 1998).

The following criteria were developed to select probable flavivirus group cross-reactive epitope residues: 1) an amino acid located in DII (for example, amino acids 52-135 and 195-285 in the TBE virus E-glycoprotein (Rey et al., *Nature* 375:291-98, 1995); 52-132 and 193-280 in the DEN-2 virus E-glycoprotein (Modis et al., *PNAS* 100:6986-91, 2003)) and conserved among more than one flavivirus; 2) amino acids on the outer or lateral surface of the E-glycoprotein dimer; 3) amino acids with at least 35% surface accessibility potential; 4) side chain projections accessible to antibody paratopes; and 5) residues with high temperature ($\beta$-) factors should be favored, as these residues tend to be flexible and are able to conform to the antibody paratope, increasing the antibody-antigen affinity.

Using this structure-based design approach, candidate flavivirus cross-reactive epitope residues were narrowed down from a total of 53 conserved amino acids in DII (38 invariant and 15 almost completely conserved), to less than ten probable DII cross-reactive epitope residues. Amino acid substitutions at these probable cross-reactive epitope residues were computer modeled, selecting substitutions that should reduce or ablate antibody recognition without altering E-glycoprotein structural conformation, disrupting dimer interactions, or impairing particle formation, maturation, or secretion. For this reason, cysteine residues otherwise satisfying the cross-reactive epitope criteria were not considered for mutagenesis because of their involvement in disulphide bridging necessary for proper E-glycoprotein structure and function (Modis et al., *PNAS* 100:6986-91, 2003; Rey et al., *Nature* 375:291-98, 1995).

Stability calculations were performed for all possible amino acid substitutions of candidate residues using the FOLD-X server (Guerois et al., *J. Mol. Biol.* 320:369-87, 2002; available on the internet) and the TBE virus E-glycoprotein pdb file coordinates (Rey et al., *Nature* 375:291-98, 1995). Amino acid substitutions modeled in the TBE virus E-glycoprotein with free energies of folding equal to or less than that of the non-mutated wild-type E-glycoprotein were re-examined with the Swiss-PdbViewer software to identify those substitutions that minimized local structural disturbances while maintaining structurally relevant biochemical interactions such as hydrogen bonding and/or charge interactions with neighboring amino acids. Because the outer surface of mature flavivirus particles are covered in a dense network of E and prM/M proteins, any conformational changes in the E-glycoprotein are likely to induce concerted reorganization across the surface of the virion (Kuhn et al., *Cell* 108:717-25, 2002; Modis et al., *PNAS* 100:6986-91, 2003). A comparison of the a priori stability calculations based on the TBE virus E-glycoprotein structure with a posteriori stability calculations from the DEN-2 virus atomic structure are shown in Table 2.

Site-Directed Mutagenesis

Site-specific mutations were introduced into the DEN-2 virus E gene using the Stratagene Quick Change® multi site-directed mutagenesis kit (Stratagene, La Jolla, Calif.) and pCB8D2-2J-2-9-1 as DNA template following the manufacturer's recommended protocols. The sequences of the mutagenic primers used for all constructs are listed in Table 1. Four or five colonies from each mutagenic PCR transformation were selected and grown in 5 ml LB broth cultures, mini-prepped and sequenced. Structural gene regions and regulatory elements of all purified plasmids were sequenced entirely upon identification of the correct mutation. Automated DNA sequencing was performed using a Beckman Coulter CEQ™ 8000 genetic analysis system (Beckman Coulter, Fullerton, Calif.) and analyzed using Beckman Coulter CEQ™ 8000 (Beckman Coulter, Fullerton, Calif.) and Lasergene® software (DNASTAR, Madison, Wis.).

Transient Expression of DEN-2 Virus Recombinant Antigens in COS-1 or CHO Cells

COS-1 and CHO cells were electroporated with pCB8D2-2J-2-9-1 using the protocol described by Chang et al. (*J. Virol.* 74:4244-52, 2000). Electroporated cells were recovered in 50 ml DMEM, seeded into 150 cm² culture flasks for VLP expression and into 96 well tissue culture plates (Costar® #3603; Corning, Inc., Corning, N.Y.) for IFA, and incubated at 37° C. with 5% $CO_2$. Six to eight hours following electroporation, the growth medium in the 150 cm² culture flasks was replaced with DMEM containing 2% FBS. Cells in 96 well plates for IFA were fixed 14-18 hours post electroporation. Tissue-culture medium and cells were harvested 48 and 96 hours post electroporation for antigen characterization.

Characterization of Mutant pCB8D2-J2-2-9-1 Infected Cells and Secreted Antigen

Fourteen to eighteen hours following electroporation, 96 well tissue culture plates containing cells transformed with the mutated pCB8D2-2J-2-9-1 clones were washed twice with phosphate buffered saline (PBS), fixed with 3:1 acetone:PBS for 10 minutes and air dried. E-glycoprotein-specific mAbs specific for each of the three E-glycoprotein domains were used to determine affinity reductions in DII cross-reactive epitopes by indirect IFA as described by Chang et al. (*J. Virol.* 74:4244-52, 2000).

Tissue culture medium was harvested 48 hours and 96 hours following electroporation. Cell debris was removed from tissue culture media by centrifugation for 30 minutes at 10,000 rpm. Ag-ELISA was used to detect secreted antigen from the mutagenized pCB8D2-2J-2-9-1 transformed COS-1 cells. Secreted antigen was captured with polyclonal rabbit anti-DEN-2 sera (Roehrig et al., *Virology* 246:317-28, 1998) at a 1:10,000 dilution. Murine hyper-immune ascetic fluid (MHIAF) specific for DEN-2 virus was used at a 1:3000 dilution to detect captured antigen, and this MHIAF was detected using horseradish peroxidase conjugated goat anti-mouse HIAF at a 1:5000 dilution. Secreted antigen from tissue culture medium was concentrated by centrifugation overnight at 19,000 rpm, and resuspended in THE buffer (50 mM Tris, 100 mM NaCl, 10 mM EDTA, pH 7.5) to $\frac{1}{200}^{th}$ the original volume. Concentrated antigen was analyzed with a panel of anti-DEN-2 mAbs in Ag-ELISA to determine mAb end point reactivities of the mutated antigens following the protocol of Roehrig et al. (*Virology* 246:317-28, 1998).

Affinity Reductions in DII Cross-Reactive Epitopes

Three anti-DEN-2 mAbs, 4G2, 6B6C-1 and 1B7-5, were used to determine affinity reductions in DII cross-reactive epitopes. These three mAbs share several characteristics: they recognize surface accessible epitopes in DII, they are flavivirus group- or subgroup-reactive, they are reduction-denaturation sensitive, they block virus-mediated cell-membrane fusion, they neutralize virus infectivity, and tryptic fragment mapping indicates that the binding domains of these three mAbs are formed by two discontinuous DEN-2 virus E-glycoprotein peptide fragments, aa1-120 and 158-400 (Aaskov et al., *Arch Virol.* 105:209-21, 1989; Henchal et al., *Am. J. Trop. Med. Hyg.* 34:162-69, 1985; Megret et al., *Virology* 187:480-91, 1992; Roehrig et al., *Virology* 246:317-28, 1998). Prospective cross-reactive epitope residues were assessed by looking for decreases in the reactivity of these three DII flavivirus cross-reactive mAbs for the mutant plasmid transfected cells by IFA, and mutant VLPs in Ag-ELISA. Proper E-glycoprotein folding and structural conformation was assessed with a panel of E-glycoprotein DEN virus complex-, subcomplex-, and type-specific mAbs.

Four potential flavivirus cross-reactive epitope residues were initially focused on. Single amino acid substitutions were introduced into the DEN-2 prM/E expression plasmid at the following positions (of SEQ ID NO: 14): $Gly_{106}$ to Glu ($G_{106}Q$), $Trp_{231}$ to Phe ($W_{231}F$), $His_{244}$ to Arg ($H_{244}R$), and $Lys_{247}$ to Arg ($K_{247}R$) (Table 1). Substitutions at $Gly_{106}$ and $Trp_{231}$ strongly interfered with the binding of flavivirus cross-reactive mAbs (Table 3). However, substitutions at $His_{244}$ and $Lys_{247}$ did not have a measurable effect on the binding of the cross reactive mAbs or of any other mAbs from the panel.

Figure 2A:
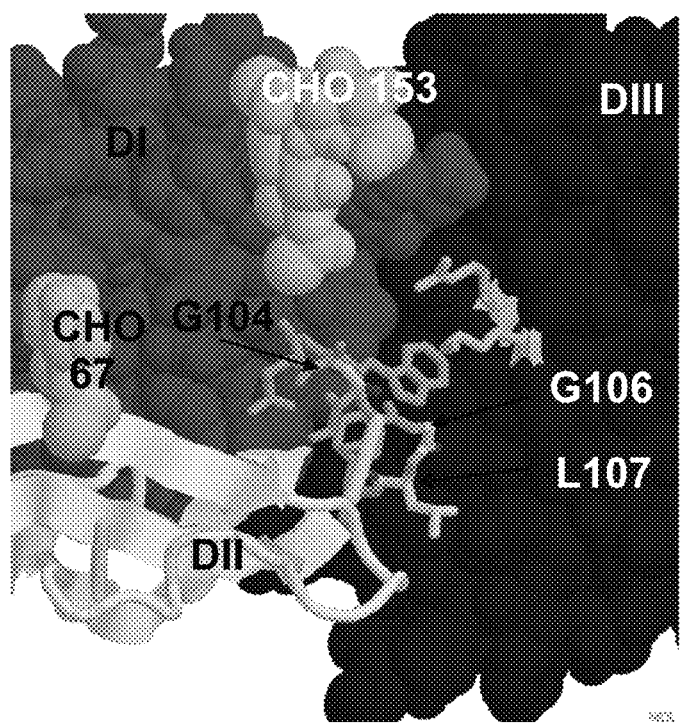

$Gly_{106}$ is located within the fusion peptide at the very tip of DII in the E-glycoprotein monomer (Allison et al., *J. Virol.* 73:5605-12, 1999; FIGS. 1 and 2A). As with the other fusion peptide residues, $Gly_{106}$ is strongly conserved across the flaviviruses, the one exception being Modoc virus with alanine at this position (Table 4). $Gly_{106}$ is located at the distal end of each E-monomer along the upper and outer-lateral surface of the dimer. This residue has moderately high surface accessibility, and its relatively high temperature ($\beta$-) factor suggests its potential flexibility. The substitution of a large, bulky, polar glutamine for the glycine at this position was modeled. The glutamine substitution fit well into the surrounding region, did not appear to disrupt the local hydrogen bonding network, and produced acceptable stability calculations using the TBE virus E-glycoprotein structure coordinates (Table 2).

Figure 2B:
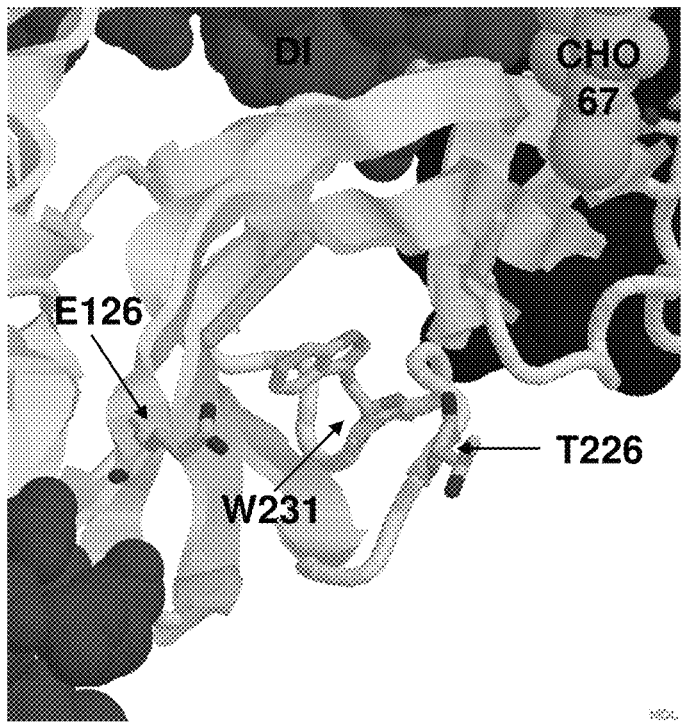

$Trp_{231}$ is located in a long intervening loop sequence between DII $\beta$-strands h and i (Modis et al., *PNAS* 100:6986-91, 2003; FIG. 1). $Trp_{231}$ lays in a trough on the upper and outer surface of DII (FIG. 2B). It is structurally close to the glycan on $Asn_{67}$, and lies laterally exterior to the disulfide bridge between $Cys_{60}$ and $Cys_{121}$. The large hydrophobic side chain lays parallel to the dimer surface within this trough. This residue is only moderately surface accessible yet its high temperature ($\beta$-) factor and the lack of hydrogen bonding from surrounding residues to the side chain suggest its potential flexibility. Although all of the substitutions that were modeled at $Trp_{231}$ were predicted to induce substantially high energetic costs from the stability analyses, the phenylalanine substitution was the least costly substitution at this position (Table 2). The phenylalanine fit well into the surrounding molecular region with limited disruption of the local hydrogen bonding network.

Binding of the $G_{106}Q$ mutant to either of the two flavivirus group-reactive mAbs, 4G2 and 6B6C-1, was not detected (Table 3). DEN-2 type-specific mAbs 1A5D-1 and 1B4C-2 (DII and DI, respectively) exhibited reduced affinities for $G_{106}Q$ transfected cells and for secreted VLPs. Dengue complex-specific mAb 10A1D-2 also exhibited moderately reduced reactivity for the $G_{106}Q$ VLP antigen (Table 3). However, the reactivity of the $G_{106}Q$ mutant was unchanged from the reactivity of the wild-type pCB8D2-2J-2-9-1 antigen for polyclonal anti-DEN-2 MHIAF, as well as for the remaining subcomplex- and type-specific mAbs: 9A4D-1 (DI), 4E5 (DII), and 3H5, 9A3D-8, 10A4D-2, 9D12, and 1 A1D-2 (DIII) (Table 3).

The $W_{231}F$ substitution also abolished the binding of both flavivirus group-reactive mAbs, 4G2 and 6B6C-1, as well as that of flavivirus subgroup-reactive mAb 1B7-5 (Table 3). This substitution additionally interfered with the binding of type-specific DI mAb 1B4C-2, but the binding of the remaining subcomplex- and type-specific DI, DII and DIII mAbs and a polyclonal DEN-2 MHIAF were unchanged relative to the non-mutated wild-type plasmid (Table 3). In three separate experiments, secretion of $W_{231}F$ VLP antigen into the tissue culture medium from transiently transfected COS-1 cells was not detected. Consequently, the effects of this substitution could only be analyzed by IFA of plasmid transfected cells.

The $H_{244}12$ and $K_{247}R$ substitutions did not have an effect on the binding of any mAbs in either IFA of transfected cells, or in Ag-ELISA of secreted VLP antigen.

EXAMPLE 2

Identification of Additional Cross-Reactive Epitopes Through Nearest Neighbor Search This example demonstrates the identification of additional cross-reactive epitopes using a "nearest neighbor" search.

Following the identification of cross-reactive epitope residues G106 and $W_{231}$ (DEN-2 numbering), the E-glycoprotein atomic structure was reexamined to search for additional flavivirus cross-reactive epitope residues. A "nearest neighbor" search was conducted of the surface of the E-glycoprotein structure, looking for additional residues located within 10-15 Å of the identified residue. This distance is within the binding footprint of a single antibody paratope (Faebler et al., *J. Mol. Biol.* 313:83-97, 2001). In this second iteration of cross-reactive epitope residue identification the same five optimality criterion as above were used, with one change. The criterion of strict conservation across the flaviviruses was relaxed to now include variable residues. In this way, residues either conserved in their physiochemical nature and/or conserved only within a particular flavivirus complex (such as the four DEN virus serotypes) could be identified.

This nearest neighbor search yielded another seven potential cross-reactive epitope residues. Amino acid substitutions at these positions were modeled into the TBE virus E-glycoprotein structure as described above. Mutagenic PCR primers were then synthesized (Table 1) and used to introduce mutations into the wild-type DEN-2 prM/E expression plasmid. Plasmids were transiently transfected into CHO cells, and transfected cells and secreted VLP antigen were analyzed with the anti-DEN-2 mAb panel (Table 3). The substitutions introduced at these positions (of SEQ ID NO: 14) were: $Lys_{64}$ to Asn ($K_{64}N$), $Thr_{76}$ to Met ($T_{76}M$), $Gln_{77}$ to Arg ($Q_{77}R$), $Gly_{104}$ to His ($G_{104}H$), $Leu_{107}$ to Lys ($L_{107}K$), $Glu_{126}$ to Ala ($E_{126}A$), and $Thr_{226}$ to Asn ($T_{226}N$) (Table 2). A single double mutant combining substitutions at positions 126 and 226 ($E_{126}A/T_{226}N$) was also examined. Since the initial $W_{231}F$ substitution interfered with antigen secretion, the effects of an alternative substitution at this position, $Trp_{231}$ to Leu ($W_{231}L$), were also examined.

The $G_{104}H$, $L_{107}K$, and $W_{231}L$ substitutions had the greatest effect on decreasing the reactivities of DII cross-reactive mAbs. $Gly_{104}$ is located on the upper surface of the dimer at the tip of the tight loop structure which the fusion peptide adopts in the E-glycoprotein dimer (Modis et al., *PNAS* 100: 6986-91, 2003; FIG. 2A). The residue has moderately high surface accessibility and a relatively high temperature (β-) factor. The replacement of this small aliphatic glycine was modeled with a large polar histidine at this position. The histidine residue fits well into this pocket and was predicted not to alter the hydrogen-bond network in the region. Moreover, because the tick-borne flaviviruses have a histidine at this position (Table 4) it seemed probable that this substitution would not disrupt the structure in this localized region or elsewhere within DII. In fact, a posteriori stability calculations based upon the DEN-2 E atomic structure (Modis et al., *PNAS* 100:6986-91, 2003) indicate that the $G_{104}H$ substitution is energetically favorable (Table 2).

The $G_{104}H$ substitution, like both substitutions examined at $Trp_{231}$, produced a plasmid that was unable to secrete measurable VLP antigen into the tissue culture medium upon transfection of either COS-1 or CHO cells. Consequently, the effects of $G_{104}H$ and $W_{231}L$ substitutions were analyzed solely by IFA of plasmid transfected cells, as described above for $W_{231}F$. The $G_{104}H$ substitution ablated the reactivity of all three of the flavivirus cross-reactive mAbs, 402, 6B6C-1, and 1B7-5. The type-specific DII mAb 1A5D-1 also showed strongly reduced reactivity for cells transiently transcribed with this plasmid Table 3). $W_{231}L$ showed a reduction in mAb reactivities very similar to $W_{231}F$, knocking out any discernable recognition of all three cross-reactive mAbs (Table 3). The reactivity of DI mAb 1B4C-2 was also reduced by this mutation, but there were no discernable changes in the reactivities of the remaining subcomplex- and type-specific mAbs or the anti-DEN-2 MHIAF for either the $G_{104}H$ or $W_{231}L$ plasmid constructs (Table 3).

The $L_{107}K$ substituted plasmid exhibited a pattern of reduced reactivities for flavivirus cross-reactive mAbs unlike any of the other substitutions. $Leu_{107}$ sits directly below $Gly_{106}$ on the outer lateral surface of the E-protein dimer. This residue has relatively high surface accessibility and temperature (β-) factor, and its hydrophobic side-chain is directed laterally away from the dimer. This residue is also strongly conserved across the flaviviruses; the exceptions being the tick-borne Powassan virus, JE virus strain SA-14-14-2, and DEN-2 virus strain PUO-280 (Table 4). All of these viruses have a phenylalanine instead of a leucine at this position. A large basic lysine was substituted for the leucine at this position. Modeling of this $L_{107}K$ substitution indicated that it too was unlikely to alter the localized hydrogen bonding network. This observation and the low thermodynamic free energy (ddG) stability calculation (Table 2) suggested that this substitution was unlikely to induce localized or domain associated conformational changes.

Flavivirus group-reactive mAb 4G2 showed no discernable reactivity for this construct in either IFA of plasmid transfected cells, or by Ag-ELISA of secreted VLP antigen. However, the reactivities of the other two cross-reactive mAbs, 6B6C-1 and 1B7-5, were unchanged for this construct relative to the non-mutated wild-type plasmid (Table 3). $L_{107}K$ plasmid-transfected cells and secreted VLP antigen also showed moderately reduced reactivity for mAbs 1A5D-1, 10A1D-2 and 1B4C-2, while all other mAbs and the polyclonal MHIAF reactivities were not significantly different than they were for the wild-type plasmid (Table 3).

Unlike $Leu_{107}$, $Glu_{126}$ appears to be incorporated into epitopes recognized by flavivirus group-reactive mAb 6B6C-1 and subgroup-reactive mAb 1B7-5, but not in the epitope of flavivirus group-reactive mAb 4G2. $Glu_{126}$ is located 10-12A from $Trp_{231}$ in the same trough on the upper and outer surface of DII. The bulky side chain projects from the α-carbon backbone up into this trough producing a moderately high surface accessibility and a high β-factor (FIG. 2B). The replacement of this large, negatively charged acidic glutamine was modeled with a small hydrophobic alanine at this position. This substitution was predicted to induce a moderately high, but acceptable energetic cost in the free energy stability analysis based on the TBE virus E-glycoprotein structure coordinates (TBE virus equals $Lys_{126}$, Table 2).

The $E_{126}A$ substitution reduced the reactivity of flavivirus group-reactive mAb 6B6C-1, and moderately reduced the reactivity of subgroup-reactive mAb 1B7-5 (Table 3). However, mAb 6B6C-1 exhibited reduced reactivity only by IFA of mutant plasmid transfected cells, and 1B7-5 only showed reactivity reductions for this construct in Ag-ELISA (Table 3). Similarly, type-specific DII mAb 1A5D-1 exhibited moderately reduced reactivity by Ag-ELISA, but there was no detectable reduction in its reactivity by IFA (Table 3). The $T_{226}N$ substitution did not alter the reactivity of any of the flavivirus group-reactive mAbs relative to the non-mutated wild-type plasmid, and the $E_{126}A/T_{226}N$ double mutant generally showed a similar pattern of reduction of mAb reactivity as did $E_{126}A$ alone. The two exceptions to this correlation were in the reactivities of mAbs 1B7-5 and 10A1D-2. $E_{126}/T_{266}N$ exhibited the same moderate 87% reduction in Ag-ELISA reactivity for flavivirus subgroup-reactive mAb 1B7-5 as did $E_{126}A$. However, the double mutant also exhibited a strong 97% reduction for this same mAb by IFA, which was not observed for either single mutant (Table 3). DEN virus complex-specific mAb 10A1D-2 also exhibited moderate reactivity decreases by IFA for this double mutant (Table 3).

$K_{64}N$, $T_{76}M$, and $Q_{77}R$ were all unchanged in their reactivities for the flavivirus cross-reactive mAbs. The $T_{76}M$ VLP antigen did however show reduced reactivity for DII type-specific mAb 1A5D-1 and for DI mAb 1B4C-2 in Ag-ELISA (Table 3).

EXAMPLE 3

Spatial Characterization and Organization of Flavivirus Group-Reactive Epitope Residues This example describes the spatial characterization and organization of exemplary flavivirus cross-reactive epitope residues.

The six residues ($G_{104}$, $G_{106}$, $L_{107}$, $E_{126}$, $T_{226}$, and $W_{231}$) identified as participating in the flavivirus cross-reactive epitopes are spatially arranged on the DEN-2 virus E-glycoprotein surface in two clusters (FIG. 1). The most prominent grouping of these residues is the clustering of three residues from the highly conserved fusion peptide region of DII (Allison et al., *J. Virol.* 75:4268-75, 2001). These residues, $Gly_{104}$, $Gly_{106}$, and $Leu_{107}$, are almost completely conserved across the flaviviruses (Table 4).

The cross-reactive mAbs most strongly affected by substitutions in this region were 4G2 and 6B6C-1. These two mAbs are considered to be quite similar; both are flavivirus group-reactive and have been grouped into the A 1 epitope of the E-glycoprotein (Gentry et al., *Am. J. Trop. Med. Hyg.* 31:548-55, 1982; Henchal et al., *Am. J. Trop. Med. Hyg.* 34:162-69, 1985; Mandl et al., *J. Virol.* 63:564-71, 1989; Roehrig et al., *Virology* 246:317-28, 1998). The data disclosed herein demonstrate that although the epitopes of these two mAbs spatially overlap, they do not contain exactly the same residues. Substitutions at $G_{104}$, $G_{106}$, or $L_{107}$ knock out the ability of mAb 4G2 to bind to the E-glycoprotein. However, only substitutions at $G_{104}$ and $G_{106}$ interfere with the binding ability of mAb 6B6C-1. $L_{107}$ is therefore not a component of the flavivirus group-reactive epitope recognized by mAb 6B6C-1.

The $G_{104}H$ substitution dramatically reduced the reactivities of all three of the flavivirus cross-reactive mAbs for this construct (Table 3). Without being bound by theory, it is unlikely that a glycine residue, with no side chain, would directly participate in the binding energetics of an antibody-antigen (Ab-Ag) interaction. However, if a glycine residue is included in the buried surface area of this antibody epitope, the introduction of a large bulky hydrophobic side chain is likely to disrupt the Ab-Ag shape complementarity and hence increase the dissociation rate-constant ($k_d$) of the Ab-Ag interaction (Li et al., *Nature Struct. Biol.* 10:482-88, 2003). $G_{104}H$ also reduced the recognition of type-specific DII mAb 1A5D-1 (Table 3). The 1A5D-1 epitope is non-neutralizing, reduction sensitive and moderately surface accessible (Roehrig et al., *Virology* 246:317-28, 1998). All of the fusion peptide substitutions introduced into this region reduced the reactivity of 1A5D-1, consistent with the interpretation that the buried surface area footprint of this mAb not only includes DEN-2 virus serotype-specific residues, but also includes these strongly conserved residues as well. A comparison of the DEN-2 atomic structure with flavivirus E-glycoprotein alignments identifies at least two unique DEN-2, DII, surface accessible residues ($Glu_{71}$ and $Asn_{83}$), and a third residue variable within DEN-2 but distinct from the other DEN virus serotypes ($Thr_{81}$). All of these residues are within 10-22 Å of $Gly_{104}$, a distance well within the buried surface area of a typical Ab-Ag interface (Lo et al., *J. Mol. Biol.* 285:2177-98, 1999). Alternatively, less surface accessible type-specific residues nearby could participate in mAb 1A5D-1 binding since this epitope itself is only moderately surface accessible (Roehrig et al., *Virology* 246:317-28, 1998). Since this mAb is DEN-2 virus specific, these type-specific residues would be expected to provide the majority of the binding energy for 1A5D-1.

The $G_{106}Q$ substitution also knocked out the reactivities of both of the flavivirus group-reactive mAbs, 4G2 and 6B6C-1, though it did not alter the binding of subgroup-reactive mAb 1B7-5 (Table 3, FIG. 2C). Type-specific DII mAb 1A5D-1 again lost all measurable reactivity to the $G_{106}Q$ construct, as did 1B4C-2. The 1A5D-1 epitope footprint appears to include conserved fusion peptide residues in addition to DEN-2 serotype-specific residues as discussed herein. The reduced reactivity of DI mAb 1B4C-2 for the $G_{106}Q$ construct is difficult to explain. Because of the lack of biological activity of DI, epitope assignments to this domain can be problematic (Roehrig et al., *Virology* 246:317-28, 1998). Without being bound by theory, the involvement of $Gly_{106}$ as well as that of $Leu_{107}$ are consistent with the possibility that either the previous DI assignment is incorrect, or that the 1B4C-2 mAb footprint includes residues from both DI and DII. However, if 1B4C-2 recognizes such an inter-domain epitope, this high affinity mAb would be expected to interfere with the E-glycoprotein dimer to trimer reorganization associated with virus-mediated membrane fusion, which it does not.

$Leu_{107}$ is the third residue identified in the fusion peptide region of DII that is incorporated into flavivirus cross-reactive epitopes. Unlike the substitutions at E-glycoprotein positions 104 and 106, the $L_{107}K$ substitution knocked out the reactivity of flavivirus group-reactive mAb 4G2, but it did not alter the reactivity of the other flavivirus group-reactive mAb, 6B6C-1 (Table 3, FIG. 2C). Beyond this discrepancy, the reactivity patterns of the rest of the mAbs for this construct were similar to that observed for the other fusion peptide substitutions. mAbs 1A5D-1, 10A1D-2, and 1B4C-2 all showed little to no reactivity for the $L_{107}K$ construct (Table 3).

Previous studies have examined the effects of mutagenesis in this fusion peptide region. Pletnev et al. (*J. Virol.* 67:4956-63, 1993) performed mutagenesis to fusion peptide residues 104 and 107 in a chimeric infectious clone containing the TBE virus structural genes and DEN-4 virus non-structural genes. TBE virus has a histidine at position 104 as do all of the tick-borne flaviviruses. Pletnev et al. constructed the opposite substitution that was constructed herein, $H_{104}G$, replacing the tick-associated histidine with the mosquito-associated glycine, but they were unable to recover live virus from this construct. They also constructed a double mutant $H_{104}/L_{107}F$ from which they were able to recover virus; however, they were unable to detect any effect of these mutations on mouse neurovirulence. Allison et al. (*J. Virol.* 75:4268-75, 2001) also performed mutagenesis at $Leu_{107}$ examining the role of this residue in virus-mediated membrane fusion using TBE virus VLPs. They replaced $Leu_{107}$ with phenylalanine, threonine, or aspartic acid. They found that all of these mutations reduced the rate of fusion. Moreover, consistent with the results presented herein, they found that the $L_{107}D$ substitution appeared to completely abolish the binding of their DII flavivirus group-reactive mAb A1.

The fourth residue identified as having a major effect on the flavivirus cross-reactive mAbs was $Trp_{231}$, an invariant residue across the flaviviruses (Table 4). Both substitutions introduced at $Trp_{231}$ dramatically reduced the reactivity of all three of the flavivirus cross-reactive mAbs, 4G2, 6B6C-1, and 1B7-5. This residue is structurally distant from the fusion peptide region (FIGS. 1 and 2B). It is somewhat surprising that substitutions at this residue affect the binding of mAbs also shown to recognize the distant fusion peptide residues. Without being bound by theory, the strict conservation of tryptophan (Table 4) and the predicted high energetic costs of substitutions at this position (Table 2) suggest that this residue could be important for proper DI/DII conformational structure and function. If this were the case, the loss of reactivity of mAbs recognizing fusion peptide residues could occur from the induction of localized structural disturbances across DII occurring at a distance from $Trp_{231}$. However, the $Trp_{231}$ substitutions did not significantly affect the binding of any of the remaining DII mAbs, 4E5, 1A5D-1, and 10A1D-2 (DI or DII); whereas mAb 1A5D-1 reactivity was reduced or ablated by all of the fusion peptide substitutions. mAb 4E5 does not recognize native virus yet it blocks virus-mediated cell-membrane fusion, presumably by recognizing an epitope that is exposed only during or after low-pH-catalyzed conformational changes (Roehrig et al., *Virology* 246:317-28, 1998). Without being bound by theory, if substitutions at $Trp_{231}$ induced domain wide structural alterations, a loss of reactivity of mAb 1A5D-1 (and the possible exposure of the non-native-accessible mAb 4E5 epitope, resulting in an increase, or at least a change in, the reactivity of mAb 4E5 by IFA for these constructs), would be expected. Moreover, the reactivities of polyclonal MHIAF and of all of the DIII mAbs were no different for these constructs than they were for the non-mutated wild-type plasmid transfected cells (Table 3). DIII however, is reduction-denaturation stable and folds into its native IgC like conformation even when this domain is expressed alone without the remainder of the E-glycoprotein (Bhardwaj et al., *J. Virol.* 75:4002-07, 2001).

Both $W_{231}F$ and $W_{231}L$ plasmids, as well as the $G_{104}H$ plasmid, failed to secrete measurable VLP antigen into tissue culture media following transient transfection of COS-1 or CHO cells. The inability of cells transfected with these plasmids to secrete VLP antigen into tissue-culture media could result from the disruption of a variety of protein maturation processes. Without being bound by theory, interference with particle maturation could occur via disruption of E-prM/M intermolecular interactions, E-glycoprotein dimer interactions, or via the disruption of dimer organization into the surface lattice covering mature particles. Although the two processes are interdependent, these substitutions may not interfere with particle formation per se, but may directly interfere with particle secretion itself. In fact, the IFA staining pattern of DEN-2 $G_{104}H$ and of $W_{231}F/L$ transfected cells was highly punctate and localized within inclusion bodies. Similar IFA staining patterns have been observed with non-secreting constructs of dengue and other flaviviruses (Chang et al., *Virology* 306:170-80, 2003). Studies with TBE virus VLPs have shown that interactions between prM and E are involved in prM-mediated intracellular transport of prM-E heterodimers (Allison et al., *J. Virol.* 73:5605-12, 1999). The location of $Gly_{104}$ near the interior-lateral edge of DII puts it very close to the E-dimer "hole" where the prM/M proteins are located in the heterodimer (Kuhn et al., *Cell* 108:717-25, 2002; FIG. 1). Therefore, it seems likely that $G_{104}H$ interferes with VLP secretion via disruption of the prM-E interactions necessary for intracellular transport and secretion. The identity of this residue is positively correlated with arthropod vector. The mosquito-born flaviviruses have a glycine at this position whereas the tick-borne flaviviruses have a histidine. Interestingly, Pletnev et al. (*J. Virol.* 67:4956-63, 1993) introduced the reverse substitution, $H_{104}G$, into the TBE virus E-glycoprotein in a TBE/DEN-4 chimeric infectious clone, and they were unable to recover virus from this mutant. The inability of $G_{104}H$ transfected cells to secrete VLP antigen similarly suggests that this too could be a lethal substitution in DEN-2 virus. Taken together, these two results are consistent with the idea that vector-specific selection has produced strong epistasis between this residue and other unidentified residue(s) elsewhere in the E- or prM/M proteins.

EXAMPLE 4

Identification of Flavivirus Complex and Sub-Complex Cross-Reactive Epitope Residues This example demonstrates the identification of flavivirus complex and sub-complex cross-reactive epitopes using a structure-based rational mutagenesis method.

Cell Culture, Virus Strains and Recombinant Plasmids

CHO cells (ATCC CCL 61; Manassas, Va.) were grown at 37° C. with 5% $CO_2$ on Dulbeco's modified Eagle's minimal essential medium with F-12 nutrient mixture (D-MEM/F-12, GIBCO, Grand Island, N.Y.) supplemented with 10% heat-inactivated fetal bovine serum (FBS, Hyclone Laboratories, Inc., Logan, Utah), 110 mg/l sodium pyruvate, 0.1 mM non-essential amino acids, 2 mM L-glutamine, 2.438 g/L $NaHCO_3$, 100 U/ml penicillin, and 100 μg/ml streptomycin.

The recombinant expression plasmids pCB8SJ2 and pCBWN were used as template DNAs for both site-directed mutagenesis and for transient expression of St. Louis encephalitis virus (SLEV) and West Nile virus (WNV) recombinant antigen (see below). The pCB8SJ2 plasmid includes the human cytomegalovirus early gene promoter, Japanese encephalitis virus (JEV) signal sequence, SLEV prM and E gene region (amino-terminal 80%), JEV carboxyl terminal 20%, and bovine growth hormone poly(A) signal. The replacement of the terminal 20% of SLEV E with JEV E gene sequences dramatically increases the secretion of extracellular VLPs into the culture medium without altering the native SLEV E glycoprotein conformation (Purdy et al., *J. Clin. Micro.* 42:4709-17, 2004). The pCBWN plasmid includes the human cytomegalovirus early gene promoter, JEV signal sequence, WNV prM and E gene region in its entirety, and bovine growth hormone poly(A) signal (Davis et al., *J. Virol.* 75:4040-47, 2001).

Procedural Algorithm

Following the identification and ablation of flavivirus group cross-reactive epitopes, flavivirus complex and sub-complex cross-reactive epitopes have been identified. Two different flavivirus complexes, the JEV complex and the DENV complex, were focused on. The DENV complex consists of the four dengue serotypes, DENV-1, DENV-2, DENV-3, and DENV-4. The large JEV complex includes JEV, WNV, Murray Valley encephalitis virus (MVEV), and SLEV.

The procedural algorithm for the identification of flavivirus complex and sub-complex cross-reactive epitopes utilizes the following optimality criteria: 1) The identification and selection of amino acid residues with ≥35% of their surface solvent accessible. These residues are identified from the published atomic structure coordinates of the DENV-2 soluble ectodomain of the envelope glycoprotein and homology models of SLEV and WNV derived from the DENV-2 structure (Modis et al., *Proc. Natl. Acad. Sci. USA* 100:6986-91, 2003). In addition to examination of amino acid residues in structural domain II, residues in domains I and III were examined, since published results indicate that some complex and sub-complex cross-reactive epitopes are mapped onto domains I and III in addition to domain II (Roehrig et al., *Virology* 246:317-28, 1998). 2) Amino acids on the outer or lateral surface of the E-glycoprotein dimer, and accessible to antibody. 3) Amino acid conservation across the flavivirus complex (based upon a structural alignment of the protein sequences). Residues conserved across all member viruses of the same complex are favored. If conserved within but not across the entire complex, then residues with shared identities between WNV and SLEV are favored in the JEV complex, and residues with shared identities between DENV-2 and two or more other viruses in the DENV complex are favored over those shared with DENV-2 and only one other DENV complex virus. 4) Side chain projections exposed towards the outer surface and accessible to antibody paratopes. 5) Residues with high temperature (β-) factors should be favored, as these residues tend to be flexible and are able to conform to the antibody paratope, increasing the antibody-antigen affinity. Amino acid residues with high temperature factors are more commonly found in antigen epitopes than lower temperature factor residues. 6) Following identification of potential individual flavivirus complex and sub-complex cross-reactive epitope residues, all residues are mapped and highlighted on the same E-glycoprotein dimer structure together. With this technique, groups of potential cross-reactive epitope residues forming clusters (and hence probable epitopes) are readily identified. 7) Residues fitting all of these criteria and occurring in structural clusters approximately 20×30 $Å^2$ (which is the average "footprint" of an antibody Fab that interacts with an antigen epitope) are favored over residues that are more isolated in the protein structure. 8) Within an identified structural cluster of potential epitope residues, residues that more completely satisfy greater numbers of the optimality criteria are selected for the first round of mutagenesis analysis.

Site-Directed Mutagenesis

Site-specific mutations were introduced into the SLEV and WNV E genes using the Stratagene Quick Change® multi site-directed mutagenesis kit (Stratagene, La Jolla, Calif.) and pCB8SJ2 and pCBWN as DNA templates following the manufacturer's recommended protocols. The sequences of the mutagenic primers used for all constructs are listed in Table 5. Four or five colonies from each mutagenic PCR transformation were selected and grown in 5 ml LB broth cultures. DNA was mini-prepped and sequenced from these cultures. Structural gene regions and regulatory elements of all purified plasmids were sequenced entirely upon identification of the correct mutation. Automated DNA sequencing was performed using a Beckman Coulter CEQ™ 8000 genetic analysis system (Beckman Coulter, Fullerton, Calif.) and analyzed using Beckman Coulter CEQ™ 8000 (Beckman Coulter, Fullerton, Calif.) and Lasergene® software (DNASTAR, Madison, Wis.).

Transient Expression of SLEV and WNV Recombinant Antigens by CHO Cells

CHO cells were electroporated with pCB8SJ2 or pCBWN using the protocol described by Chang et al. (*J. Virol.* 74:4244-52, 2000). Electroporated cells were recovered in 50 ml DMEM, seeded into 150 cm² culture flasks for VLP expression and into 96-well tissue culture plates for IFA, and incubated at 37° C. with 5% $CO_2$. Cells in 96 well plates for IFA were fixed 14-24 hours post electroporation. Tissue-culture medium and cells were harvested 48-72 hours post electroporation for antigen characterization.

Characterization of Mutant pCB8SJ2 and pCBWN Infected Cells and Secreted Antigen Fourteen to twenty four hours following electroporation, 96-well tissue culture plates (Costar® #3603 Corning, Inc., Corning, N.Y.) containing cells transformed with the mutated pCB8SJ2 or pCBWN clones were washed twice with PBS, fixed with 3:1 acetone:PBS (v:v) for 10 minutes and air dried. E-glycoprotein-specific mAbs recognizing each of the three E-glycoprotein domains (Table 6) were used to determine affinity reductions in cross-reactive epitopes by IFA as described by Chang et al. (*J. Virol.* 74:4244-52, 2000).

Tissue culture medium was harvested 48-72 hours following electroporation. Cell debris was removed from tissue culture media by centrifugation for 30 minutes at 10,000 rpm. Ag-ELISA was used to detect secreted antigen from the mutagenized pCB8SJ2 and pCBWN transformed CHO cells. Secreted antigen was captured with polyclonal rabbit anti-SLEV and rabbit anti-pCBWN sera at 1:30,000 and 1:50,000 dilutions, respectively. MHIAF specific for SLEV and WNV was used at a 1:15,000 dilution to detect captured antigen, and this MHIAF was detected using horseradish peroxidase conjugated goat anti-mouse HIAF at a 1:5000 dilution.

Secreted antigen was concentrated from positive tissue culture medium by centrifugation overnight at 19,000 rpm, and resuspended in TN buffer (50 mM Tris, 100 mM NaCl, pH 7.5) to $\frac{1}{100}^{th}$ the original volume. Alternatively, some antigens were concentrated using Millipore's Amicon® Ultra PL-100 (Millipore, Billerica, Mass.) centrifugal filter devices. Concentrated antigen was analyzed with a panel of anti-flavivirus mAbs in Ag-ELISA to determine mAb end point reactivities of the mutated antigens, following the protocol of Roehrig et al. (*Virology* 246:317-28, 1998). This Ag-ELISA protocol is the same as that used herein to detect secreted antigen, with the exception of using the specified mAbs (Table 6) instead of polyclonal MHIAF.

Antigenic Characterization and MAb Screening of Potential Cross-Reactive Epitope Residue Mutants Using the structure-based design approach described above, candidate flavivirus complex and sub-complex cross-reactive epitope residues were narrowed down to 34 in DENV-2 and 31 each in WNV and SLEV. From these residues and with reiterative application of the optimality criteria described herein 17 DENV-2, 13 WNV, and 11 SLEV residues were chosen as most likely to be incorporated into complex and sub-complex cross-reactive epitopes (highlighted in Tables 7-9). Amino acid substitutions were modeled at these probable cross-reactive epitope residues, selecting substitutions that should potentially disrupt or ablate antibody recognition without altering E-glycoprotein structural conformation, disrupting dimer interactions, or impairing particle formation, maturation, or secretion. Stability calculations were performed for all possible amino acid substitutions of candidate residues using the PoPMuSiC server, (available on the Universite Libre de Bruxelles' web site) and the DENV-2 E-glycoprotein pdb file coordinates (Modis et al., *Proc. Natl. Acad. Sci.* 100:6986-91, 2003) or homology model coordinates for WNV and SLEV. Amino acid substitutions modeled in the E-glycoprotein structures with free energies of folding equal to or less than that of the non-mutated wild-type E-glycoprotein were re-examined with the Swiss-Pdb Viewer software (available on the Swiss Institute of Bioinformatics' web site) to identify those substitutions that minimized local structural disturbances while maintaining structurally relevant biochemical interactions such as hydrogen bonding and/or charge interactions with neighboring amino acids.

Substitutions at 11 of 16 potential cross-reactive epitope residues selected for mutagenesis in pCB8SJ2 altered the reactivities of all 14 of the anti-SLE mAbs, relative to wild-type pCB8SJ2 (Table 10). Eight of the 14 MAbs were flavivirus group- or subgroup-cross-reactive (see Table 6). Substitutions at nine of the 16 residues analyzed altered the reactivity of all eight of the flavivirus group- or subgroup-cross-reactive mAbs. Substitutions at four of 16 potential cross-reactive epitope residues altered all three of the JEV complex- and subcomplex-cross reactive mAbs. Only one substitution however, affected type-specific mAb reactivities (FIG. 3). The effect of this substitution ($G_{106}Q$) on type-specific mAb reactivities was to actually increase the reactivity of these mAbs relative to that of the wild-type unaltered pCB8SJ2. Without being bound by a single theory, such increase in the reactivity of type-specific antibodies is believed to be beneficial for the development of type-specific flavivirus antigens.

Substitutions at 14 of 17 residues selected for mutagenesis in pCBWN altered the reactivities of all 10 of the anti-WNV mAbs, relative to wild-type pCBWN (Table 11). Six of the 10 anti-WNV mAbs were flavivirus group- or subgroup-cross-reactive, two were JEV complex cross-reactive and two were WNV type-specific (see Table 6). Nine of the 17 substitutions examined altered the reactivities of all six group- and sub-group-cross-reactive mAbs; 12 of these 17 substitutions affected the reactivities of both of the JEV complex cross-reactive mAbs. The $G_{106}V$ substitution in pCBWN was the only substitution to alter type-specific mAb reactivities, and, as with pCB8SJ2, this substitution actually increased the reactivity of the type-specific mAbs (FIG. 3).

The outcome that many of these substitutions altered mAb reactivities (Tables 10 and 11; FIG. 3) illustrates not only the efficiency of the described algorithms for identifying cross-reactive epitope residues, but also that these cross-reactive epitopes can be altered to ablate or appreciably interfere with the ability of an antibody to recognize these modified antigens. For example, 82% and 69% of the potential cross-reactive epitope residue substitutions examined in pCBWN and pCB8SJ2, respectively, affected all of the cross-reactive antibodies reactive to these two viruses from the antibody panel (see FIG. 3). The high percentage of residues, selected a priori, affecting mAb reactivities illustrates the accuracy of the cross-reactive epitope residue selection algorithms.

The mAb characterization of potential cross-reactive epitope residue mutants illustrates the importance of the E-protein fusion peptide region as a potently cross-reactive antigenic determinant. As described herein, substitutions at fusion peptide residues $G_{104}$, $G_{106}$, and $L_{107}$ strongly affected many of the mAb reactivities for DENV-2, SLEV and WNV (see Tables 10 and 11). Without being bound by a single theory, $G_{106}$ appears to be the most important cross-reactive antigenic determinant of these residues. Substitutions at $G_{106}$ altered the reactivities of 7 of 10 cross-reactive mAbs recognizing SLEV, and 7 of 8 cross-reactive mAbs recognizing WNV (see Tables 10 and 11). Substitutions at fusion peptide residue G104 also affected the reactivities of many mAbs for each of these viruses. However, all substitutions examined at this position produced plasmids that were unable to efficiently secrete VLP antigen upon transient transformation into eukaryotic cells. This observation was true for all three flaviviruses examined: DENV-2, SLEV and WNV.

Substitutions at fusion peptide residue $G_{106}$ had a variety of effects on mAb reactivities for both pCBWN and pCB8SJ2. The majority of the substitutions at this residue reduced or ablated a mAb's ability to recognize the antigen. This occurred with cross-reactive mAbs 4G2, 6B6C-1, 4A1B-9, and 2B5B-3 in $G_{106}$V-pCBWN and with 4G2 and 2B5B-3 for $G_{106}$Q-pCB8SJ2 (see Tables 10 and 11), indicating that the substituted residue is a part of the antigenic epitope recognized by these antibodies.

EXAMPLE 5

Human IgM MAC-ELISA Serology

This example demonstrates the representative nature of a murine antibody response as a model of human antibody response to substitutions in the flavivirus cross-reactive epitopes.
Human Sera Well-characterized serum specimens were assembled from the Diagnostic and Reference Laboratory, Arbovirus Diseases Branch, Division of Vector-Borne Infectious Diseases, US Centers for Disease Control and Prevention. A serum panel (see Table 12) was assembled from patients infected in the US between 1999 and 2004 with either WNV (n=6) or SLEV (n=10), as determined by the standard 90% plaque-reduction neutralization (PRNT) assay. SLEV is endemic to North America, whereas WNV was first introduced into North America in 1999 and has spread epidemically since that time.

The flavivirus responsible for the most recent infection was determined as that with the highest neutralizing antibody titer, which had to be at least four-fold greater than that for any other virus tested. Because of the high level of cross-reactivity between the SLEV and WNV viruses, it is often difficult to determine the infecting virus by ELISA, thus requiring the PRNT. SLEV infected sera with measurably high levels of cross-reactivity for WNV were purposefully selected in order to maximize the ability to asses for improved discrepancy (specificity) of the pCBWN-$G_{106}$V versus the pCBWN wild-type antigen. SLEV infected patient sera were split into two groups based upon previously determined (Diagnostic and Reference Laboratory) positive to negative (P/N) ratios for SLEV and for WNV. 'Equivocal' SLEV sera (n=5) were those that were clear SLEV infections from the PRNT data, yet had MAC-ELISA P/N ratios that were not statistically different between SLEV and WNV. Three of these equivocal SLEV samples were negative (P/N≤2.0) for both viruses, one was presumptive positive (P/N≥2.0 and <3.0), and one was definitive positive (P/N≥5.0) for both viruses. 'Misleading' SLEV sera (n=5) were SLEV positive in the PRNT, yet had MAC-ELISA P/N ratios that were not only positive for both viruses, but were actually greater for WNV than for SLEV. Definitive 'positive' WNV infected patient sera (n=6) were selected based on MAC-ELISA results from the Diagnostic and Reference Laboratory collection for use as positive control sera to assess the accuracy of the pCBWN-$G_{106}$V plasmid derived antigen.
IgM ELISA Protocols IgM ELISAs were performed following the protocols of Purdy et al. (*J. Clin. Micro.* 42:4709-17, 2004) and Holmes et al. (*J. Clin. Micro.* 43:3227-36, 2005). Briefly, the inner 60 wells of Immulon II HB flat-bottomed 96-well plates (Dynatech Industries Inc., Chantilly, Va.) were coated overnight at 4° C. in a humidified chamber with 75 µl of goat anti-human IgM (Kierkegaard &

Perry Laboratories, Gaithersburg, Md.) diluted at 1:2000 in coating buffer (0.015 M sodium carbonate, 0.035 M sodium bicarbonate, pH 9.6). Wells were blocked with 300 µl of InBlock blocking buffer (Inbios, Seattle, Wash., UN FA1032) for 60 minutes at 37° C. in a humidified chamber. 50 µl of sera were added to each well and incubated again for 60 minutes at 37° C. in a humidified chamber. Human test sera were diluted 1:400 in sample dilution buffer (Inbios, L/N FA1055). Positive control sera were diluted 1:3000 for SLEV and 1:800 for WNV. Positive and negative control VLP antigens were tested on all patient sera in triplicate by diluting appropriately in sample dilution buffer and adding 50 µl to appropriate wells for incubation overnight at 4° C. in a humidified chamber. Captured antigens were detected with 50 µl/well of polyclonal rabbit anti-pCBWN diluted 1:1000 in sample'dilution buffer and incubated for 60 m at 37° C. in a humidified chamber. Rabbit sera was detected with horseradish peroxidase conjugated goat anti-rabbit sera diluted 1:8000 in 1 µM conjugate dilution buffer (Inbios, UN FA1056) and incubated for 60 m at 37° C. in a humidified chamber. Bound conjugate was detected with 75 µl of 3,3'5,5'-tetramethylbenzidine (Neogen Corp, Lexington, Ky.) substrate, incubated at RT for 10 min, stopped with 50 µl of $2NH_2SO_4$, and then read at $A_{450}$ using an ELx405HT Bio-Kinetics microplate reader (Bio-Tek Instruments Inc., Winooski, Vt.).
IgM Test Validation and Interpretation Test validation and P/N values were determined according to the procedure of Martin et al. (*J. Clin. Micro.* 38:1823-26, 2000), using internal positive and negative serum controls included in each 96-well plate. Positive (P) values for each specimen were determined as the average $A_{450}$ for the patient serum sample incubated with positive VLP antigen. Negative (N) values were determined for each plate as the average $A_{450}$ for the normal human serum control incubated with positive VLP antigen.
Human Serology To determine how representative the murine antibody response (mAb data) is as a model of the human antibody response (serological data) to the viral substitution antigens described herein, serological assays were performed with single substitution, prototype type-specific antigens. As the mAb screening results indicated that fusion peptide residue 106 was incorporated into multiple cross-reactive epitopes for both WNV and SLEV, this substitution was selected to conduct MAC-ELISA serum tests.

The prototype type-specific $G_{106}$V-WNV Ag dramatically outperformed the wild-type (wt)-WNV Ag when tested on 10 difficult to discern 'equivocal' or positively 'misleading' SLEV-infected patient sera (Table 12). Six of 10 of these SLEV infected sera were correctly diagnosed as WNV-negative by MAC-ELISA (P/N≤2.0) with the $G_{106}$V-WNV prototype Ag, three were 'equivocal' (P/N>2.0≤3.0) and one was WNV positive. However, when these same sera were tested with the wt-WNV Ag, only four sera were correctly scored as WNV negative, one was equivocal, and five were misdiagnosed as WNV positive with this unmodified Ag. When antigens were directly compared on each individual serum sample, the $G_{106}$V-WNV Ag produced lower P/N ratios than did the wt-WNV Ag in nine of 10 cases on these SLEV infected sera, indicating that the $G_{106}$V-WNV Ag exhibits improved specificity and reduced cross-reactivity relative to the wt-WNV Ag.

The prototype type-specific $G_{106}$V-WNV Ag also outperformed the unaltered wt-WNV Ag in MAC-ELISA sensitivity tests on positive WNV infected human sera (Table 12). Five of six WNV infected patient sera had positive P/N ratios when tested with the $G_{106}$V-WNV Ag, whereas four were positive with the wt-WNV Ag. The single WNV positive serum sample that tested negative with the wt-Ag and equivocal with the $G_{106}$V Ag had the lowest neutralizing titers of the WNV sera in the PRNT (see Table 12), indicative of a weak antibody titer.

In addition to improved accuracy with the $G_{106}$V-WNV Ag, it was also more sensitive than was the wt-WNV Ag. In 5 of the 6 WNV infected sera, the MAC-ELISA P/N ratios were higher with the $G_{106}$V- than with the wt-WNV Ag (Table 12). Higher P/N ratios are expected from an improved type-specific Ag relative to the cross-reactive wt Ag when tested on sera infected with the same virus.

The prototype type-specific $G_{106}$V-WNV Ag exhibited improved specificity, accuracy, and sensitivity relative to the unmodified wt-WNV Ag. The $G_{106}$V-WNV Ag was more specific and accurate for WNV diagnosis than was the wt Ag, correctly diagnosing more WNV infected sera as positive and fewer SLEV infected sera as negative, than did the wt-WNV Ag. The $G_{106}$V-WNV Ag was also more sensitive at detecting WNV antibody in WNV infected serum than was the wt-WNV Ag. The positive signal indicating the presence of WNV antibody (P/N ratios) was greater for $G_{106}$V-WNV Ag than it was for the wt-Ag when testing WNV infected sera, and less than that of the wt-Ag when testing non-WNV infected sera.

EXAMPLE 6

Murine Immunization

This example demonstrates the ability of prototypical type-specific flavivirus mutant compositions to generate type-specific neutralizing antibody responses in mice.
Mouse Vaccination Groups of six female outbred ICR mice were used in this study. Mice were immunized by injection with pCB8D2-2J-2-9-1, pCB8D2-2J-2-9-1-$G_{106}$Q, pCBWN, pCBWN-$G_{106}$V, pCB8SJ2, or pCB8SJ2-$G_{106}$Q expression plasmids as described herein. Each mouse was injected with 100 µg of Picogreen® fluorometer quantified plasmid DNA in PBS pH 7.5, at a concentration of 1 µg/µl. Mice were immunized with 50 µg of plasmid DNA injected intramuscularly into each thigh on weeks 0 and 3. Mice were bled on week six following initial vaccination.
Plaque Reduction Neutralization Assays Six week post-vaccination serum specimens were tested for the presence of type-specific neutralizing (Nt) antibody (Ab) by plaque reduction neutralization test (PRNT). PRNT was performed with freshly confluent Vero cell monolayers as described by Chang et al. (*J. Virol.* 74:4244-52, 2000) using DENV-2 (16681), WNV (NY-99), and SLEV (MSI-7) viruses.
Neutralizing Antibody Responses Mice were immunized with wild-type and $G_{106}$ substituted plasmids for WNV, SLEV, and DENV-2 to determine if there were differences between the wild-type and $G_{106}$ prototype type-specific antigens for type-specific Nt Ab titer, cross-reactive Nt Ab titer, and protection from virus challenge. The type-specific Nt Ab titer results are shown in Table 13. There was little difference in the 75% PRNT titer between wt and $G_{106}$ substituted plasmids for all three viruses. The 75% Nt Ab titer was greater than or equal to 1:128 for almost all of the mice immunized with both the DENV-2 and both the WNV DNA vaccines. One mouse immunized with the wt DENV-2 DNA vaccine had a 75% PRNT titer of 1:64, and two mice immunized with the pCBWN-G106V DNA vaccine had 75% PRNT titers of 1:64 and 1:16.

These results demonstrate that for all three Flaviviruses tested, there was little to no detectable difference in type-specific neutralizing antibody titer between the prototype type-specific $G_{106}$ mutant vaccines and their wt counterparts. These results also illustrate that the methods described herein for ablating cross-reactive epitope residues can be used to generate type-specific flavivirus prM/E expression plasmids for use as DNA vaccines that still maintain potent type-specific neutralizing immunogenicity.

EXAMPLE 7

Reduction of Cross-Reactive Immunogenicity of Type-Specific Genetic Vaccines This example provides methods by which prototypical type-specific flavivirus mutant compositions can be used to generate a reduced cross-reactive neutralizing antibody response relative to the unaltered wild-type compositions.
Mouse Vaccination and Plague Reduction Neutralization Assays Female outbred ICR mice (such as the mice in Example 6) can be used in this study. Twelve-week post vaccination serum samples from immunized mice will be tested for cross-reactive (heterologous) Nt antibody response by PRNT. Unlike the type-specific PRNTs performed in Example 6, the cross-reactive PRNTs will be performed by examining Nt of immunized mouse sera not only for the type-specific virus used for immunization, but also for Nt of the seven other medically important flaviviruses. Thus, all 12-week mouse sera will be tested for neutralization against eight different flaviviruses: all four dengue serocomplex viruses, DENV-1 (16007), DENV-2 (16681), DENV-3 (H87), and DENV-4 (H241); three JEV serocomplex viruses, JEV (SA14-14-2), WNV (NY-99) and SLEV (MSI-7); and the single medically important member of the yellow fever virus serocomplex, YFV (17D).
Predicted Antibody Response Without being bound by theory, similar type-specific Nt Ab titers between the prototype type-specific $G_{106}$ mutant vaccines and their wt counterparts are expected. Thus, both pCBWN and pCBWN-$G_{106}$V vaccinated mouse sera are predicted to have similar Nt Ab titers against WNV, and pCB8D2-2J-2-9-1 and pCB8D2-2J-2-9-1-$G_{106}$Q will have similar Nt Ab titers against DENV-2. However, when these same sera are tested for Nt against the heterologous flaviviruses, it is expected that significantly lower PRNT titers for prototype type-specific $G_{106}$ mutant vaccinated mouse sera will be observed than for the counterpart wt vaccinated mouse sera. For example, mice immunized with pCBWN and pCBWN-$G_{106}$V will both have similar PRNT titers against WNV, whereas, pCBWN-$G_{106}$V immunized mice will have significantly lower PRNT titer against SLEV, JEV, YF, and the four dengue serotype viruses, than wild-type pCBWN immunized mice.

EXAMPLE 8

Combining Multiple Cross-Reactive Epitope Substitutions into Single Plasmid Constructs This example provides methods by which individual substitutions affecting different flavivirus cross-reactive epitopes can be combined into a single construct.

Individual substitutions affecting different flavivirus cross-reactive epitopes (such as those disclosed herein) can be combined into a single construct based, for example, on mAb screening results disclosed herein (see, Tables 3, 10 and 11), as well as additional mAb screening studies. For example, a mutagenesis primer has been designed for SLEV to introduce both the $G_{106}Q$ and $L_{107}K$ substitutions into a single pCB8SJ2 plasmid (see, Table 5). This double mutation plasmid has been constructed, and its sequence confirmed.

Cells can be transformed with this double mutated plasmid (or another plasmid containing a sequence encoding an E glycoprotein having a combination of two or more mutated amino acids), and the antigen characterized. In SLEV, the $G_{106}Q$ substitution alone alters the reactivities of many mAbs recognizing distinct cross-reactive epitopes (Table 10). However, this substitution alone has no significant effect on the flavivirus group cross-reactive epitope recognized by MAb T-23-1. The $L_{107}K$ substitution does knock out the ability of mAb T-23-1 to recognize the flavivirus cross-reactive epitope. Without being bound by theory, this suggests that $L_{107}$ is incorporated in the cross-reactive epitope recognized by mAb T-23-1, while $G_{106}$ is not.

Because of the generally additive effects observed when combining these substitutions into single constructs (see, Tables 10 and 11), it is expected that $G_{106}/L_{107}K$ antigen will combine the different effects observed from mAb screening of the individual mutants into a single, multiple substituted mutant. Upon transfection into mammalian cells, such a multiple mutant plasmid can be used to produce improved type-specific antigens. When utilized as genetic vaccines, these plasmids are expected to exhibit further reductions in cross-reactive immunogenicity while still inducing a potent type-specific immune response.

EXAMPLE 9

Immune Stimulatory Compositions for the Inhibition or Treatment of a Flavivirus Infection This example provides methods for administering substances suitable for use as immune stimulatory compositions for the inhibition or treatment of a flavivirus infection.

An immune stimulatory composition containing a therapeutically effective amount of a flavivirus polypeptide that includes at least one flavivirus cross-reactive epitope with reduced or ablated cross-reactivity (particularly in an E glycoprotein) can be administered to a subject at risk for, or exposed, to a flavivirus (e.g., a dengue virus, West Nile virus, etc.). Alternatively, an immune stimulatory composition containing a therapeutically effective amount of a nucleic acid vector that includes flavivirus nucleic acid molecules described herein, or that includes a nucleic acid sequence encoding at least one flavivirus cross-reactive epitope with reduced or ablated cross-reactivity (particularly in an E glycoprotein), can be administered to a subject at risk for, or exposed to a flavivirus.

Dosages and routes of administration for the immune stimulatory composition can be readily determined by one of ordinary skill in the art. Therapeutically effective amounts of an immune stimulatory composition can be determined, in one example, by in vitro assays or animal studies. When in vitro or animal assays are used, a dosage is administered to provide a target tissue concentration similar to that which has been shown to be effective in the in vitro or animal assays.

While this disclosure has been described with an emphasis on preferred embodiments, it will be apparent to those of ordinary skill in the art that variations and equivalents of the preferred embodiments may be used and it is intended that the disclosure may be practiced otherwise than as specifically described herein. Accordingly, this disclosure includes all modifications encompassed within the spirit and scope of the disclosure as defined by the claims below.

APPENDIX I

Tables

TABLE 1

Nucleotide sequence of primers used for mutagenesis. The mismatched nucleotides causing the desired substitutions are underlined.

| Sequence | SEQ ID NO: | Mutation |
|---|---|---|
| 5'-TGTTGTTGTGTTGGTTAG<u>G</u>TTTGCCTCTATACAG-3' | 1 | $K_{64}N$ |
| 5'-TGGGTTCCCCTTG<u>C</u>ATTGGGCAGCGAGATTCTGTTGTTG-3' | 2 | $T_{76}M$ |
| 5'-TTCATTTAGGCTGGGTTCCCC<u>T</u>CGTGTTGGGCAG-3' | 3 | $Q_{77}R$ |
| 5'-CCCTTTCCAAATAGTCCACA<u>GT</u>GATTTCCCCATCCTCTGTCTACC-3' | 4 | $G_{104}H$ |
| 5'-GCCTCCCTTTCCAAATAGT<u>T</u>GACATCCATTTCCCCA-3' | 5 | $G_{106}Q$ |
| 5'-GGTCACAATGCCTCCCTTTCCAAAT<u>TTT</u>CCACATCCATTTCCCC-3' | 6 | $L_{107}K$ |
| 5'-AGTTTTCTGGTTGCACAACTTTTCCT<u>G</u>CCATGTTCTTTTTGC-3' | 7 | $E_{126}A$ |
| 5'-GTATCCAATTTGACCCTTG<u>A</u>TTGTCCGCTCCGGGCAACC-3' | 8 | $T_{226}N$ |
| 5'-GTCTCTTTCTGTATG<u>A</u>AATTTGACCCTTGTGTGTC-3' | 9 | $W_{231}F$ |

TABLE 1-continued

Nucleotide sequence of primers used for mutagenesis. The mismatched nucleotides causing the desired substitutions are underlined.

| Sequence | SEQ ID NO: | Mutation |
|---|---|---|
| 5'-AATGTCTCTTTCTGTATCAGATTTGACCCTTGTGTGTCCGCTCC-3' | 10 | $W_{231}L$ |
| 5'-TCCTGTTTCTTCGCACGGGGATTTTTGAAAGTGACC-3' | 11 | $H_{244}R$ |
| 5'-ACAACAACATCCTGTCGCTTCGCATGGGGATTTTTG-3' | 12 | $K_{247}R$ |

TABLE 2

Stability free energy (ddG) calculations for putative domain II cross-reactive epitope substitutions based upon the published pdb coordinates for the DEN-2 virus (Modis et al., *PNAS* 100: 6986-91, 2003) and the TBE virus (Rey et al., *Nature* 375: 291-98, 1995) E-glycoprotein structures.

| DEN-2 SUB | ddG (kcal/mol) | TBE SUB | ddG (kcal/mol) |
|---|---|---|---|
| K64N | −0.45 | K64N | −0.15 |
| T76M | −0.54 | T76M | −0.02 |
| Q77R | 0.45 | M77R | −0.10 |
| G104H | −0.16 | H104H | NA |
| G106Q | 0.87 | G106Q | −0.03 |
| L107K | 0.19 | L107K | 0.12 |
| E126A | 2.16 | K126A | 0.85 |
| T226N | 0.33 | Q233N | 0.03 |
| E126A/T226N | 2.49 | K126A/Q233N | 0.88 |
| W231F | 1.54 | W235F | 1.34 |
| W231L | 1.84 | W235L | 2.26 |
| H244R | 4.18 | H248R | 0.00 |
| K247R | −0.30 | K251R | −0.19 |

TABLE 3 mAb reactivities for mutant and wild-type plasmids.

| mAb | D2HIAF | 4G2 | 6B6C1 | 4E5 | 1A5D1 | 1B7-5 | 10A1D2 |
|---|---|---|---|---|---|---|---|
| Epitope | polyclonal | A1 | A1 | A2 | A3 | A5 | A/C |
| PRNT | + | + | +/− | + | − | + | − |
| SA | + | + | + | + | − | +/− | +/− |
| Specificity | NA | group | group | sub-comp. | type | sub-group | comp. |
| Wild Type | | | | | | | |
| IFA | 4.1 | 3.8 | 3.8 | 2.6 | 4.4 | 4.1 | ≥2.9 |
| Ag-ELISA | >6.0 | >6.0 | ≥6.0 | ≥2.9 | 4.2 | 5.7 | >3.8 |
| T76M | | | | | | | |
| IFA | — | — | — | — | — | — | — |
| Ag-ELISA | — | — | — | — | ≤5% | — | — |
| G104H | | | | | | | |
| IFA | — | <3% | 6% | — | <0.8% | 3% | — |
| Ag-ELISA | na | na | na | na | na | na | na |
| G106Q | | | | | | | |
| IFA | — | <3% | <3% | — | <0.8% | — | nd |
| Ag-ELISA | — | <0.1% | <0.1% | — | <6% | — | 13% |
| L107K | | | | | | | |
| IFA | — | <3% | — | — | — | — | <25% |
| Ag-ELISA | — | <0.1% | — | — | 5% | — | 6% |
| E126A | | | | | | | |
| IFA | — | — | 6% | — | — | — | — |
| Ag-ELISA | — | — | — | — | 10% | 13% | — |
| E126A/T226N | | | | | | | |
| IFA | — | — | 3% | — | — | 3% | <25% |
| Ag-ELISA | — | — | — | — | 5% | 13% | — |
| W231F/L | | | | | | | |
| IFA | — | <3% | <3% | — | — | <2% | — |
| Ag-ELISA | na | na | na | na | na | na | — |

TABLE 3-continued mAb reactivities for mutant and wild-type plasmids.

| mAb<br>Epitope<br>PRNT<br>SA<br>Specificity | 1B4C2<br>C1<br>−<br>+<br>sub-comp. | 9A4D1<br>C4<br>+<br>−<br>type | 3H5<br>B1<br>+<br>+<br>type | 9A3D8<br>B2<br>+<br>+<br>type | 10A4D2<br>B3<br>+<br>+<br>sub-comp. | 9D12<br>B4<br>+<br>+<br>type |
|---|---|---|---|---|---|---|
| Wild Type | | | | | | |
| IFA | 4.4 | ≥2.9 | >4.4 | 3.5 | 4.1 | >4.4 |
| Ag-ELISA | >5.3 | 2.9 | >6.0 | >6.0 | >6.0 | >6.0 |
| T76M | | | | | | |
| IFA | — | — | — | nd | — | nd |
| Ag-ELISA | 0.8% | — | — | — | — | — |
| G104H | | | | | | |
| IFA | — | — | — | nd | — | nd |
| Ag-ELISA | na | na | na | na | na | na |
| G106Q | | | | | | |
| IFA | 6% | nd | — | — | — | — |
| Ag-ELISA | ≤0.1% | — | — | — | — | — |
| L107K | | | | | | |
| IFA | 6% | — | — | nd | — | nd |
| Ag-ELISA | 0.2% | — | — | — | — | — |
| E126A | | | | | | |
| IFA | — | — | — | nd | — | nd |
| Ag-ELISA | — | — | — | — | — | — |
| E126A/T226N | | | | | | |
| IFA | — | — | — | nd | — | nd |
| Ag-ELISA | — | — | — | — | — | — |
| W231F/L | | | | | | |
| IFA | 6% | — | — | — | — | — |
| Ag-ELISA | — | — | — | — | — | — | na: not applicable (these constructs did not secrete VLP antigen and thus could not be examined by Ag-ELISA); nd: not determined.

TABLE 4

Amino acid sequence variability for proposed cross-reactive epitope residues in domain II of the flavivirus E protein.

| Virus | K64N | T76M | Q77R | G104H | G106Q | L107K | E126A | T226N | W231/F, L | H244R | K247R |
|---|---|---|---|---|---|---|---|---|---|---|---|
| DEN-2 | K | T | Q | G | G | L | E | T | W | H | K |
| DEN-4 | S | T | Q | G | G | L | T | T | W | H | R |
| DEN-3 | K | T | Q | G | G | L | E | T | W | H | K |
| DEN-1 | K | T | Q | G | G | L | E | T | W | H | K |
| Japanese Encephalitis | S | T | T | G | G | L | I | T | W | H | K |
| Murray Valley encephalitis | T | T | T | G | G | L | A | T | W | H | K |
| West Nile | T | T | M | G | G | L | I | T | W | H | K |
| St. Louis encephalitis | T | T | T | G | G | L | T | T | W | H | K |
| Ilhéus | T | T | M | G | G | L | E | T | W | H | R |
| Rocio | T | T | M | G | G | L | M | D | W | H | R |
| Bagaza | K | T | M | G | G | L | E | G | W | H | K |
| Iguape | E | Q | M | G | G | L | P | G | W | H | K |
| Bussuquara | K | A | V | G | G | L | A | S | W | H | K |
| Kokobera | Q | T | M | G | G | L | E | G | W | H | K |
| Kédougou | T | T | Q | G | G | L | K | A | W | H | K |
| Zika | S | T | Q | G | G | L | T | T | W | H | R |
| Yellow fever | V | S | T | G | G | L | S | G | W | H | T |
| Sepik | S | T | M | G | G | L | E | G | W | H | T |
| Entebbe Bat | N | T | T | G | G | L | Q | D | W | H | S |
| Tick-borne encephalitis | K | T | M | H | G | L | T | Q | W | H | K |
| Louping ill | K | T | M | H | G | L | T | P | W | H | K |
| Omske hemorrhagic fever | K | A | M | H | G | L | T | V | W | H | K |
| Langat | K | T | M | H | G | L | T | E | W | H | K |
| Alkhurma | K | A | M | H | G | L | T | H | W | H | K |
| Deer tick | K | T | T | H | G | F | V | Q | W | H | K |
| Powassan | K | T | T | H | G | F | V | Q | W | H | K |
| Montana myotis leukoencephalitis | D | T | L | G | G | L | A | H | W | H | K |

TABLE 4-continued

Amino acid sequence variability for proposed cross-reactive epitope residues in domain II of the flavivirus E protein.

| Virus | K64N | T76M | Q77R | G104H | G106Q | L107K | E126A | T226N | W231/F, L | H244R | K247R |
|---|---|---|---|---|---|---|---|---|---|---|---|
| Rio Bravo | S | T | Q | G | G | L | I | S | W | H | K |
| Modoc | E | T | Q | G | A | L | M | P | W | Y | K |
| Apoi | A | T | Q | G | G | L | I | K | W | H | K |

DENV-2 strains containing variable amino acid sequences at these positions are indicated below with their GenBank accession numbers (all incorporated by reference as of the date of filing of this application).
64R: AF359579; 77L: M24449, X15434, X15214; 107F: M24446
126K: L10053, D00346, M29095, AF204178, M24450, M24451, AF410348, AF410361, AF410362, AF410365, AF204177, D10514
226K: AB111452, AY158337; 247R: AF231718, AF231719, AF231720

TABLE 5

Nucleotide sequence of primers used for mutagenesis. The mismatched nucleotides causing the desired substitutions are underlined.

| Primer | Sequence | SEQ ID NO: | Mutation |
|---|---|---|---|
| SLEV: | | | |
| G104H | CTCCCTTTTCCAAACAGACCACAGTGGTTACCCCATCCGC | 31 | Gly-His |
| G104N | CTCCCTTTTCCAAACAGACCACAGTTGTTACCCCATCCGC | 32 | Gly-Asn |
| G104D | CCCTTTTCCAAACAGACCACAGTCGTTACCCCATCCGC | 33 | Gly-Asp |
| G104K | CTCCCTTTTCCAAACAGACCACACTTGTTACCCCATCCGC | 34 | Gly-Lys |
| G106Q | CTCCCTTTTCCAAACAGCTGACATCCGTTACCCCATCCGC | 35 | Gly-Gln |
| G106K | CTCCCTTTTCCAAACAGCTTACATCCGTTACCCCATCCGC | 36 | Gly-Lys |
| G106V | TCCCTTTTCCAAACAGTACACATCCGTTACCCCATCCGC | 37 | Gly-Val |
| G016D | CTTTTCCAAACAGATCACATCCGTTACCCCATCCGC | 38 | Gly-Asp |
| L107F | CTCCCTTTTCCAAAGAAACCACATCCGTTACCCCATCCGC | 39 | Leu-Phe |
| G106Q/L107F | AATGCTCCCTTTTCCAAAGAACTGACATCCGTTACCCCATCCGC | 40 | Gly-Gln-Leu-Phe |
| R166Q | CGGGCTTATGGTGAATTGAGCCGCTTGGTTTTTCC | 41 | Arg-Gln |
| T177I | TTCCATACTCGCCCATGTTGGCAATAAAGGACGGTG | 42 | Thr-Ile |
| G181S | GTAACTGTTCCATACTCGGACATGTTGGCCGTAAAGG | 43 | Gly-Ser |
| E182N | GTAACTGTTCCATAGTTGCCCATGTTGGCCGTAAAGG | 44 | Glu-Asn |
| T231N | CTCTGTTGCGCCAATCGTTTGTGGCAGGGCTCGTC | 45 | Thr-Asn |
| W233F | TTCTCTGTTGCGGAAATCAGTTGTGGCAGGGCTCGTC | 46 | Trp-Phe |
| H246R | TACTACAGTTTGCTTGGTGGCACGCGGTTCCTC | 47 | His-Trp |
| S276G | TGATTGCAAGGTTAGGGTTGATCCGCTAACAGTGGC | 48 | Ser-Gly |
| K294Y | CGTTCCCTTGATTTTGACGTAGTCAAGCTTAGCTCTGC | 49 | Lys-Tyr |
| T301A | ACACATGCCATATGCCGTTCCCTTGATTTTGACC | 50 | Thr-Ala |
| T330D | CAGGGTCCGTTGCTTCCATCATACTGCAGTTCCAC | 51 | Thr-Asp |
| A367S | CGATCATGACCTTGTTGTTCGATCCCCCTGTGC | 52 | Ala-Ser |
| N368F | TTCGATCATGACCTTGTTGAACGCTCCCCCTGTGC | 53 | Asn-Phe |
| WNV: | | | |
| G014N | TTTGCCAAATAGTCCGCAGTTGTTGCCCCAGCCCC | 54 | Gly-Asn |
| G104D | TTGCCAAATAGTCCGCAGTCGTTGCCCCAGC | 55 | Gly-Asp |
| G104K | CCTTTGCCAAATAGTCCGCACTTGTTGCCCCAGCCCC | 56 | Gly-Lys |
| G104A | TTGCCAAATAGTCCGCATGCGTTGCCCCAGC | 57 | Gly-Ala |

TABLE 5-continued

Nucleotide sequence of primers used for mutagenesis. The mismatched nucleotides causing the desired substitutions are underlined.

| Primer | Sequence | SEQ ID NO: | Mutation |
|---|---|---|---|
| G106V | TTTGCCAAATAGGACGCAGCCGTTGCCCCAGCC | 58 | Gly-Val |
| G106R | TTTGCCAAATAGCCTGCAGCCGTTGCCCCAGCC | 59 | Gly-Arg |
| G106Y | CCTTTGCCAAATAGGTAGCAGCCGTTGCCCCAGCCCC | 60 | Gly-Tyr |
| G106A | TTTGCCAAATAGAGCGCAGCCGTTGCCCCAGCC | 61 | Gly-Ala |
| L107Y | TTCCTTTGCCAAAGTATCCGCAGCCGTTGCCCCAGCC | 62 | Gly-Tyr |
| L107F | CCTTTGCCAAAGAATCCGCAGCCGTTGCCCCAGC | 63 | Gly-Phe |
| L107H | CCTTTGCCAAAATGTCCGCAGCCGTTGCCCCAGC | 64 | Gly-His |
| L107R | CCTTTGCCAAATCTTCCGCAGCCGTTGCCCCAGC | 65 | Gly-Arg |
| K118V | CTTGGTAGAGCAGGCAAATACGGCGCATGTGTC | 66 | Lys-Val |
| N154D | CCAACCTGTGTGGAGTAGTCTCCGTGCGAC | 67 | Asn-Asp |
| Y155G | CCAACCTGTGTGGAGCCGTTTCCGTGCGACTC | 68 | Tyr-Gly |
| Q158D | CTGAGTGGCTCCAACATCTGTGGAGTAGTTTCCGTGCG | 69 | Gln-Asp |
| R166Y | AGGAGTGATGCTGAAGTACCCTGCCTGAGTGG | 70 | Arg-Tyr |
| T177V | CCAAGCTTTAGTACGTATGAAGGCGCCGCAGGAG | 71 | Thr-Val |
| E182G | CCTCTCCATAGCCTCCAAGCTTTAGTGTGTATGAAGG | 72 | Glu-Gly |
| W233F | AACGTCTCTCTGTTCCTGAACACAGTACTTCCAGCAC | 73 | Trp-Phe |
| S276D | CCGACGTCAACTTGACAGTGTTGTCTGAAAATTCCACAGG | 74 | Ser-Asp |
| K294N | GTTCCCTTCAACTGCAAGTTTTCCATCTTCACTCTACAC | 75 | Lys-Asn |
| T301N | ACAGACGCCATAGTTTGTTCCCTTCAACTGCAATTTTTCC | 76 | Thr-Asn |
| T330N | CCATCCGTGCCGTTGTACTGCAATTCCAACACCACAG | 77 | Thr-Asn |
| A367V | GGACCTTAGCGTTGACCGTGGCCACTGAAAC | 78 | Ala-Val |
| N368S | ACCTTAGCGCTGGCCGTGGCCACTGAAAC | 79 | Asn-Ser |

TABLE 6

E-glycoprotein-specific mAbs recognizing each of the three E-glycoprotein domains

| mAb Name | Virus | Specificity | Domain |
|---|---|---|---|
| 4G2 | DENV-2 | group | DII |
| 6B6C-1 | SLEV | group | DII |
| T23-1 | WNV | group | DII |
| T23-2 | JEV | group | DII |
| 2B6B-2 | SLEV | sub-grp (not WNV) | DII |
| 4A1B-9 | MVEV | group | DII |
| 1B7-5 | DENV-3 | sub-grp: DEN + JE comp | |
| T21 | DENV-3 | sub-grp: DEN + JE comp | |
| 2B5B-3 | SLEV | sub-grp. JE comp + YF | |
| T11 | DENV-3 | sub-grp: DEN-2,3,4 + JE | |
| T5-1 | JEV | sub-grp: DEN-2, JE, SLE | |
| T5-2 | JEV | sub-grp: DEN-1,2, JE, WN* | |
| 10A1D-2 | DENV-2 | sub-grp: DEN-1,2,3,4 + SLE | DI/DII |
| 6B4A-10 | JEV | JE comp. | |
| T16 | JEV | JE comp. | |
| 1B4C-2 | DENV-2 | sub-comp: DEN-2,3 | DI |
| 10A4D-2 | DENV-2 | sub-comp: DEN-1,2,3 | DIII |
| 1B5D-1 | SLEV | sub-comp: SLE + JE | E-2 |
| T20 | DENV-2 | sub-comp: DEN-2 + JEV | |
| 4E5 | DENV-2 | sub-comp: DEN-1,2,3 | DII |
| 3H5 | DENV-2 | type | DIII |
| 9A3D-8 | DENV-2 | type | DIII |
| 9D12 | DENV-2 | type | DIII |
| 1A5D-1 | DENV-2 | type | DII |
| 9A4D-1 | DENV-2 | type | DI |
| T8 | WNV | type | |
| 3.91D | WNV (KUNV) | type | |
| 3.67G | WNV (KUNV) | type | |
| 4A4C-4 | SLEV | type | |
| 6B5A-2 | SLEV | type | |
| 1B2C-5 | SLEV | type | |

TABLE 7

Potential DENV-2 complex- and sub-complex-cross-reactive epitope residues, with residues chosen for mutagenesis highlighted

| D2# | D1# | D3# | D4# | Dom? | B-f | Location | SC? | CRE? |
|---|---|---|---|---|---|---|---|---|
| K51 | T51* | T51 | K51 | DI/DII | med | top outer edge | yes | yes |
| Q52 | N52 | Q52 | E52 | DI/DII | high | top outer edge SDM in D2 | yes | yes |
| Q86 | Q86 | Q86 | Q86 | DII | high | out-mid-lat. SDM in D2 | ~yes | yes |
| Q131 | Q131 | Q131 | Q131 | DII/DI | high | out low lat mid SDM in D216681 | ~yes | ?no |
| H149* | H149 | H149 | H149 | DI | high | up-mid-top below CHO-153 | yes | yes if no CHO |
| N153* | N153 | N153 | N153 | DI | med | up-mid-top near CHO 153 | yes | no |
| D154 | E145 | E154 | D154 | DI | high | up-in-top near CHO & prM | yes | YES? |
| T155* | T155 | T155 | T155 | DI | high | up-mid-top near prM | yes | YES |
| E161 | T161 | T161 | T161 | DI | high | up-mid-top high. exp. | yes | yes |
| Q167 | Q167 | Q167 | R167 | DI | high | out-lat mid DI/II region | yes | pos? |
| S169 | P169 | S169 | P169 | DI | med+ | DI/II border out-mid | yes | yes? |
| E172 | E172 | E172 | E172 | DI | high | DI/II border up-out edge | yes | yes |
| T176 | T176 | P176 | P176 | DI | med | DI/III up-out edge | yes | yes |
| G177* | D177 | E177 | D177 | DI | med | DI/III up-out edge | yes | yes |
| E202 | E202 | K202 | E202 | DII | high | in-mid-up | YES | YES |
| D203 | K203 | N203 | K203 | DII | high | in-mid-up no SDM in D2 | yes | yes |
| A224 | A224 | A224 | A224 | DII | med+ | up-out-middle (SDM in D2) | yes | yes |
| T226 | T226 | T226 | T226 | DII | high | up-out-mid SDM previous | yes | no?? |
| Q227 | S227 | K227 | S227 | DII | high | up-out-middle | yes | yes? |
| D290 | D290 | D290 | E290 | DI | high | out-up lat DI/III face | yes | maybe |
| K291 | K291 | K291 | K291 | DI | med+ | out-up lat DI/III face, above D290 | YES | yes? |
| M297 | M297 | M297 | M297 | DIII/I | high | mid-out-end DI/III SDM D2? | ~yes | ?yes? |
| S298 | S298 | S298 | S298 | DIII/I | med+ | mid-out-end DI/III flavis = S/T | YES | YES |
| T303 | T303 | L303 | S303 | DIII | high | mid-out-end DI/III | YES | ?yes |
| K310* | K310 | K310 | K310 | DIII | low | out-up DI-DII interface | ~YES | YES? |
| E311 | E311 | E311 | E311 | DIII | high | out-up DI-DII interface | YES | YES |
| E327* | E327 | K327 | E327 | DIII | high | up-out-top "end" DIII | YES | YES |
| D229 | T229 | E229 | A229 | DIII | high | up-out-top "end" DIII | yes | yes |
| E360 | D360 | K360 | N360 | DIII | med+ | tip-top-mid DIII | yes | no |
| K361 | K361 | K361 | T361 | DIII | high | tip-top-mid DIII | YES | YES |
| D362 | E362 | E362 | N362 | DIII | med | tip-top-mid DIII | yes | yes |
| V382* | A382 | I382 | V382 | DIII | low | "RGD" loop up-out-lat | ~yes | ?pos |
| E383 | G383 | G383 | G383 | DIII | high | "RGD" loop up-out-lat | ~?no | yes |
| P384 | E384 | E384 | N384 | DIII | med+ | "RGD" loop up-out-lat | YES | yes? |

*not identified as ≥35% SA in this particular structure/model

B-f: β-factor (temperature factor) a qualitative assessment of the scale (5-60Å$^2$).

SC?: is the amino acid side chain accessible and available for antibody binding

Ep?: might this amino acid be incorporated into an antigen epitope?

DVc: DENV 1-4 complex;

Jec: JE complex (medically important clade = JE, MVE, WN, SLE)

SDM: site-directed mutagenesis

TABLE 8

Potential JEV complex- and sub-complex cross-reactive epitope residues from WNV, with residues chosen for mutagenesis highlighted

| D2# | SLE# | WN# | Dom. | B-f. | Location? | SC? | Conservation | Ep? |
|---|---|---|---|---|---|---|---|---|
| T68* | L68 | L68 | DII | low | top inner edge near N67 D2 | ~yes | WN, SLE = L | ?yes |
| T76 | T76 | T76 | DII | low | out-lateral-low-mid. | yes | "all" mos. + ticks | ? |
| Q77 | T77* | M77 | DII | med | outer lateral middle | no | variable, Q = DVc | ? |
| N83 | T83 | D83 | DII | med | out-up-lat. loop near FP | yes | variable type? | Yes |
| Q86 | S86 | A86 | DII | high | out-mid-lat. | ~yes | JEc = A (SLE = S) | yes |
| K88 | P88 | P88 | DII | high | out-up-lat | ~no? | varaiable | ?possible |
| M118 | K118 | K118 | DII | med+ | up-mid-top near N67 in D2 | yes | JEc = K, SDM in WN | YES |
| K122 | K122 | S122 | DII | med+ | up-mid-top | yes | var. | yes |
| Q131 | L131 | L131 | DII/DI | high | out mid lat DI/II border | ~yes | var. L = WN, SLE | ?/YES |
| H149* | S149 | V149 | DI | high | up-mid-top below CHO-153 | yes | H = DVc | yes if no CHO |

TABLE 8-continued

Potential JEV complex- and sub-complex cross-reactive epitope residues from WNV, with residues chosen for mutagenesis highlighted

| N153* | N154 | N154 | DI | med+ | up-mid-top CHO on D2-153 | yes | "all mosq" = N | YES |
|---|---|---|---|---|---|---|---|---|
| NA* | Y155 | Y155 | DI | na | up-mid-top near CHO 153 yes | Y = JEc | SDM in WN | YES |
| D154 | Q158 | Q158 | DI | high | up-in-top near CHO & prM | yes | Q = Jec, SDM in WN | YES |
| T155* | I159* | V159 | DI | high | up-mid-top near prM | yes | DVc = t JEc = I/V | YES |
| E161 | R166 | R166 | DI | high | up-mid-top high. exp. | yes | JEc = R, except JE = K | yes |
| S169 | P174 | P174 | DI | med+ | DI/II border out-mid | yes | P = mosq. (D2,3 = S) | yes? |
| E172 | T177 | T177 | DI | high | DI/II border up-out-top edge | yes | DVc = E, JEc = T | yes |
| E174 | N179 | K179 | DI | high | DI/III border outer edge | yes | var. JEc = K (SLE = N) | yes? |
| T176 | G181 | G181 | DI | med | DI/III up-out edge | yes | DVc = var, JEc = G | yes |
| G177* | E182 | E182 | DI | med | DI/III up-out edge | yes | "all" mosq = neg D2 = G | yes |
| T226 | T231 | T231 | DII | high | up-out-mid. SDM? | yes | DVc, JEc = T | yes? |
| H244* | H246 | H246 | DII | med | prM hole low but above P243 | yes | all flavis | no? |
| K247 | K249 | K249 | DII | med | prM hole low, above 243/244 | yes | "all" flavis | no? |
| S274 | S276 | S276 | DII/I | high | up-top-in good aa JEc | YES | JEc = S, SDM WN | YES |
| K291 | K294 | K294 | DI | med+ | out-up lat DI/DII face | ~yes | flavis = K | yes? |
| M297 | T300 | T300 | DIII/I | high | mid-out-end DI/III | ~yes | DVc = M JEc = T | ?pos? |
| S298 | T301 | T301 | DIII/I | med+ | mid-out-end DI/III | YES | flavis = S/T | YES |
| E327* | T330 | T330 | DIII | high | up-out-top "end" DIII | YES | JEc = T ex JE = S | YES |
| K361 | A367 | A367 | DIII | high | tip-top-mid DIII YES | | JEc = A | SDM in WN | YES |
| D362 | N368 | N368 | DIII | med | tip-top-mid DIII YES | | JEc = N | SDM in WN | YES |
| V382* | R388 | R388 | DIII | low | "RGD" loop up-out-lat yes | | JEc = R | | YES |
| E383 | G389* | G389 | DIII | high | "RGD" loop up-out-lat ~y/na | | mosq = G or E | | YES |

*not identified as ≥35% SA in this particular structure/model
B-f: β-factor (temperature factor) a qualitative assessment of the scale (5-60Å$^2$).
SC?: is the amino acid side chain accessible and available for antibody binding
Ep?: might this amino acid be incorporated into an antigen epitope?
DVc: DENV 1-4 complex;
Jec: JE complex (medically important clade = JE, MVE, WN, SLE)
SDM: site-directed mutagenesis

TABLE 9

Potential JEV complex- and sub-complex cross-reactive epitope residues from SLEV, with residues chosen for mutagenesis highlighted

| D2# | SLE# | WN# | Dom. | B-f. | Location? | SC? | Conservation | Ep? |
|---|---|---|---|---|---|---|---|---|
| T68* | L68 | L68 | DII | low | top inner edge near N67 D2 | ~yes | WN, SLE = L | ?yes |
| T76 | T76 | T76 | DII | low | out-lateral-low-mid | yes | "all" mosq. + ticks | ? |
| Q77 | T77* | M77 | DII | med | outer lateral middle | no | variable, Q = DVc | ? |
| N83 | T83 | D83 | DII | med | out-up-lat. loop near FP | yes | variable type? | Yes |
| Q86 | S86 | A86 | DII | high | out-mid-lat. | ~yes | JEc = A (SLE = S) | yes |
| K88 | P88 | P88 | DII | high | out-up-lat | ~no? | variable | ?possible |
| K122 | K122 | S122 | DII | med+ | up-mid-top | yes | var. | yes |
| Q131 | L131 | L131 | DII/DI | high | out low lat mid | ~yes | var. L = WN, SLE | ?/no |
| H149* | S149 | V149 | DI | high | up-mid-top below CHO-153 | yes | H = DVc; | yes if no CHO |
| N153* | N154 | N154 | DI | med+ | up-mid-top CHO on D2-153 | yes | "all mosq" = N | YES |
| NA* | Y155 | Y155 | DI | na | up-mid-top near CHO 153 | Y = JEc | SDM SLE | YES |
| D154 | Q158 | Q158 | DI | high | up-in-top near CHO & prM | yes | Q = Jec, SDM SLE | YES |
| T155* | I159* | V159 | DI | high | up-mid-top near prM | yes | DVc = T JEc = I/V | YES |
| E161 | R166 | R166 | DI | high | up-mid-top high. exp. | yes | JEc = R, except JE = K | yes |
| S169 | P174 | P174 | DI | med+ | DI/II border out-mid | yes | P = mosq. (D2,3 = S) | yes? |
| E172 | T177 | T177 | DI | high | DI/II border up-out-top edge | yes | DVc = E, JEc = T | YES |
| E174 | N179 | K179 | DI | high | DI/III border outer edge | yes | var. JEc = K (SLE = N) | yes? |
| T176 | G181 | G181 | DI | med | DI/III up-out edge | yes | DVc = var, JEc = G | yes |
| G177* | E182 | E182 | DI | med | DI/III up-out edge | yes | "all" mosq = neg D2 = G | yes |
| T226 | T231 | T231 | DII | high | up-out-mid. SDM prev. | yes | DVc, JEc = T | yes? |
| H244* | H246 | H246 | DII | med | prM hole low but above P243 | yes | all flavis | yes? |
| K247 | K249 | K249 | DII | med | prM hole low, above 243/244 | yes | "all" flavis | no? |
| S274 | S276 | S276 | DII/I | high | up-top-in good aa JEc | YES | JEc = S, SDM SLE | YES |
| K291 | K294 | K294 | DI | med+ | out-up lat DI/III face | ~yes | flavis = K | yes? |
| M297 | T300 | T300 | DIII/I | high | mid-out-end DI/III | ~yes | DVc = M JEc = T | ?pos? |
| S298 | T301 | T301 | DIII/I | med+ | mid-out-end DI/III | YES | flavis = S/T | YES |
| E327* | T330 | T330 | DIII | high | up-out-top "end" DIII | YES | JEc = T ex JE = S | YES |
| K361 | A367 | A367 | DIII | high | tip-top-mid DIII | YES | JEc = A SDM in SLE | YES |
| D362 | N368 | N368 | DIII | med | tip-top-mid DIII | YES | JEc = N SDM in SLE | YES |
| V382* | R388 | R388 | DIII | low | "RGD" loop up-out-lat | ~yes | JEc = R | YES |
| E383 | G389* | G389 | DIII | high | "RGD" loop up-out-lat | ~y/na | mosq = G or E | YES |

TABLE 9-continued

Potential JEV complex- and sub-complex cross-reactive epitope residues from SLEV, with residues chosen for mutagenesis highlighted

*not identified as ≥35% SA in this particular structure/model
B-f: β-factor (temperature factor) a qualitative assessment of the scale (5-60Å$^2$).
SC?: is the amino acid side chain accessible and available for antibody binding
Ep?: might this amino acid be incorporated into an antigen epitope?
DVc: DENV 1-4 complex;
Jec: JE complex (medically important clade = JE, MVE, WN, SLE)
SDM: site-directed mutagenesis

TABLE 10

Inverse log$_{10}$ end-point titers of anti-SLEV mAbs determined by the AG-ELISA for antigens expressed by wild-type pCB8SJ2 and cross-reactive reduced mutated constructs

| Mutants | | Mabs: CR: virus: Secrete? | MHIAF poly SLEV | 4G2 grp D2V | T-23-1 grp WNV | T-23-2 grp JEV | 6B6C-1 grp SLEV | 2B6B-2 grp SLEV | 4A1B-9 grp MVEV | 1B7-5 supr comp D3V | 2B5B-3 supr comp SLEV | T-16 JE comp JEV | 6B4A-10 JE comp JEV | 1B5D-1 JEV+SEV JEV | 6B5A-2 SLEV MSI-7 | 4A4C-4 SLEV MSI-7 | 1B2C-5 SLEV MSI-7 |
|---|---|---|---|---|---|---|---|---|---|---|---|---|---|---|---|---|---|
| pCB8SJ2 | ELISA | + | >>4.8 | >>4.5 | >4.5 | >6.0 | >4.5 | >4.5 | >4.5 | >4.5 | >4.5 | >4.5 | >4.5 | >3.5 | >4.5 | >4.5 | ≥4.5 |
| | IFA | | >4.4 | ~4.4 | >4.4 | | >4.4 | ~4.4 | <4.4 | <4.1 | >4.4 | >4.4 | ~4.4 | ~3.8 | | | |
| G104H | ELISA | − | >>4.8 | nd | ≤3.0 | ≤3.0 | nd | nd | nd | nd | ≤3.0 | nd | nd | nd | nd | nd | ≥4.5 |
| | IFA | | >4.4? | ≤2.3 | ≤2.3 | | ≤2.3 | ≤2.3 | ≤2.3 | ≤2.6 | ≤3.0 | ≤3.5 | ≤2.6 | ≤2.3 | | | |
| G106Q | ELISA | + | >>4.8 | ≤3.0 | >4.5 | >6.0 | >4.5 | >4.5 | >4.5 | ≥3.0 | ≤4.5 | ≤4.5 | >4.5 | >4.5 | >4.5 | >4.5 | ≤4.5 |
| | IFA | | >4.4 | ≤3.2 | >4.4 | | ≤2.3 | 4.4 | ≤2.3 | ≥4.5 | ~4.1 | >4.4 | ~4.4 | ~2.3 | | | |
| L107K | ELISA | + | >>4.8 | ≤3.0 | ≤3.0 | >6.0 | >4.5 | >4.5 | >4.5 | ≥4.5 | ≤3.0 | >4.5 | >4.5 | >3.5 | >4.5 | >4.5 | ≥4.5 |
| | IFA | | >4.4 | ≤2.3 | ~3.2 | | ~3.8 | 4.4 | ≤4.4 | ≤4.1 | >4.4 | >4.4 | ~4.4 | ~3.5 | | | |
| R166Q | ELISA | + | >>4.8 | >>4.5 | >4.5 | >6.0 | >4.5 | >4.5 | >4.5 | ≥4.5 | >4.5 | >4.5 | >4.5 | >3.5 | >4.5 | >4.5 | ≥4.5 |
| | IFA | | >4.4 | ≥4.4 | >4.4 | | >4.4 | ~2.2 | ≤4.4 | ≤4.1 | >4.4 | >4.4 | ~4.4 | ~4.1 | | | |
| T177I | ELISA | +/− | >>4.8 | >>4.5 | >4.5 | >6.0 | >4.5 | >4.5 | >4.5 | ≥4.5 | >4.5 | >4.5 | >4.5 | >3.5 | nd | nd | nd |
| | IFA | | >4.4 | ≥4.4 | >4.4 | | >4.4 | 4.1 | ≤4.4 | ≤4.1 | >4.4 | >4.4 | ~4.4 | ~4.1 | | | |
| G181S | ELISA | −/+ | >>4.8 | >>4.5 | >4.5 | >6.0 | >4.5 | >4.5 | >4.5 | ≥4.5 | >4.5 | >4.5 | >4.5 | ~2.3 | >4.5 | >4.5 | nd |
| | IFA | | >4.4 | ≥4.4 | >4.4 | | >4.4 | 4.4 | ≤4.4 | ≤4.1 | >4.4 | >4.4 | ~4.4 | ~3.5 | | | |
| E182N | ELISA | −/+ | >>4.8 | >>4.5 | ≤3.0 | >6.0 | ≤3.0 | >4.5 | >4.5 | ≥4.5 | ≤3.0 | >4.5 | >4.5 | nd | nd | nd | nd |
| | IFA | | >4.4 | ≥4.4 | >4.4 | | ~3.5 | ~4.4 | ≤4.4 | ≤4.1 | >4.4 | >4.4 | ~4.4 | ~4.1 | | | |
| T231N | ELISA | + | >>4.8 | >>4.5 | >4.5 | >6.0 | >4.5 | >4.5 | >4.5 | ≥4.5 | ≤3.0 | >4.5 | >4.5 | >3.5 | >4.5 | >4.5 | ≥4.5 |
| | IFA | | >4.4 | ≥4.4 | >4.4 | | >4.4 | ~4.4 | ≤4.4 | ≤4.1 | >4.4 | >4.4 | ~4.4 | ~3.8 | | | |
| W233F | ELISA | −/+ | >>4.8 | >>4.5 | nd | >6.0 | >4.5 | >4.5 | >4.5 | ≥4.5 | ≤3.0 | >4.5 | >4.5 | >3.5 | >4.5 | >4.5 | ≥4.5 |
| | IFA | | >4.4 | ≥4.4 | >4.4 | | >4.4 | ~4.4 | ≤4.4 | ≤4.1 | >4.4 | >4.4 | ~4.4 | ~3.5 | | | |
| H246R | ELISA | ++ | >>4.8 | >>4.5 | >4.5 | >6.0 | | >4.5 | >4.5 | ≥4.5 | >4.5 | >4.5 | >4.5 | ~2.3 | >4.5 | >4.5 | ≥4.5 |
| | IFA | | >4.4 | ≥4.4 | >4.4 | | >4.4 | ~4.4 | ≤4.4 | ≤4.1 | >4.4 | >4.4 | ~4.4 | ~3.2 | | | |
| S276G | ELISA | + | >>4.8 | >>4.5 | >4.5 | >6.0 | >4.5 | >4.5 | >4.5 | ≤4.1 | >4.5 | >4.5 | >4.5 | >3.5 | >4.5 | >4.5 | ≥4.5 |
| | IFA | | >4.4 | ≥4.4 | >4.4 | | >4.4 | ~4.4 | ≤4.4 | ≤4.1 | >4.4 | >4.4 | ~4.4 | ~4.1 | | | |
| K294Y | ELISA | − | >>4.8 | >>4.5 | ≤3.0 | 4.8 | >4.5 | >4.5 | nd | ≥4.5 | >4.5 | >4.5 | nd | nd | nd | nd | nd |
| | IFA | | >4.4 | ≥4.4 | >4.4 | | >4.4 | ~4.4 | ≤4.4 | ≤4.1 | >4.4 | >4.4 | ~4.4 | ~3.2 | | | |
| T301A | ELISA | + | >>4.8 | >>4.5 | <4.5 | >6.0 | >4.5 | >4.5 | >4.5 | ≥4.5 | >4.5 | >4.5 | >4.5 | >3.5 | >4.5 | >4.5 | ≥4.5 |
| | IFA | | >4.4 | ≥4.4 | <4.4 | | >4.4 | ~4.4 | ≤4.4 | ≤4.1 | >4.4 | >4.4 | ~4.4 | ~3.8 | | | |
| T330D | ELISA | + | nd | >>4.5 | nd | >6.0 | >4.5 | >4.5 | >4.5 | ≥4.5 | nd | >4.5 | >4.5 | >3.5 | >4.5 | >4.5 | ≥4.5 |
| | IFA | | >4.4 | ≥4.4 | >4.4 | | >4.4 | ~4.4 | ≤4.4 | ≤4.1 | >4.4 | >4.4 | ~4.4 | ~4.1 | | | |
| A367S | ELISA | +/− | >>4.8 | >>4.5 | >4.5 | >6.0 | >4.5 | >4.5 | >4.5 | ≥4.5 | >4.5 | >4.5 | >4.5 | >3.5 | >4.5 | >4.5 | ≥4.5 |
| | IFA | | >4.4 | ≥4.4 | >4.5 | | >4.4 | ~4.4 | ≤4.4 | ≤4.1 | >4.4 | >4.4 | ~4.4 | ~3.5 | | | |
| N368F | ELISA | −/+ | >>4.8 | ≤3.0 | >4.5 | >6.0 | ~4.5 | >4.5 | >4.5 | ≥4.5 | >4.5 | >4.5 | >4.5 | >3.5 | >4.5 | >4.5 | ≥4.5 |
| | IFA | | >4.4 | ≥4.4 | >4.4 | | ~4.1 | ~4.4 | ≤4.4 | ≤4.1 | >4.4 | >4.4 | ~4.4 | ~3.5 | | | |
| G106Q/ E182N | ELISA | + | 4.8 | ≤3.0 | >4.5 | >4.5 | ≤3.0 | ≥4.5 | >4.5 | 4.5 | ≤3.0 | >4.5 | >4.5 | 4.5 | >4.5 | >4.5 | >4.5 |
| | IFA | | ≥4.1 | ≤2.3 | >4.4 | | ≤2.3 | ≤2.3 | ≤2.3 | ≤2.3 | ≤2.3 | 3.5 | ~3.2 | ≤2.3 | | | |
| G106Q/ K294Y | ELISA | − | nd | ≤3.0 | nd | nd | ≤3.0 | nd | nd | nd | nd | ≤3.0 | nd | nd | nd | nd | nd |
| | IFA | | ~4.1 | ≤2.3 | >4.4 | | ≤2.3 | ≤2.3 | ≤2.3 | ≤2.3 | ≤2.3 | ~2.3 | ≤2.3 | ≤2.3 | | | |
| G106Q/ N368F | ELISA | + | 4.8 | ≤3.0 | >4.5 | >4.5 | >4.5 | >4.5 | ≥4.5 | >4.5 | ≤3.0 | >4.5 | ≥4.5 | 4.5 | >4.5 | ≥4.5 | >4.5 |
| | IFA | | ≥4.4 | ≤2.3 | >4.4 | | ≤2.3 | ≤2.3 | ≤2.3 | ~4.4 | ≤3.2 | 4.4 | ~4.1 | ≤2.3 | | | |
| 106-182-294 | ELISA | − | nd | ≤3.0 | nd | nd | ≤3.0 | nd | nd | nd | ~2.3 | nd | ≤3.0 | nd | nd | nd | nd |
| | IFA | | ~4.1 | ≤2.3 | ~3.8 | | ≤2.3 | <2.3 | <2.3 | 2.3 | ~2.3 | ~2.3 | ≤2.3 | <2.3 | | | |
| 106-182-368 | ELISA | −/+ | 4.8 | ≤3.0 | >4.5 | >4.5 | ≥4.5 | 4.2 | ≥4.5 | ≥4.5 | ≤3.0 | ≥4.5 | ≥4.5 | 4.5 | nd | >4.5 | nd |
| | IFA | | ~4.4 | ≤2.3 | >4.4 | | <2.3 | <2.3 | <2.3 | <2.3 | ≥3.5 | ≤2.3 | 3.5 | ~3.8 | <2.3 | | | |
| 106-294-368 | ELISA | − | nd | ≤3.0 | nd | nd | ≤3.0 | nd | nd | nd | nd | nd | <3.0 | nd | nd | nd | nd |
| | IFA | | ~4.1 | ≤2.3 | >4.4 | | ≤2.3 | <2.3 | <2.3 | 3.5 | ~2.3 | 3.8 | ≤3.5 | <2.3 | | | |
| 106-182-294-368 | ELISA | − | nd | ≤3.0 | nd | nd | ≤3.0 | nd | nd | nd | nd | nd | <3.0 | nd | nd | nd | nd |
| | IFA | | ~4.1 | ≤2.3 | >4.4 | | ≤2.3 | ≤2.3 | ≤2.3 | ≤2.3 | ~2.3 | ≤2.3 | ~2.3 | ≤2.3 | | | |

Shaded block: Significantly altered endpoints relative to pCB8SJ2 derived wild-type VLP antigens. Most substitutions reduced mAb reactivity, however, some mAbs reactivity increased.

TABLE 11

Inverse log₁₀ end-point titers of anti-WNV mAbs determined by the AG-ELISA for antigens expressed by wild-type pCBWN and cross-reactive reduced mutated constructs

| Mutants | | Mabs:<br>CR:<br>virus:<br>Secrete? | MHIAF<br>poly<br>WNV | 4G2<br>grp<br>D2V | T-23-1<br>grp<br>WNV | T-23-2<br>grp<br>JEV | 6B6C-1<br>grp<br>SLEV | 4A1B-9<br>grp<br>MVEV | 2B5B-3<br>supr comp<br>SLEV | T-16<br>JE comp<br>JEV | 6B4A-10<br>JE comp<br>JEV | 3.67G<br>type<br>Kun | 3.91D<br>type<br>Kun |
|---|---|---|---|---|---|---|---|---|---|---|---|---|---|
| pCBWN | ELISA | ++ | 5.7 | >4.5 | >4.5 | >6.0 | >4.5 | >4.5 | >4.5 | >6.0 | >4.5 | >4.5 | >4.5 |
| | IFA | | | | ≥4.1 | >4.1 | | | >4.1 | >4.1 | >4.1 | ≥4.1 | ≥4.1 |
| G104N | ELISA | − | na | na | ≤3.0 | na | na | na | na | na | na | nd | nd |
| | IFA | | ~3.2 | | ≤2.0 | ~3.2 | | | ≤2.0 | ≤2.6 | <3.2 | 3.5 | ≥4.1 |
| G106V | ELISA | + | 5.7 | ≤3.0 | >4.5 | >6.0 | <3.0 | ≤3.0 | ≤3.0 | >6.0 | >4.5 | >4.5 | >4.5 |
| | IFA | | ≥4.1 | | >4.4 | >4.1 | | | ≤2.0 | >4.1 | >4.1 | ≥4.1 | ≥4.1 |
| L107Y | ELISA | +/− | 5.7 | na | >4.5 | >6.0 | na | na | nd | >6.0 | na | nd | nd |
| | IFA | | ≥4.1 | | ≤2.0 | >4.1 | | | ≤2.0 | >4.1 | >4.1 | ≥4.1 | ≥4.1 |
| K118V | ELISA | − | 5.7 | >4.5 | >4.5 | na | na | na | na | >4.5 | na | nd | nd |
| | IFA | | ≥4.1 | | >4.1 | >4.1 | | | >4.1 | >4.1 | <3.8 | ≥4.1 | ≥4.1 |
| N154D | ELISA | ++ | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | >4.1 | 4.1 | ≥4.1 | ≥4.1 |
| Y155G | ELISA | + | 5.7 | >4.5 | >4.5 | >>6.0 | >4.5 | >4.5 | >4.5 | >6.0 | >4.5 | >4.5 | >4.5 |
| | IFA | | ≥4.1 | | >4.1 | >4.1 | | | >4.1 | >4.1 | >4.1 | ≥4.1 | ≥4.1 |
| Q158D | ELISA | + | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | >4.1 | >4.1 | ≥4.1 | ≥4.1 |
| R166Y | ELISA | ++ | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | >4.1 | >4.1 | ≥4.1 | ≥4.1 |
| T177V | ELISA | + | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.0 | 4.1 | ≥4.1 | ≥4.1 |
| E182G | ELISA | + | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.0 | <4.1 | ≥4.1 | ≥4.1 |
| W233F | ELISA | ++ | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.0 | <4.1 | ≥4.1 | ≥4.1 |
| S276D | ELISA | ++ | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.0 | >4.1 | ≥4.1 | ≥4.1 |
| K294N | ELISA | + | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤3.5 | >4.1 | ≥4.1 | ≥4.1 |
| T301N | ELISA | + | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.9 | >4.1 | ≥4.1 | ≥4.1 |
| T330N | ELISA | + | 5.7 | >4.5 | >4.5 | >6.0 | >4.5 | >4.5 | >4.5 | >6.0 | >4.5 | nd | nd |
| | IFA | | >4.1 | | >4.1 | >4.1 | | | >4.1 | ≤2.6 | >4.1 | ≥4.1 | ≥4.1 |
| A367V | ELISA | ++ | 5.7 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.9 | <4.1 | ≥4.1 | ≥4.1 |
| N368S | ELISA | ++ | ~6.0 | >4.5 | >4.5 | >6.0 | >4.5 | >4.5 | >4.5 | >6.0 | >4.5 | >4.5 | >4.5 |
| | IFA | | ≥4.1 | | >4.1 | >4.1 | | | >4.1 | ≤2.9 | >4.1 | ≥4.1 | ≥4.1 |
| G106V/<br>T301N | ELISA<br>IFA | + | 5.7 | ≤3.0 | >4.5 | >4.5 | >3.0 | | ≤3.0 | >4.5 | >4.5 | | |
| G106V/<br>T330N | ELISA<br>IFA | −/+ | 5.7<br>3.8 | ≤3.0 | >4.5<br>>4.1 | >4.5<br>>4.1 | >3.3 | | ≤3.0<br>≤2.0 | >4.5<br>≤3.8 | ~4.5<br>3.8 | ~3.8 | ~3.8 |
| G106V/<br>T301N<br>T330N | ELISA<br>IFA | −/+ | 5.7<br>≥4.1 | ≤3.0 | >4.5<br>>4.1 | >4.5<br>>4.1 | >3.3 | | ≤3.0<br>≤2.0 | >4.5<br>4.1 | ≥4.5<br>4.1 | 4.1 | 4.1 |

Shaded block: Significantly altered endpoints relative to pCB8SJ2 derived wild-type VLP antigens. Most substitutions reduced mAb reactivity, however, some mAbs reactivity increased.

TABLE 12

Comparative detection of human IgM antibody by MAC-ELISA with wild type (wt-) and G106V- prototype type-specific antigens.

| Serum Specimen Description | | | PRNT₉₀[2] | | Positive/Negative Ratios[2] | | | |
|---|---|---|---|---|---|---|---|---|
| | | | | | Ref. Lab. Result | | VLP MAC-ELISA | |
| Infecting Virus | No | Class[1] | SLEV | WNV | SLEV | WNV | wt | G106V |
| SLEV | 1 | equivocal | 160 | 20 | 1.10 | 0.81 | 1.12 | 1.02 |
| | 2 | equivocal | 160 | 20 | 1.17 | 1.20 | 1.11 | 1.16 |
| | 3 | equivocal | 320 | 40 | 2.10 | 1.30 | 1.83 | 1.15 |
| | 4 | equivocal | 320 | 80 | 2.40 | 2.90 | 1.74 | 1.34 |
| | 5 | equivocal | 320 | 20 | 8.56 | 8.27 | 3.12 | 1.99 |
| | 6 | misleading | 1280 | 160 | 8.27 | 10.8 | 5.40 | 5.09 |
| | 7 | misleading | 1280 | 20 | 9.81 | 11.1 | 6.42 | 2.35 |
| | 8 | misleading | 640 | 20 | 12.4 | 14.9 | 3.76 | 2.48 |

TABLE 12-continued

Comparative detection of human IgM antibody by MAC-ELISA with wild type (wt-) and G106V- prototype type-specific antigens.

| Serum Specimen Description | | PRNT$_{90}$[2] | | Ref. Lab. Result | | VLP MAC-ELISA | |
|---|---|---|---|---|---|---|---|
| Infecting Virus | No | Class[1] | SLEV | WNV | SLEV | WNV | wt | G106V |
| | 9 | misleading | 160 | 40 | 13.0 | 20.3 | 2.02 | 1.47 |
| | 10 | misleading | 1280 | 10 | 11.8 | 43.7 | 9.80 | 2.04 |
| No. positive | | | | | 6 | 6 | 5 | 1 |
| WNV | 1 | positive | 40 | 160 | 3.37 | 7.88 | 1.91 | 2.45 |
| | 2 | positive | 160 | 2560 | 1.48 | 5.76 | 3.12 | 4.09 |
| | 3 | positive | 10 | 320 | 1.29 | 8.61 | 4.21 | 3.20 |
| | 4 | positive | 80 | 320 | 2.73 | 8.38 | 2.71 | 3.04 |
| | 5 | positive | 40 | 2560 | 2.12 | 26.3 | 6.68 | 9.04 |
| | 6 | positive | 40 | 1280 | 2.14 | 28.8 | 8.27 | 10.2 |
| No. positives | | | | | 1 | 6 | 4 | 5 |

[1]Sera were assigned to one of three classes; positive, equivocal, or misleading as described in materials and methods. Assignments were based upon previously determined P/N ratios[3] reported by the Diagnostics and Reference Laboratory, Arbovirus Diseases Branch, Division of Vector-Borne Diseases, US Centers for Disease Control and Prevention.
[2]PRNT$_{90}$, Plaque reduction neutralization test; titers represent inverse 90% plaque reduction endpoints as reported by the Diagnostics and Reference Laboratory, ADB, DVBID, CDC.
[3]Values represent ratios calculated as described in Materials and Methods. Positive ratios ≥3.0 are shown in bold
[4]Ratios reported by the Diagnostics and Reference Laboratory, ADB, DVBID, CDC.
[5]Ratios determined in this study comparing wild-type (wt-) WNV Ag. with prototype cross-reactivity reduced G106V-WNV Ag.

TABLE 13

Type-specific neutralizing antibody titers as determined by PRNT

| Plasmid DNA used for immunization[1] | Mouse No. | Type-specific 75% PRNT titer[2] |
|---|---|---|
| pCB8D2-2J-2-9-1 (wt DENV-2) | 1 | >128 |
| | 2 | >128 |
| | 3 | >128 |
| | 4 | 64 |
| | 5 | >128 |
| | 6 | >128 |
| pCB8D2-2J-2-9-1-G106Q (DENV-2 + G106Q) | 1 | >128 |
| | 2 | >128 |
| | 3 | >128 |
| | 4 | >128 |
| | 5 | 128 |
| | 6 | >128 |
| pCBWN (wt WNV) | 1 | >128 |
| | 2 | >128 |
| | 3 | >128 |
| | 4 | >128 |
| | 5 | >128 |
| | 6 | >128 |
| pCBWN-G106V (WNV + G106V) | 1 | 64 |
| | 2 | >128 |
| | 3 | 16 |
| | 4 | >128 |
| | 5 | >128 |
| | 6 | >128 |

[1]Mice were immunized intramuscularly with 100 ug of plasmid DNA on weeks 0 and 3.
[2]PRNT plaque reduction neutralization test, 75% neutralization endpoint titers on mouse sera collected 6 weeks post vaccination.

We claim:

1. An isolated nucleic acid molecule encoding a mutant flavivirus E-glycoprotein polypeptide comprising at least one amino acid substitution at position 104 or 106 compared to a wild type flavivirus E-glycoprotein polypeptide, wherein the mutant E-glycoprotein polypeptide exhibits reduced antibody cross-reactivity as compared to the wild type E-glycoprotein polypeptide, and wherein the flavivirus is selected from the group consisting of dengue serotype 1 virus, dengue serotype 2 virus, dengue serotype 3 virus, dengue serotype 4 virus, St. Louis encephalitis virus, and West Nile virus.

2. The nucleic acid molecule of claim 1, comprising the nucleic acid sequence as shown in SEQ ID NO: 15, 17, 82, or 86.

3. A recombinant nucleic acid molecule, comprising a regulatory sequence operably linked to the nucleic acid molecule of claim 1.

4. An isolated cell, comprising the recombinant nucleic acid molecule of claim 3.

5. The isolated cell of claim 4, wherein the cell is a eukaryotic cell.

6. A composition, comprising:
a nucleic acid vector that comprises the nucleic acid molecule of claim 3; and
a pharmaceutically acceptable carrier.

7. A method of eliciting an immune response against a flavivirus antigenic epitope in a subject, comprising administering an immunogenically effective amount of the composition of claim 6 to the subject.

8. The method of claim 7, wherein the flavivirus antigenic epitope is selected from the group consisting of dengue serotype 1 virus, dengue serotype 2 virus, dengue serotype 3 virus, dengue serotype 4 virus, St. Louis encephalitis virus, and West Nile virus.

9. The method of claim 7, wherein the subject is a mammal.

10. The isolated nucleic acid molecule of claim 1, wherein the flavivirus is dengue serotype 2 virus and the nucleic acid molecule encodes an amino acid substitution comprising $G_{104}H$, $G_{106}Q$, or a combination thereof.

11. The isolated nucleic acid molecule of claim 1, wherein the flavivirus is St. Louis encephalitis virus and the nucleic acid molecule encodes an amino acid substitution comprising $G_{104}H$, $G_{106}Q$, or a combination thereof.

12. The isolated nucleic acid molecule of claim 1, wherein the flavivirus is West Nile virus and the nucleic acid molecule encodes an amino acid substitution comprising $G_{104}N$, $G_{106}V$, or a combination thereof.

13. The isolated nucleic acid molecule of claim 1, wherein the nucleic acid molecule encodes a polypeptide comprising the amino acid sequence as shown in SEQ ID NOs: 16, 18, 83, or 87.

14. The isolated nucleic acid molecule of claim 1, further comprising an amino acid substitution at position 107 compared to a wild type flavivirus E-glycoprotein polypeptide.

15. An isolated nucleic acid molecule encoding a mutant flavivirus E-glycoprotein polypeptide comprising an amino acid substitution at at least two of positions 104, 106, or 107 compared to a wild type flavivirus E-glycoprotein polypeptide, wherein the mutant E-glycoprotein polypeptide exhibits reduced antibody cross-reactivity as compared to the wild type E-glycoprotein polypeptide and wherein the flavivirus is selected from the group consisting of dengue serotype 1 virus, dengue serotype 2 virus, dengue serotype 3 virus, dengue serotype 4 virus, St. Louis encephalitis virus, and West Nile virus.

16. The isolated nucleic acid molecule of claim 15, wherein the flavivirus is dengue serotype 2 virus and the nucleic acid molecule encodes an amino acid substitution comprising at least two of $G_{104}H$, $G_{106}Q$, or $L_{107}K$.

17. The isolated nucleic acid molecule of claim 15, wherein the flavivirus is St. Louis encephalitis virus and the nucleic acid molecule encodes an amino acid substitution comprising at least two of $G_{104}H$, $G_{106}Q$, or $L_{107}K$.

18. The isolated nucleic acid molecule of claim 15, wherein the flavivirus is West Nile virus and the nucleic acid molecule encodes an amino acid substitution comprising at least two of $G_{104}N$, $G_{106}V$, or $L_{107}Y$.

19. A recombinant nucleic acid molecule, comprising a regulatory sequence operably linked to the nucleic acid molecule of claim 15.

20. A composition, comprising:
a nucleic acid vector that comprises the nucleic acid molecule of claim 18; and
a pharmaceutically acceptable carrier.

21. A method of eliciting an immune response against a flavivirus antigenic epitope in a subject, comprising administering an immunogenically effective amount of the composition of claim 20 to the subject.

* * * * *